US010259878B2

(12) United States Patent
Zhang et al.

(10) Patent No.: US 10,259,878 B2
(45) Date of Patent: Apr. 16, 2019

(54) ANTI-RANKL ANTIBODIES AND METHODS OF USE

(71) Applicant: Apexigen, Inc., San Carlos, CA (US)

(72) Inventors: Yongke Zhang, Palo Alto, CA (US);
Xiaodong Yang, Palo Alto, CA (US);
Guo-Liang Yu, Hillsborough, CA (US);
Weimin Zhu, Millbrae, CA (US)

(73) Assignee: APEXIGEN, INC., San Carlos, CA (US)

( * ) Notice: Subject to any disclaimer, the term of this patent is extended or adjusted under 35 U.S.C. 154(b) by 30 days.

(21) Appl. No.: 14/776,248

(22) PCT Filed: Mar. 11, 2014

(86) PCT No.: PCT/US2014/023623
§ 371 (c)(1),
(2) Date: Sep. 14, 2015

(87) PCT Pub. No.: WO2014/159430
PCT Pub. Date: Oct. 2, 2014

(65) Prior Publication Data
US 2016/0032001 A1 Feb. 4, 2016

Related U.S. Application Data

(60) Provisional application No. 61/786,050, filed on Mar. 14, 2013.

(51) Int. Cl.
*A61K 39/395* (2006.01)
*C07K 16/24* (2006.01)
*C07K 16/28* (2006.01)
*A61K 39/00* (2006.01)

(52) U.S. Cl.
CPC .. *C07K 16/2875* (2013.01); *A61K 39/001136* (2018.08); *A61K 39/001138* (2018.08); *C07K 16/24* (2013.01); *C07K 16/241* (2013.01); *A61K 2039/505* (2013.01); *C07K 2317/24* (2013.01); *C07K 2317/33* (2013.01); *C07K 2317/54* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,675,063 A | 10/1997 | Knight | |
| 7,429,487 B2 | 9/2008 | Pytela et al. | |
| 7,462,697 B2 | 12/2008 | Couto et al. | |
| 2003/0021785 A1* | 1/2003 | Dougall | C07K 14/70578 424/146.1 |
| 2004/0171117 A1 | 9/2004 | Tornetta et al. | |
| 2010/0104568 A1 | 4/2010 | Beirnaert et al. | |

FOREIGN PATENT DOCUMENTS

| | | |
|---|---|---|
| WO | WO 1992/001047 A1 | 1/1992 |
| WO | WO 2008/088594 | 7/2008 |
| WO | WO 2011/017294 A1 | 2/2011 |
| WO | WO 2014/159430 A1 | 10/2014 |
| WO | 2015/125922 A1 | 8/2015 |
| WO | WO 2015/125922 | 8/2015 |

OTHER PUBLICATIONS

Cacia et al., Biochemistry, 1996, vol. 35:1897-1903.*
Rudikoff et al., PNAS, 1982, vol. 79:1979-1983.*
Anderson et al., "A homologue of the TNF receptor and its ligand enhance T-cell growth and dendritic-cell function." Nature (1997); 390(6656):175-179.
Barbas et al. "In vitro evolution of a neutralizing human antibody to human immunodeficiency virus type 1 to enhance affinity and broaden strain cross-reactivity." Proceedings of the National Academy of Sciences (1994); 91.9: 3809-3813.
Barbas et al., "Human antibody recognition of DNA." Proceedings of the National Academy of Sciences (1995); 92(7): 2529-2533.
Barbas et al., "Recognition of DNA by synthetic antibodies." Journal of the American Chemical Society (1994); 116.5: 2161-2162.
Beiboer et al., "Guided selection of a pan carcinoma specific antibody reveals similar binding characteristics yet structural divergence between the original murine antibody and its human equivalent." Journal of Molecular Biology (2000); 296.3: 833-849.
Burgess et al., "The ligand for osteoprotegerin (OPGL) directly activates mature osteoclasts." J Cell Biol. (1999);145(3):527-38.
Carter et al. "Humanization of an anti-p185HER2 antibody for human cancer therapy." Proceedings of the National Academy of Sciences (1992); 89.10: 4285-4289.
Clackson et al., "Making antibody fragments using phage display libraries." (1991); 352: 624-628.
Co et al., "Humanized Antibodies for Antiviral Therapy." Proceedings of the National Academy of Sciences of the United States of America 88.7 (1991): 2869-2873.
Co et la., "Chimaeric and humanized antibodies with specificity for the CD33 antigen" J.Immunol. (1992); 148(4):1149-1154.
Fata et al., "The osteoclast differentiation factor osteoprotegerin-ligand is essential for mammary gland development." Cell (2000); 103.1: 41-50.
Fuller et al., TRANCE is necessary and sufficient for osteoblast-mediated activation of bone resorption in osteoclasts. J Exp Med. (1998); 188(5):997-1001.
Gori et al., "The expression of osteoprotegerin and RANK ligand and the support of osteoclast formation by stromal-osteoblast lineage cells is developmentally regulated." Endocrinology (2000);141(12):4768-76.
Gorman et al. "Reshaping a therapeutic CD4 antibody." Proceedings of the National Academy of Sciences (1991); 88.10: 4181-4185.
Gram et al., "In vitro selection and affinity maturation of antibodies from a naive combinatorial immunoglobulin library." Proceedings of the National Academy of Sciences (1992); 89.8: 3576-3580.

(Continued)

*Primary Examiner* — Xiaozhen Xie
(74) *Attorney, Agent, or Firm* — Cooley LLP

(57) ABSTRACT

The present invention provides anti-RANKL monoclonal antibodies and related compositions, which may be used in any of a variety of therapeutic methods for the treatment of rheumatoid arthritis and other diseases.

21 Claims, 26 Drawing Sheets
Specification includes a Sequence Listing.

(56) References Cited

OTHER PUBLICATIONS

Hofbauer et al. "Stimulation of Osteoprotegerin Ligand and Inhibition of Osteoprotegerin Production by Glucocorticoids in Human Osteoblastic Lineage Cells: Potential Paracrine Mechanisms of Glucocorticoid-Induced Osteoporosis 1." Endocrinology (1999); 140.10: 4382-4389.
Hsu et al., "Tumor necrosis factor receptor family member RANK mediates osteoclast differentiation and activation induced by osteoprotegerin ligand." Proc Natl Acad Sci U S A. (1999); 96(7): 3540-3545.
International Patent Application No. PCT/US2014/023623, International Preliminary Report on Patentability dated Sep. 15, 2015.
International Patent Application No. PCT/US2014/023623, International Search Report and Written Opinion dated Jun. 27, 2014.
Itonaga et al., "Rheumatoid arthritis synovial macrophage-osteoclast differentiation is osteoprotegerin ligand-dependent." The Journal of Pathology (2000); 192.1: 97-104.
Kartsogiannis et al., "Localization of RANKL (receptor activator of NF kappa B ligand) mRNA and protein in skeletal and extraskeletal tissues." Bone (1999); 25(5):525-34.
Kettleborough et al., "Humanization of a mouse monoclonal antibody by CDR-grafting: the importance of framework residues on loop conformation." Protein Engineering (1991); 4.7: 773-783.
Khosla, "Minireview: The opg/rankl/rank system." Endocrinology (2001); 142.12: 5050-5055.
Klimka et al. "Human anti-CD30 recombinant antibodies by guided phage antibody selection using cell panning." British Journal of Cancer (2000); 83.2: 252.
Komarova et al., "RANK ligand-induced elevation of cytosolic Ca2+ accelerates nuclear translocation of nuclear factor kappa B in osteoclasts." J Biol Chem. (2003); 278(10): 8286-8293.
Kong et al., "Activated T cells regulate bone loss and joint destruction in adjuvant arthritis through osteoprotegerin ligand." Nature (1999); 402(6759): 304-309.
Kong et al., "Osteoprotegerin ligand: a regulator of immune responses and bone physiology." Immunol Today (2000); 21(10): 495-502.
Lacey, et al., "Osteoprotegerin ligand is a cytokine that regulates osteoclast differentiation and activation." Cell (1998); 93(2): 165-76.
Lee et al., "Parathyroid hormone stimulates TRANCE and inhibits osteoprotegerin messenger ribonucleic acid expression in murine bone marrow cultures: correlation with osteoclast-like cell formation." Endocrinology (1999); 140(8): 3552-3561.
Lobuglio et al., "Mouse/human chimeric monoclonal antibody in man: kinetics and immune response." Proceedings of the National Academy of Sciences (1989); 86.11: 4220-4224.
Lum et al., "Evidence for a role of a tumor necrosis factor-alpha (TNF-alpha)-converting enzyme-like protease in shedding of TRANCE, a TNF family member involved in osteoclastogenesis and dendritic cell survival." J Biol Chem. (1999); 274(19): 13613-13618.
Maeda et al. "Construction of reshaped human antibodies with HIV-neutralizing activity." Human Antibodies (1991); 2.3: 124-134.
Marks et al., "By-Passing Immunization: Building High Affinity Human Antibodies by Chain Shuffling." Nature Biotechnology (1992); 10.7: 779-783.
McLane et al., "Transplantation of a 17-amino acid alpha-helical DNA-binding domain into an antibody molecule confers sequence-dependent DNA recognition." Proceedings of the National Academy of Sciences (1995); 92.11: 5214-5218.
Menaa et al., "Enhanced RANK ligand expression and responsivity of bone marrow cells in Paget's disease of bone." The Journal of Clinical Investigation (2000); 105.12: 1833-1838.
Muller et al., "VEGF and the Fab fragment of a humanized neutralizing antibody: crystal structure of the complex at 2.4 Å resolution and mutational analysis of the interface." Structure 6.9 (1998): 1153-1167.

Nagai et al., "Cancer cells responsible for humoral hypercalcemia express mRNA encoding a secreted form of ODF/TRANCE that induces osteoclast formation." Biochemical and Biophysical Research Communications (2000); 269.2: 532-536.
Nakashima et al., "RANKL and RANK as novel therapeutic targets for arthritis." Curr Opin Rheumatol. (2003); 15(3):280-287.
NCBI, GenBank accession No. AAO06458.1 (Dec. 26, 2002).
NCBI, GenBank accession No. AAT02407.1 (Jun. 3, 2004).
Pearse et al. "Multiple myeloma disrupts the TRANCE/ osteoprotegerin cytokine axis to trigger bone destruction and promote tumor progression." Proceedings of the National Academy of Sciences (2001); 98.20: 11581-11586.
Portolano et al., "Lack of promiscuity in autoantigen-specific H and L chain combinations as revealed by human H and L chain"roulette"." The Journal of Immunology (1993); 150.3: 880-887.
Queen et al., "A humanized antibody that binds to the interleukin 2 receptor." Proceedings of the National Academy of Sciences (1989); 86.24: 10029-10033.
Rader et al., "A phage display approach for rapid antibody humanization: designed combinatorial V gene libraries." Proceedings of the National Academy of Sciences (1998); 95.15: 8910-8915.
Riechmann et al., "Reshaping human antibodies for therapy." Nature (1988); 332.6162: 323-327.
Sato et al. "Reshaping a human antibody to inhibit the interleukin 6-dependent tumor cell growth." Cancer Research (1993); 53.4: 851-856.
Schier et al., "Isolation of picomolar affinity anti-c-erbB-2 single-chain Fv by molecular evolution of the complementarity determining regions in the center of the antibody binding site." Journal of Molecular Biology (1996); 263.4: 551-567.
Schwarz and Ritchlin, "Clinical development of anti-RANKL therapy", Arthritis Research & Therapy (2007); 9(Suppl 1): S7, pp. 1-6.
Stemmer "Rapid evolution of a protein in vitro by DNA shuffling." Nature (1994); 370.6488: 389-391.
Tempest et al., "Reshaping a human monoclonal antibody to inhibit human respiratory syncytial virus infection in vivo." Nature Biotechnology (1991); 9.3: 266-271.
Verhoeyen, "Reshaping human antibodies: Grafting an antilysozyme activity." Science (1988); 239: 1534-1536.
Wang et al., "Regulation of activation-induced receptor activator of NF-kappaB ligand (RANKL) expression in T cells." Eur J Immunol. (2002); 32(4):1090-8.
Wong et al., "TRANCE is a novel ligand of the tumor necrosis factor receptor family that activates c-Jun N-terminal kinase in T cells." Journal of Biological Chemistry (1997); 272.40: 25190-25194.
Wong et al., "TRANCE (tumor necrosis factor [TNF]-related activation-induced cytokine), a new TNF family member predominantly expressed in T cells, is a dendritic cell-specific survival factor." J Exp Med. (1997); 186(12):2075-2080.
Yasuda et al., "Osteoclast differentiation factor is a ligand for osteoprotegerin/osteoclastogenesis-inhibitory factor and is identical to TRANCE/RANKL." Proc Natl Acad Sci U S A. (1998); 95(7):3597-3602.
European Patent Office, European Patent Application No. EP 14775208. 3, Extended European Search Report dated Jan. 19, 2017, 13 pages.
Supplementary Partial European Search Report, EP 14775208, dated Oct. 7, 2016 (9 pages.
Kim, et al., "Osteoclast differentiation inhibitors: a patenet review (2008-2012)," Expert Opinion on Therapeutic Patents, 23(12):1591-1610 (2013).
Kostenuik, et al., "Denosumab, a Fully Human Monoclonal Antibody to RANKL, Inhibits Bone Resportion and Increases BMD in Knock-In Mice That Express Chimeric (Murine/Human) RANKL" Journal of Bone and Mineral Research, 24(2):182-195 (2009).

\* cited by examiner

Figure 1: Rabbit antibodies agonist to RANKL

Figure 1A:     Heavy Chain Variable Region amino acid alignment

```
7    QEQLKESGGGLVTPGGTLTLTCTASGFSLTT---NGMSWVRQAPGKGLEWIGYIY---SGGSPYYANWAKGRFTISKTSST-
20   QEQLKESGGGLVTPGGTLTLTCTASGFYLSS---NGMSWVRQAPGKGLEWIGYIY---SGGSPYYASWAKGRFTISKTSST-
23   QEQLKESGGGLVTPGGTLTLTCTASGFSLSS---DGMSWVRQAPGKGLEWIGYIY---SGSSPYYANWAKGRFTISKTSST-
37   -QSVEESGGRLVTPGTPLTLTCTVSGFSLSN---DVMSWVRQAPGKGLEWIGYIW---SGGSPYYANWAKGRFTISKSSST-
68   QEQLKESGGGLVKPDESLTLTCTASGFSLSS---NGMSWARQAPGKGLEWIGYIY---AGSSPYYANWAKGRFTISKTSST-
91   -QSLEESGGRLVTPGTPLTLTCTVSGSSLYN---YEINWVRQAPGKGLEWIGYID---VGSGTWYASWAKGRFTISKTST--
130  -QSVEESGGRLVTPGTPLTLTCTVSGFSLSS---GVVSWVRQAPGKGLEWIGYAW---SGGATYYASWAKGRFTISKSST--
147  -QSVEESGGRLVTPGTPQTLTCTVSGFSLST---DVVSWVRQAPGKGLEWIGYTW---NGGATYYASWAKGRFTFSKTST--
174  QEQLQESGGGLITPGGTLTLTCTASGFSFNR---NALSWVRQAPGKGLEWIGYIY---SGGSPYYANWAKGRFNVSRTST--
191  -QSVEESGGRLVTPGTPLTLTCTVSGFSLYT---NLINWVRQAPGKGLEWIGYIN---YGASAYYANWAKGRFTISQTSST-
193  -QSVEESGGRLVTPGTPLTLTCTFSGFSLSN---NAINWVRQAPGKGLEWIGYTW---SGGGTYCASWAKGRFTISKTSST-
210  -QSVKESGGRLVTPGGTLTLTCTASGFSLSN---NAMSWVRQAPGKGLEWIGYIY---PGGSPYYANWAKGRFTISRTST--
220  -QSLEESGGRLVTPGTPLTLTCTVSGFSLSK---YEINWVRQAPGKGLEWIGYID---VGSGTWYASWAKGRFTISKTST--
227  -QSLEESGGRLVKPDETLTLTCTVSGFSLYN---YEINWVRQAPGKGLEWIGYID---VGSGTWYASWAKGRFTISRTST--
238  QEQLKESGGGLVTPGGTLTLTCTASGFSLNT---NAMSWVRQAPGKGLEWIGYIY---SGGSPYYANWAKGRFTISRTST--
246  -QSVKESGGGLVTPGGTLTLTCTASGLSLSG---NGMSWVRQAPGKGLEWIGYIY---SGSSPYYASWAKGRFTISKTSST-
256  -QSLEESGGRLVTPGTPLTLTCTVSGFSLSK---YEINWVRQAPGKGLEWIGYID---VGSGTWYASWAKGRFTISKTST--
270  -QSVEESGGRLVTPGTPLTLTCTVSGFSLSS---DVMSWVRQAPGKGLDWIGYIW---SGGRPYYANWAKGRFTISKSSST-
299  -QSLEESGGRLVTPGTPLTLTCTVSGIDLSS---SLMTWVRQAPGKGLEWIGYIW---SGGAPFYASWAKGRFTISKTSST-
318  QDQLKESGGGLVTPGGTLTLTCTASGFSLGS---NGMSWVRQAPGKGLEWIGYIY---SGSSPYYASWAKGRFTISKTST--
327  -QSLEESGGRLVTPGTPLTLTCTVSGFSLSK---YEINWVRQAPGRGLEWIGYID---VGSGTWYASWAKGRFTISKTST--
379  QEQLKESGGDLVKPGASLTLTCTASGFSLIN---IGMSWVRQAPGKGLEWIGYIY---SGGSPYYANWAKGRFTISRTST--
383  -QSLEESGGDLVKPGASLTLTCTASGFSFSR---YVCWVRQAPGKGLEWIGCIA-AGSSGYTYYASWAKGRLTISKTSST-
388  -QSVEESGGRLVTPGTPLTLTCTVSGFSLSS---GVVSWVRQAPGKGLEWIGYAW---SGGPTYYANWAKGRFTISKSST--
408  -QSVEESGGRLVTPGTPLTLTCTVSGFSLST---DVVSWVRQAPGKGLEWIGYTW---NGGATFYASWAKGRFTFSKTST--
411  -QSVEESGGRLVTPGTPLTLTCTVSGFSLSS---GVVSWVRQAPGKGLEWIGYAW---SGGPTYYANWAKGRFTISKSST--
```

```
Figure 1A (Continued):    Heavy Chain Variable Region amino acid alignment

415      -QSVEESGGRLVTPGGSLTLTCTVSGFSLSN--YEMNWVRQAPGKGLEWIGYID---VGSGTWYASWAKGRFTISKTST-
416      -QSVKESGGGLVTPGGTLTLTCTVSGFSLSR--NAMSWVRQTPGKGLEWIGYIY---SGSSPYYANWAKGRFTISRTST-
420      QEQLKESGGGLVTPGGILTLTCTASGFSLRS--NAMSWVRQAPGKGLEWIGYIY---PGGAPHYASWAKGRFTISRNST-
447      QEQLKESGGGLVTPGGILTLTCTASGFSLRS--NAMSWVRQAPGKGLEWIGYIY---PGGAPHYASWAKGRFTISRNST-
476      -QSLEESGGGLVQPEGSPTLTCTAYLIDFSR-YGYMCWVRQAPGKGLEWIGCIH-AGRSGRTYYANWAKGRFTISKTSST
480      -QSLEESGGRLVTPGGSLTLTCTVSGFSLSN--YEINWVRQAPGKGLEWIGYID---VGSGTWYASWAKGRFTISKTST-
547      QEQLKESGGGLVTPGGTLTLTCTASGFSLSS--NGMSWVRQAPGKGLEWIGYIY---SGSSPYYASWAKGRFTISKTSST
565      QEDLKESGGGLITPGGTLTLTCTGSGFSLSS--DGMSWVRQAPGKGLEWIGYIY---SGSSPYYANWAKGRFTISKTSST
EBI-51-1 QEQLEESGGGLVKPEGSLTLTCTASGFDLST--YYYMCWVRQAPGKGLEWIACIYT--GRASTYYATWAKGRFTISKTSST
EBI-51-2 -QSLEESGGRLVTPGTPLTLTCTASGFTIST--DVISWVRQAPGKGLEWIGYTW---SGGSTYYANWAKGRFTLSKTSST
EBI-51-4 -QSVEESGGRLVKPGESLTLTCTASGFSLSS--DVISWVRQAPGKGLEWIGYGW---SGGPTYYANWAKGRFTISKTSST
EBI-51-11 -QSVEESGGRLITPGTPLTLTCTVSGFSLST--DVVSWVRQAPGTGLEWIGYTW---SGGSTYYAIWAKGRFTISKTSST
EBI-51-22 -QSVEESGGRLVTPGTLTLTCTVSGFSLST--DVLSWVRQAPGKGLEWIGYTW---SGGSTYYASWAKGRFTISKTSST
EBI-51-23 -QSVKESEGGLFKPTDTLTLTCTVSGFSLSI--YEISWVRQAPGKELEWIGYIG---VGGVTYYANWAKSRSTITRNTNQ
```

Figure 1A (Continued): Heavy Chain Variable Region amino acid alignment

```
7   -TVDLKMTSLTTEDTATYFCARHLSGGGW-----------YLDIWGPGTLVTVSL
20  -TVDLKMTSLTTEDTATYFCARHASGGGW-----------YLDIWGPGTLVTVSF
23  -TVDLKMTSLTTEDTATYFCARHGSGGGW-----------YLDIWGPGTLVTVSS
37  -TVDLKITSPTTEDTAAYFCARGFGSSGL-----------NIWGPGTLVTVSL
68  -TVDLKVTSLTTEDTATYFCARHASGGGW-----------YLAIWGPGTLVTVSL
91  -TVDLKITSPTTEDTATYFCTRKYNPMD-------------LWGPGTLVTVSS
130 -TVDLKITSPTTADTATYFCARGYNGMD-------------PWGPGTLVTVSS
147 -TVDLKITSPTTEDTATYFCARGYNGMD-------------PWGPGTLVTVSS
174 -TVDLRMTSLTTEDTATYFCARHVSGGGW-----------YLDIWGPGTLVTVSL
191 -TVDLKMTSLTIEDTATYFCARGYNDW-------------DRLDLWGQGTLVTVSS
193 -TVDLKMTSLTTEDTATYFCARAYDSEW-------------DRLDLWGQGTLVTVSS
210 -TVDLKMTSLTTEDTATYFCARHVSDGGW-----------YLYIWGPGTLVTVSL
220 -TVALRITSPTTEDTATYFCSRQYNPMD-------------LWGPGTLVTVSS
227 -TVDLKITSPTTEDTATYFCTRKYNPMD-------------LWGPGTLVTVSS
238 -TVHLKMTSLTTEDTATYFCASHTSGGGW-----------YLDIWGPGTLVTVSL
246 -TVDLKMTSLTTEDTATYFCARHTSGGGW-----------YLDIWGPGTLVTVSL
256 -TVALRITSPTTEDTATYFCSRQYNPMD-------------LWGPGTLVTVSS
270 -TVDLKITSPTTEDTAAYFCARGFGSSGLN-----------IWGPGTLVTVSL
299 -TVDLKMTSLTTEDTATYFCAARYTDSGFDAL---------DPWGPGTLVTVSS
318 -TVDLKMTSLTTEDTATYFCAGHAKGGGW-----------YLDIWGPGTLVTVSL
327 -TVALRITSPTTEDTATYFCSRQYNPMD-------------LWGPGTLVTVSS
379 -TVDLKMTSLTTEDTATYFCARHASDGGW-----------YLDIWGPGTLVTVSL
383 -TLTLQMTSLTVADTATYFCARSGDSYVGYFN---------LWGPGTLVTVSS
388 -TVDLKITSPTTADTATYFCARGYNGMD-------------PWGPGTLVTVSS
408 -TVDLKITSPTTEDTATYFCARGYNGMD-------------PWGPGTLVTVSS
411 -TVDLKITSPTTADTATYFCARGYNGMD-------------PWGPGTLVTVSS
```

Figure 1A (Continued): Heavy Chain Variable Region amino acid alignment

```
415      -TVDLKITSPTTEDTATYFCSRQYNPMD--------------LWGPGTLVTVSS
416      -TVDLKMTSLTTEDTATYFCARHVSDGGW-----------YLDIWGPGTLVAVSL
420      -TVDLKMTSLTTEDTATYFCARHVSGGGW-----------YLDIWGPGTLVTVSL
447      -TVDLKMTSLTTEDTATYFCARHVSGGGW-----------YLDIWGPGTLVTVSL
476      -TVTLQMTSLTAADTATYFCAKSGDSYVGYFA----------LWGPGTLVTVSS
480      -TVDLKITSPTTGDTATYFCSRSYNPMD--------------LWGPGTLVTVSS
547      -TVDLKMTSLTTEDTAKYFCARHVSGGGW-----------YLDIWGPGTLVTVSL
565      -TVDLKMTSLTTEDTATYFCARHLSGGGW-----------YLDIWGPGTLVTVSL
EBI-51-1 -TVTLQMTSLTAADTATFFCASKAGDIWY----------YGMDLWGPGTLVTVSS
EBI-51-2 -TVDLKITSPTIEDTATYFCARGFNPF------------DPWGPGTLVTVSS
EBI-51-4 -TVDLKITSPTTEDTATYFCARGFNPFD------------PWGPGTLVTVSS
EBI-51-11 -TVDLKITSPTTEDTATYFCARGFNPFD------------PWGPGTLVTVSS
EBI-51-22 -TVDLKITSPTTEDTATYFCARGFNPFD------------PWGPGTLVTVSS
EBI-51-23 KMVALKMTSLTAADTATYFCARGYNPFD------------LWGPGTLVTVSS
```

Figure 1B: Light Chain Variable Region amino acid alignment

```
7    ---DMTQTPASVEVAVGGTVTINCQASQNIGS------NLAWYQQKPGQPPKLLIYGASTLAS
20   ------QMCLRHDPDSSLCGGSCGRHSHHQLPGQSEHWFSLVSAETRAASQAPDLWCIH
23   ---DMIQTPASVEVAVGGTVTINCQASQTIGT------NLAWYQQKPGQRPKLLIYAASTLPS
37   ---DMTQTPASVEVAVGGTVTIKCQASQSIGS------NLAWYQQKPGQSPKLLIYSASILAS
68   ---DMTQTPASVEVAVGGTVTIGCQASQSIGS------NLGWYQQKPGQPPKLLIYSASTLAS
91   ---DMTQTPASVEVAVGGTVTIKCQASQNIGS------NLAWYQQKPGQPPKLLIYSTSTVAS
130  ---DMTQTPASVEVAVGGTVTIKCQASQNIGS------NLAWYQQKPGQPPKLLIYKASTLAS
147  ---DMTQTPASVEVAVGGTVTIKCQASQNIGS------NLAWYQQKPGQPPKLLISKASTLAS
174  ---DMIQTPASVEVAVGGTVTINCQASQNIGS------NLAWYQQKPGQPPKLLIYGTSTLAS
191  -IVMTQTPSPVSGAVGGTVTINCQASQSIGS------NLAWYQQKPGQPPKLLIYSASILAS
193  -VMTQTPASVSGPVGGTVTIKCQASQSIGS------NLGWYQQKPGQPPKLLIFSASNLES
210  ---DMTQTPASVEVAVGGTVTIKCQASQSIGS------NLAWYQQKPGQPPKLLIYGASTLAS
220  ---DMTQTPASVEAVGGTVTIKCQASQNIGS------NLAWYQQKPGQRPKLLIYSASTLAS
227  ---DMTQTPASVEAVGGTVTIKCQASQNIGS------NLAWYQQKPGQPPKLLIYSTSTVAS
238  ---DMIQTPASVEVAVGGTVTINCQASQNIGS------NLAWYQQKPGQPPKLLIYGTSTLAS
246  ---DMIQTPASVEVAVGGTVTINCQASQSIGS------NLAWYQQKPGQPPKLLIYSASTLAS
256  ---DMTQTPASVEAAVGGTVTIKCQASQNIGS------NLAWYQQKPGQRPKLLIYSASTLAS
270  ---DMTQTPASVEVAVGGTVTIKCQASQNIGY------NLAWYQQKPGQPPKLLIYGASTLAS
299  ---DMTQTPASVEVAVGGTVTIKCQASQSIGS------YLSWYHQKPGQPPKLLIYRASTLAS
318  ---DMTQTPASVSAAVGGTVTINCQASQSIGS------NLGWYQQKPGQPPKLLIYSASTLAS
327  ---DMTQTPASVEAAVGGTVTIKCQASQNIGS------NLAWYQQKPGQRPKLLIYSASTLAS
379  ---DMIQTPASVEVAVGGTVTINCQASQSIGS------NLAWYQQKPGQPPKLLIYLASTLPS
383  -IVMTQTPASVEAAVGGTVTIKCQASQNIYN------YLAWYQQQPGQPPKLLIYSASNLAS
388  ---DMTQTPASVEVAVGGTVTIKCQASQNIGS------NLAWYQQKPGQPPKLLIYKASTLAS
408  ---DMTQTPASVEAAVGGAVTIKCQASQNIGS------NLAWYHQKPGQPPKLLISKASTLAS
411  ---DMTQTPASVEVAVGGTVTIKCQASQNIGS------NLAWYQQKPGQPPKLLIYKASTLAS
```

Figure 1B (continued): Light Chain Variable Region amino acid alignment

```
415       --DMTQTPASVEVAVGGTVTIKCQASQNIGS---NLAWYQQKPGQRPKLLIYSASTLAS
416       --DMIQTPASVEVVVGGTVTVFNCQASQNIGS---NLAWYQQKPGQPPKLLIYSASTLAS
420       --DMIQTPASVEVGVGGTVTINCQASQNIGS---NLAWYQQKPGQPPKFLIYGASTLAS
447       --DMIQTPASVEVGVGGTVTINCQASQNIGS---NLAWYQQKPGQPPKFLIYGASTLAS
476       DIVMTQTPASVEAAVGGTVTIKCQASENIYN---YLSWYQQKPGQPPKLLIYEASKLAS
480       --DMTQTPASVEVAVGGTVTIKCQASQNIGS---NLAWYQQKPGQRPKLLIYSASTLAS
547       --DMIQTPASVEVAVGGTVTINCQASQSIGS---NLAWYQQKPGQRPKLLIYGASTLAS
565       --DMIQTPASVSEPVGGTVTINCQASQNIGS---NLAWYQQKPGQPSKLLIYKASTLAS
EBI-51-1  --DMTQTPASVSEPVGGTVTIKCQASQNIGS---NLAWYQQKPGQRPKLLIYRASTLAS
EBI-51-2  --DMIQTPASVSEPVGGTVTIVCQASQNIGS---NFAWYQQKPGQPPKLLIYRASTLAS
EBI-51-4  --DMIQTPASVSEPVGGTVTIKCQASQNIGS---NLAWYQQKPGQRPKLLIYRASTLAS
EBI-51-11 --DMTQTPASVSEPVGGTVTIKCQASQNIGS---NLAWYQQKPGQPPKLLIYRASTLAS
EBI-51-22 --DMTQTPASVSDPVGGTVTIKCQASQNIGS---NLAWYQQKPGQRPKLLIYRASTLAS
EBI-51-23 --DMTQTPASVEVAVGGTVTINCQASQNIGS---NLAWYQQKPGQPPKLLIYKASTLAS
```

Figure 1B (continued):    Light Chain Variable Region amino acid alignment

```
  7   GVSSRFKGSGSGTQFTFTISDVECTDPATYYCQQAYSISNVD--NPFGGGTEVVVK
 20   SGIWGLI--AVQRQWIWDTVHFHHQRRGVYRCCHLLSTGICACRCFRRRDRDGGQ
 23   GVSSRFKGSGSGTQFTLTISDVECSDAATYYCQQAYSVGNVD--NAFGGGTEVVVK
 37   GVPSRFKGSGSGTQFTLTISGVQCDDAATYYCQQGYSVGNID--NAFGGGTEVVVK
 68   GVSSRFKGSGSGTEFTLTISDVECDDAATYYCQQAYSVSNVD--NAFGGGTEVVVK
 91   GVPSRFKGSGFGTQFTLTISGVQCDDAATYYCQQGYSAGNVN--NPFGGGTEVVVK
130   GVPSRFRGSGSGTEFTLAISDLECADAATYYCQQGYTTKDLV--NPFGGGTEVVVK
147   GVPSRFKGSGSGTEFTLAISDLECADAATYYCQQGYTTKNVV--NPFGGGTEVVVK
174   GVSSRFKGSGFGTQFTFTISDVECTDAATYYCQQAYSISNVD--NAFGGGTEVVVK
191   GAPSRVSGSGYGTEFTLTISGVQCADAATYYCQQGYTTNADN---IFGGGTEVVVE
193   GVPSRFKGSGSGTQFTLTISDLECDDAATYYCQQGYTTNNVL--NAFAGGTEVVVK
210   GVPSRFKGSGSGTQFTFTISDVECTAAATYYCQQAYSISNVD--NAFGGGTEVVVK
220   GVPSRFKGSGSGTQFTLTISGVQCDDAATYYCQQGYSVGNVN--NAFGGGTEVVVK
227   GVPSRFKGSGFGTQFTLTISGVQCDDAATYYCQQGYSAGNVN--NPFGGGTEVVVK
238   GVSSRFKGSGFGTQFTFTISDVECTDAATYYCQQAYSTSKID--NAFGGGTEVVVK
246   GVSSRFKGSGSGTDYTLTISDVECTDAATYYCQQAYSISNVE--NPFGGGTEVVVK
256   GVPSRFKGSGSGTQFTLTISGVQCDDAATYYCQQGYSVGNVN--NAFGGGTEVVVK
270   GVPSRFKGSGSGTQFTLTISGVQCDDAATYYCQQGYSVSNID--NAFGGGTEVVVK
299   GVPSRFKGSGSGTEFTLTISDLECADAATYYCQQGYSANVDN---AFGGGTEVVVK
318   GVSSRFKGSGSGTHFAFTISDVECTDAATYYCQQAYSVGNVD--NAFGGGTEVVVK
327   GVPSRFKGSGSGTQFTLTISGVQCDDAATYYCQQGYSVGNVN--NAFGGGTEVVVK
379   GVPSRFKGSGSGTEFTLTISDVECTDAATYYCQQAYTASNVD--NAFGGGTEVVVK
383   GVSSRFKGSGSGTEFTLTISDLECGDAATYYCQSYYDSSRISYGSAFGGGTEVVVK
388   GVPSRFRGSGSGTEFTLAISDLECADAATYYCQQGYTTKDVV--NPFGGGTEVVVK
408   GVPSRFKGSGSGTEFTLAISDLECADAATYYCQQGYTTKNVV--NPFGGGTEVVVK
411   GVPSRFRGSGSGTEFTLAISDLECADAATYYCQQGYTTKDVV--NPFGGGTEVVVK
```

Figure 1B (continued): Light Chain Variable Region amino acid alignment

```
415       GVPSRFKGSGSGTQFTLTISGVQCDDAATYYCQQGYSVGNVN--NAFGGGTEVVVK
416       GVPSRFKGSGSGTQFTFTISDVECTDAATYYCQQAYSISNVD--NAFGGGTEVVVK
420       GVSSRFKGSGSGTRFTFTISDVECTDAATYYCQQAYSVGNVD--NAFGGGTEVVVK
447       GVSSRFKGSGSGTRFTFTISDVECTDAATYYCQQAYSVGNVD--NAFGGGTEVVVK
476       GVSSRFKGSGSGTEFTLTISDLECADAATYYCQSYYDVTSHSYDNPFGGGTEVVVS
480       GVPSRFKGSGSGTQFTLTISGVQCDDAATYYCQQGYSVGNVN--NAFGGGTEVVVK
547       GVSSRVKGSGSGTQFTFTISDVECTDAATYYCQQAYSISNVD--NAFGGGTEVVVK
565       GVPSRFKGSGSGTDFTLTISDLECADAATYYCQQAYTISNVD--NAFGGGTEVVVK
EBI-51-1  GVSSRFKGSGSGTQFTLTISDLECADAATYYCQQGYSAGNVD--NNTFGGGTEVVVK
EBI-51-2  GVSSRFKGSGFGTQFTLTISDLECADAATYYCQQGYSAGNVD--NNFGGGTEVVVK
EBI-51-4  GVSSRFKGSGSGTQFTLTISDLECADAATYYCQQGYSAGNVD--NSFGGGTEVVVK
EBI-51-11 GVSSRFKGSGSGTQFTLTISDLECADAATYYCQQGYSAGNVDK-HVFGGGTEVVVK
EBI-51-22 GVSSRFKGSGSGTQFTLTISDLECADAATYYCQQGYSAGNVDN-NAFGGGTEVVVK
EBI-51-23 GVPSRLKGSGSGTEFTLTISGVQCDDAATYYCQQGYTTGNVD--NPFGGGTEVVVK
```

Figure 1C: Rabbit anti-RANKL antibody clone 23 humanization: amino acid alignment Clone 23 HEAVY CHAIN

```
                                                  CDR1                              CDR2
23H       QEQLKESGGGLVTPGGTLTLTCTASGFSLSSDGMSWVRQAPGKGLEWIGYIYSGSSPYYANWAKGRFTISKTSS
23HZD-2   EVQLVESGGGLVQPGGSLRLSCAASGFSLSSNGMSWVRQAPGKGLEWIGYIYSGSSPYYANWAKGRFTISKDSS
23HZD-1 HC EVQLVESGGGLVQPGGSLRLSCAASGFSLSSDGMSWVRQAPGKGLEWIGYIYSGSSPYYANWAKGRFTISKDSS
H23N VH   QEQLVESGGGLVQPGGSLRLSCVASGFSLSSDGMSWVRQAPGKGLEWIGYIYSGSSPYYANWAKGRFTISKDSS
```

Clone 23 HEAVY CHAIN (continued)

```
                                  CDR3
23H       -TTVDLKMTSLTTEDTATYFCARHGSGGGWYLDIWGPGTLVTVSS
23HZD-2   KNTVYLQMNSLRAEDTAVYFCARHGSGGGWYLDIWGPGTLVTVSS
23HZD-1 HC KNTVYLQMNSLRAEDTAVYFCARHGSGGGWYLDIWGPGTLVTVSS
H23N VH   TNTVFLQMNSLRAEDTAVYFCARHGDGGGWYLDIWGPGTLVTVSS
```

Figure 1C (continued): Rabbit anti-RANKL antibody clone 23 humanization: amino acid alignment Clone 23 LIGHT CHAIN

```
                                       CDR1                            CDR2
23L       AYDMIQTPASVEVAVGGTVTINCQASQTIGTNLAWYQQKPGQRPKLLIYAASTLPS
23LHZD    DIQMTQSPSSLSASVGDRVTINCQASQTIGTNLAWYQQKPGKRPKLLIYAASTLPS
23LHZD_b  DIQMTQSPSSLSASVGDRVTINCQASQSIGSNLAWYQQKPGKRPKLLIYAASTLPS
H23N VL   DIQMTQSPSSLSASVGDRVTINCQASQSIGSNLAWYQQKPGKAPKLLIYAASTLPS
```

Clone 23 LIGHT CHAIN (Continued)

```
                                                    CDR3
23L       GVSSRFKGSGSGTQFTLTISDVECSDAATYYCQQAYSVGNVDNAFGGGTEVVVK
23LHZD    GVPSRFSGSGSGTDFTLTISSLQPEDFATYYCQQAYSVGNVDNAFGGGTKVEIK
23LHZD_b  GVPSRFSGSGSGTDFTLTISSLQPEDFATYYCQQAYSVGNVDNAFGGGTKVEIK
H23N VL   GVSSRFSGSGSGTDFTLTINSLEAEDAATYYCQQAYSVGNVDNAFGGGTKVEIK
```

Figure 1D: Rabbit anti-RANKL antibody clone 408 humanization: amino acid alignment Clone 408 HEAVY CHAIN

```
                                         CDR1                                    CDR2
408H    -QSVEESGGRLVTPGTPLTLTCTVSGFSLSTDVVSWVRQAPGKGLEWIGYTWNGGATFYASWAKGRFTFSKTST-
HZD408H EVQLVESGGGLVQPGGSLRLSCAVSGFSLSTDVVSWVRQAPGKGLEWIGYTWNGGATFYASWAKGRFTFSKDSSK
```

Clone 408 HEAVY CHAIN (continued)

```
                                                     CDR3
408H    -TVDLKITSPTTEDTATYFCARGYNGMDPWGPGTLVTVSS
HZD408H NTVYLQMNSPRAEDTAVYFCARGYNGMDPWGPGTLVTVSS
```

Figure 1D (continued): Rabbit anti-RANKL antibody clone 408 humanization: amino acid alignment Clone 408 LIGHT CHAIN

```
                      CDR1                               CDR2
408L     AYDMTQTPASVEAAVGGAVTIKCQASQNIGSNLAWYHQKPGQPPKLLISKASTLAS
HZD 408L DIQMTQSPSSLSASVGDRVTIKCQASQNIGSNLAWYQQKPGKPPKLLISKASTLAS
```

Clone 408 LIGHT CHAIN (continued)

```
                                            CDR3
408L     GVPSRFKGSGSGTEFTLAISDLECADAATYYCQQGYTTKNVVNPFGGGTEVVVK
HZD 408L GVPSRFSGSGSGTDFTLTISSLQPEDFATYYCQQGYTTKNVVNPFGGGTKVEIK
```

Figure 1E: Rabbit anti-RANKL antibody clone EBI51-22 humanization: amino acid alignment Clone EBI-51-22 HEAVY CHAIN

```
                           CDR1                                               CDR2
EBI51-22H     -QSVEESGGRLVTPGTLLTLTCTVSGFSLSTDVLSWVRQAPGKGLEWIGYTWSGGSTYYASWAKGRFTISKTSS
HZDEBI51-22H  EVQLVESGGGLVQPGGSLRLSCAVSGFSLSTDVLSWVRQAPGKGLEWIGYTWSGGSTYYASWAKGRFTISKDSS
```

Clone EBI-51-22 HEAVY CHAIN (continued)

```
                                        CDR3
EBI51-22H     -TTVDLKITSPTTEDTATYFCARGFNPFDPWGPGTLVTVSS
HZDEBI51-22H  KNTVYLQMNSPRAEDTAVYFCARGFNPFDPWGPGTLVTVSS
```

Figure 1E (continued): Rabbit anti-RANKL antibody clone EBI51-22 humanization: amino acid alignment Clone EBI-51-22 LIGHT CHAIN

```
                                    CDR1                           CDR2
EBI51-22H      AYDMTQTPASVSDPVGGTVTIKCQASQNIGSNLAWYQQKPGQRPKLLIYRASTLAS
HZDEBI51-22L   DIQMTQSPSSLSASVGDRVTIKCQASQNIGSNLAWYQQKPGKRPKLLIYRASTLAS
```

Clone EBI-51-22 LIGHT CHAIN (continued)

```
                                                   CDR3
EBI51-22H      GVSSRFKGSGSGTQFTLTISDLECADAATYYCQQGYSAGNVDNNAFGGGTEVVVK
HZDEBI51-22L   GVPSRFSGSGSGTDFTLTISSLQPEDFATYYCQQGYSAGNVDNNAFGGGTKVEIK
```

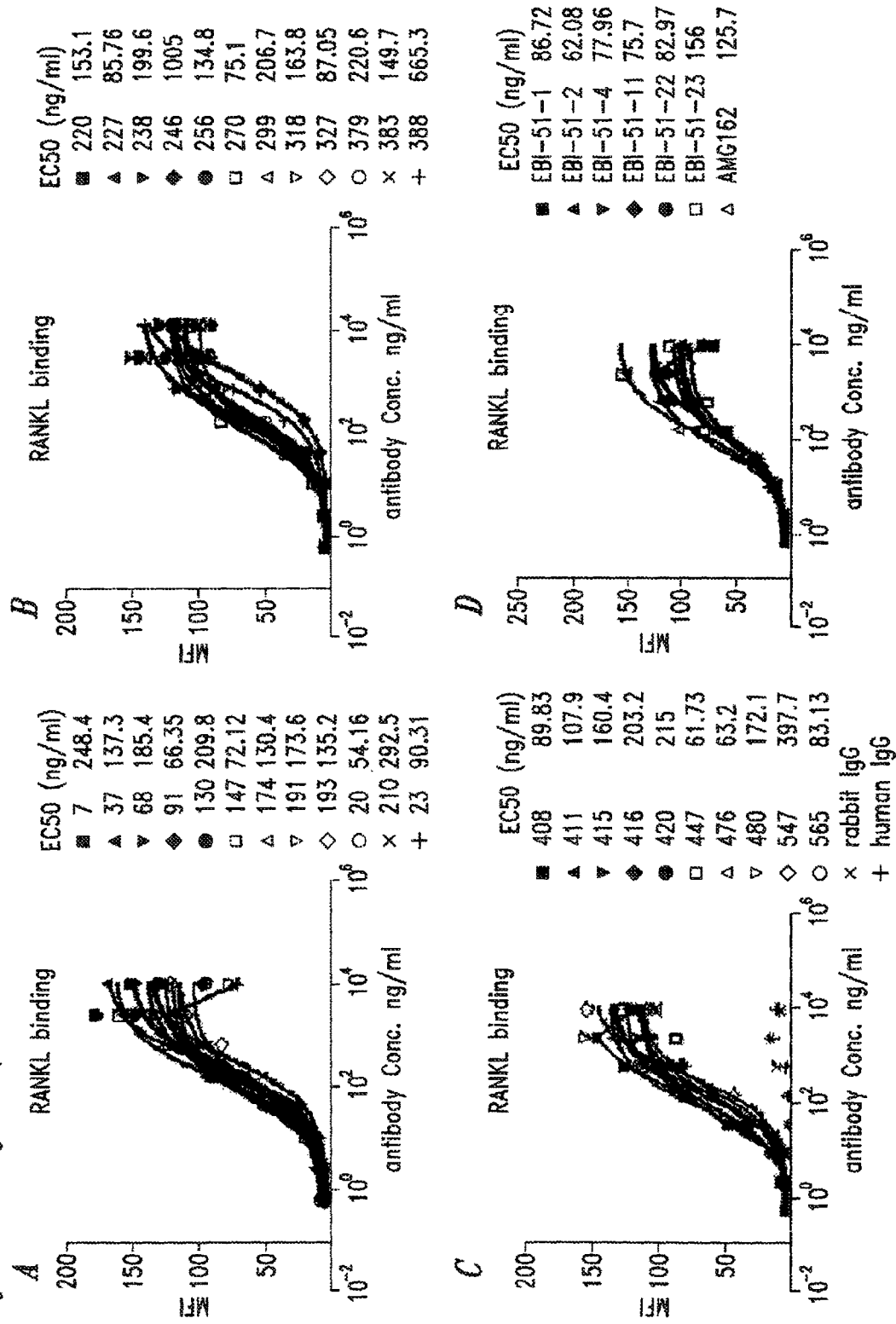
Figure 2: Binding affinity of Anti-RANKL antibodies

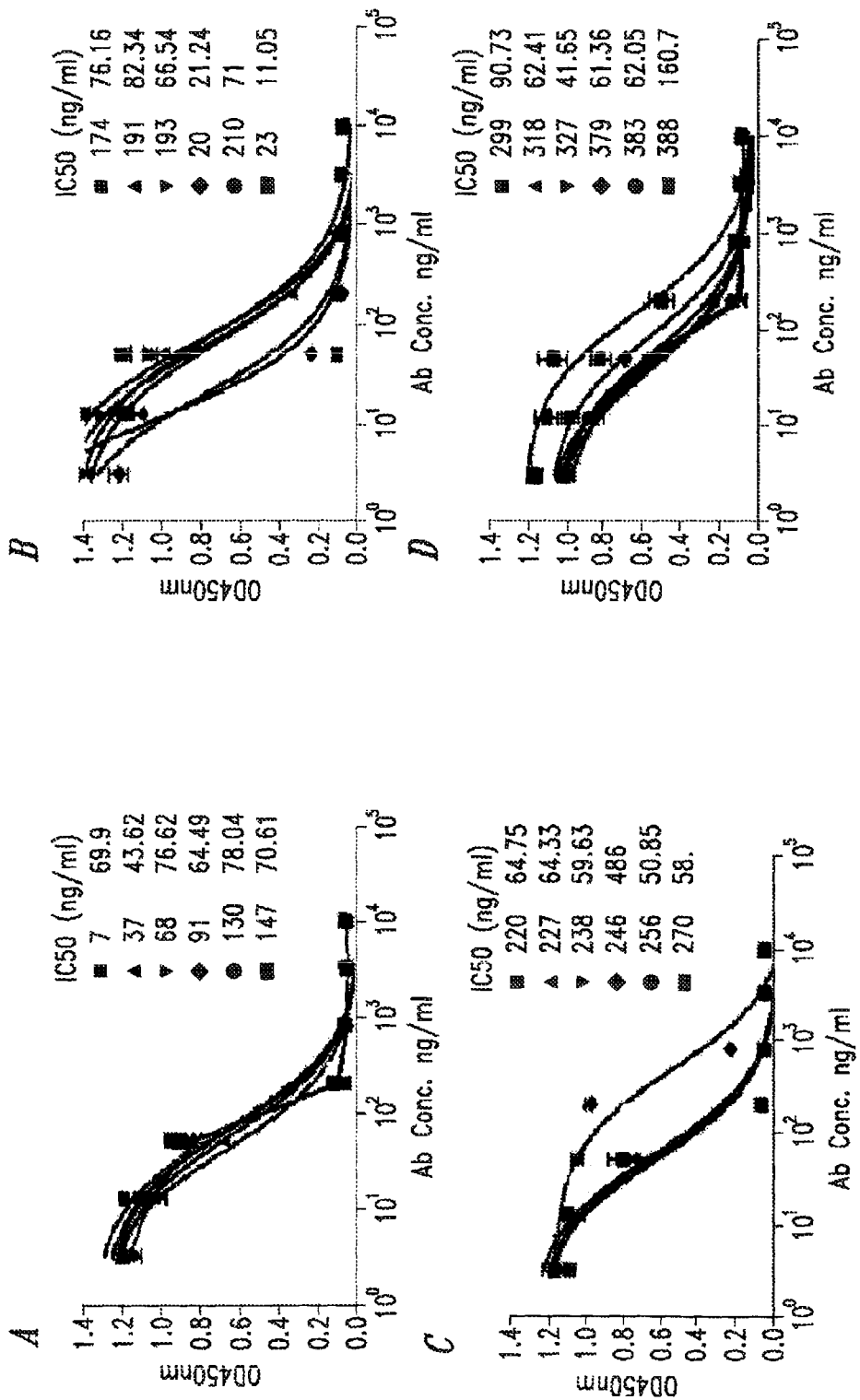
Figure 3: Inhibition of RANKL binding to its receptor by Anti-RANKL antibodies

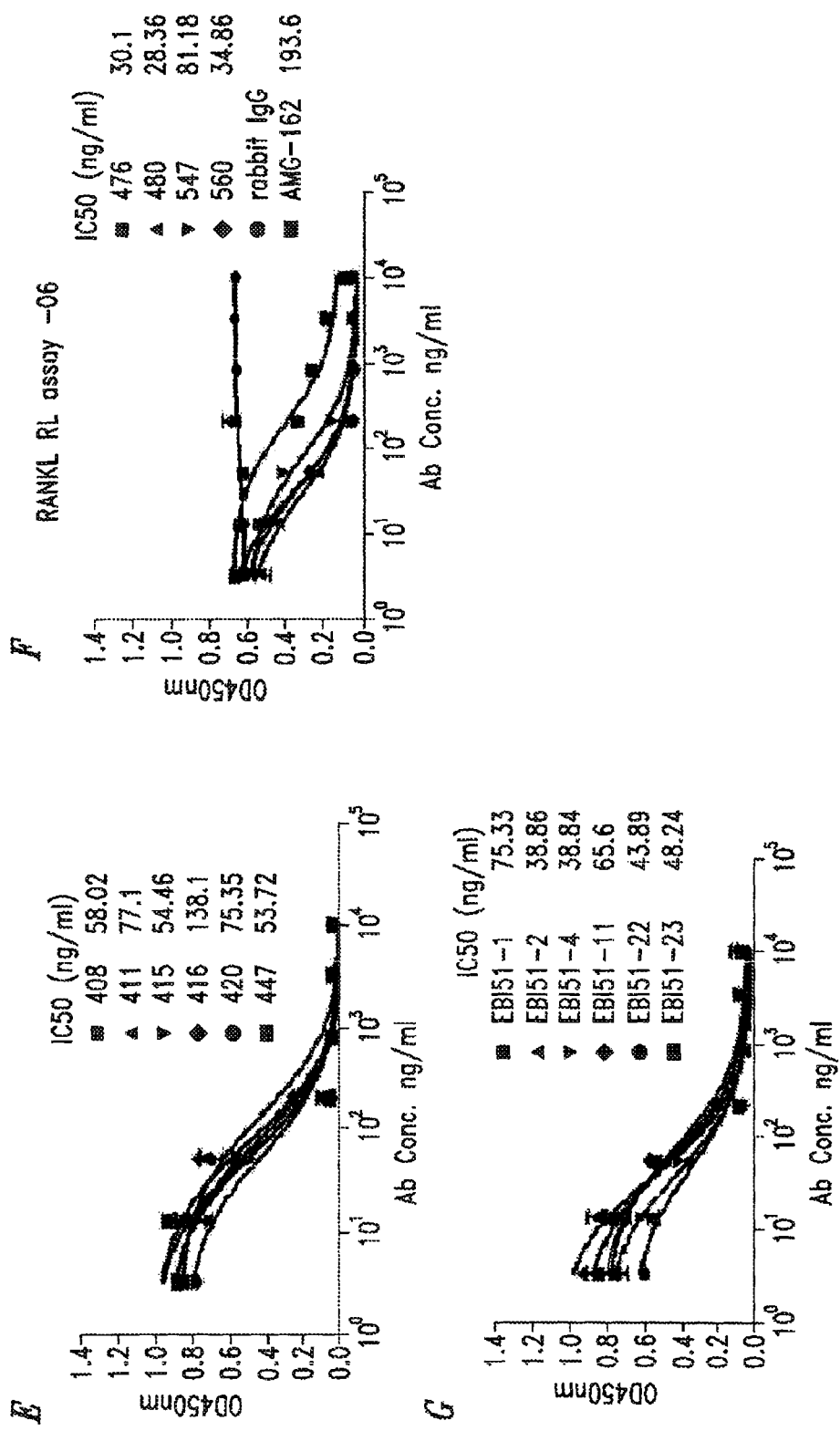
Figure 3: Inhibition of RANKL binding to its receptor by Anti-RANKL antibodies

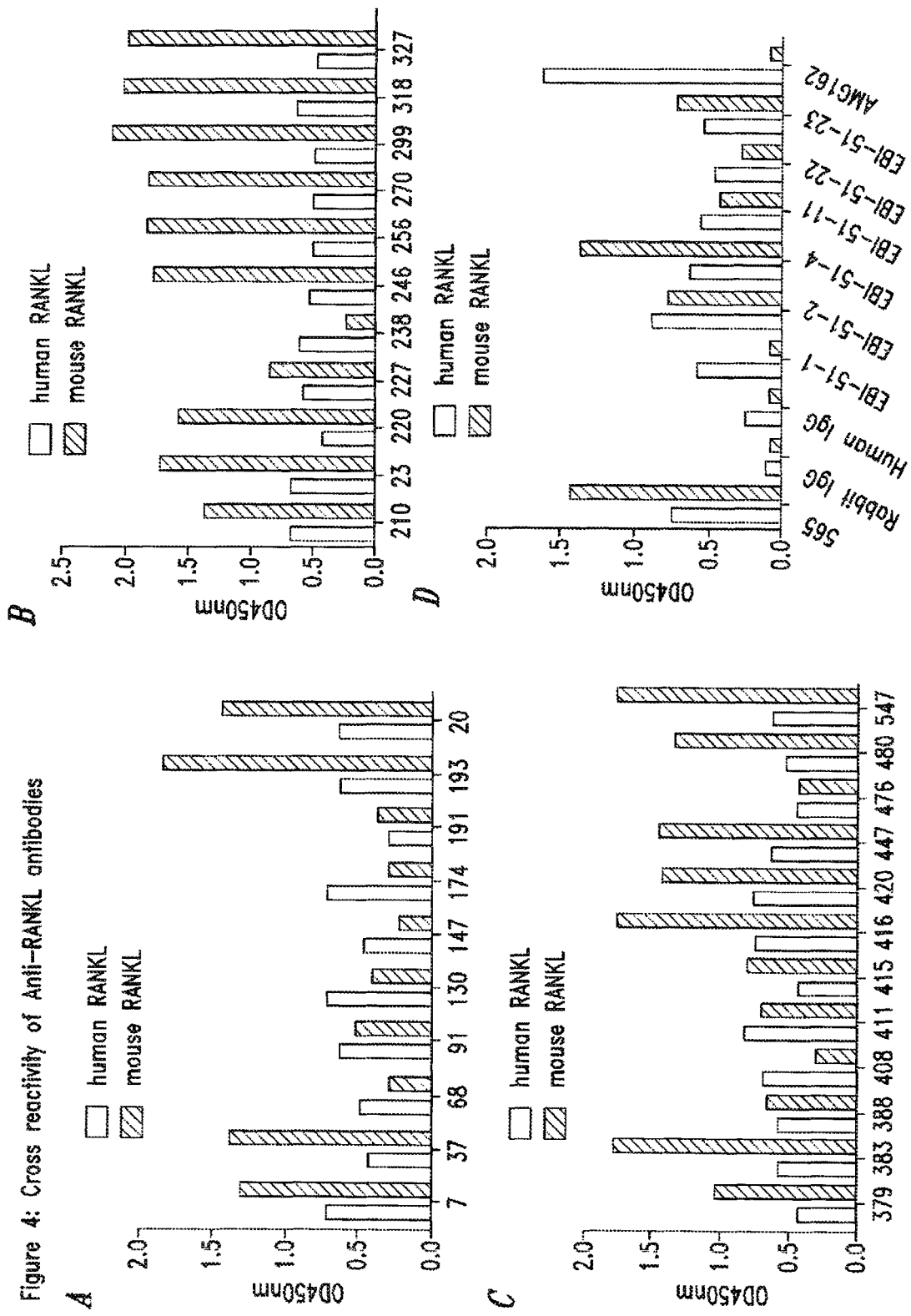

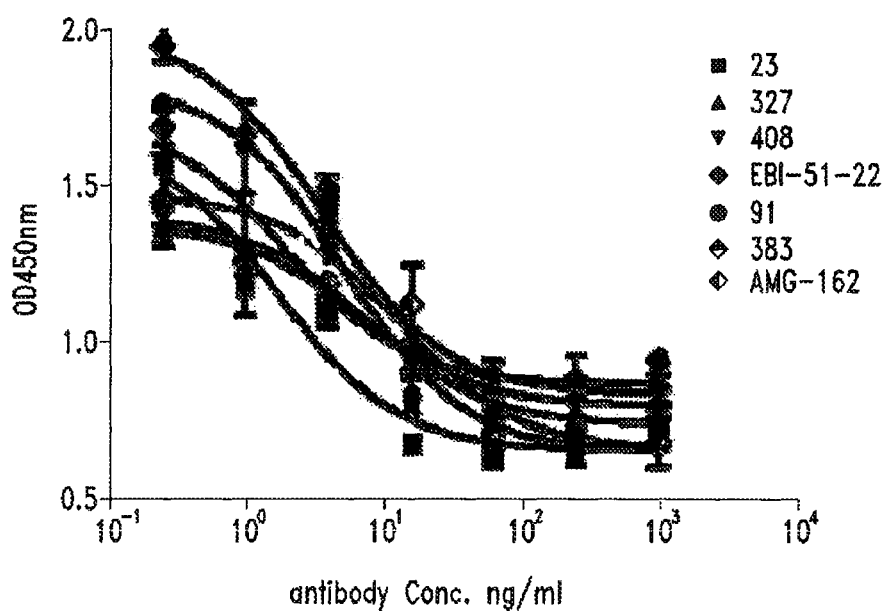
Figure 5: Inhibition of osteoclast cell differentiation induced by RANKL

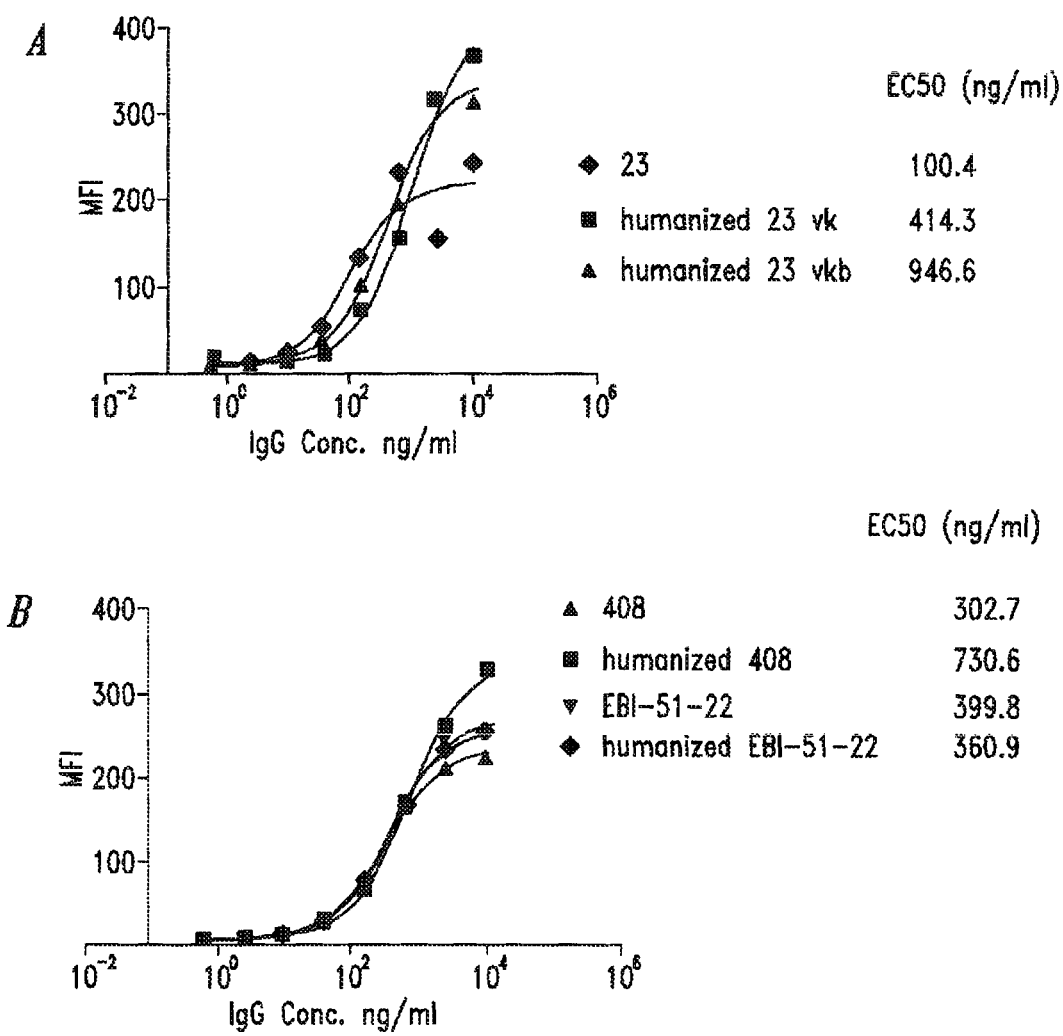
Figure 6. Humanized 23 and 408 Bind to Cell Surface RANKL

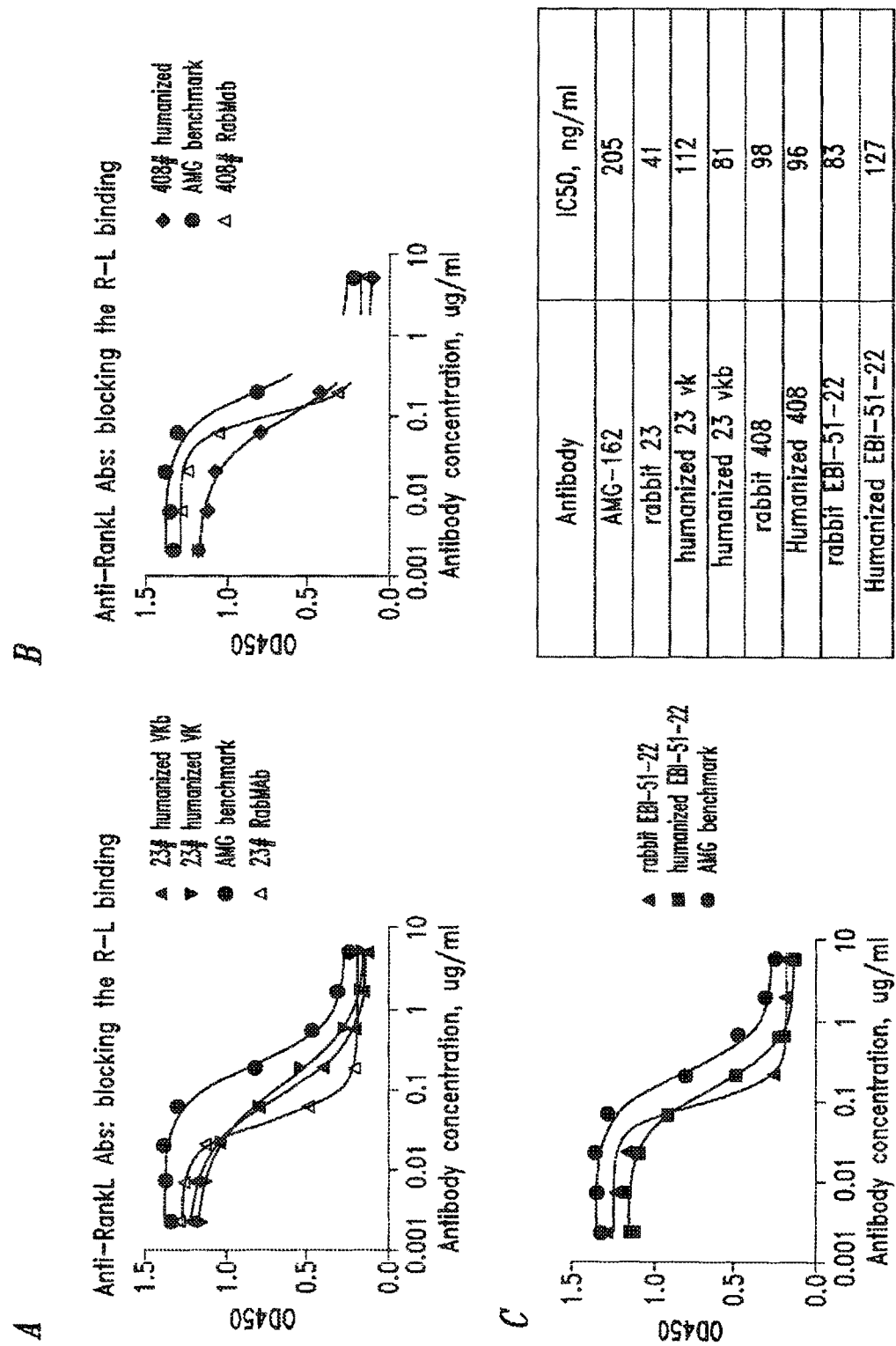

Figure 8: Humanized anti-RANKL antibodies inhibit osteoclast cell differentiation
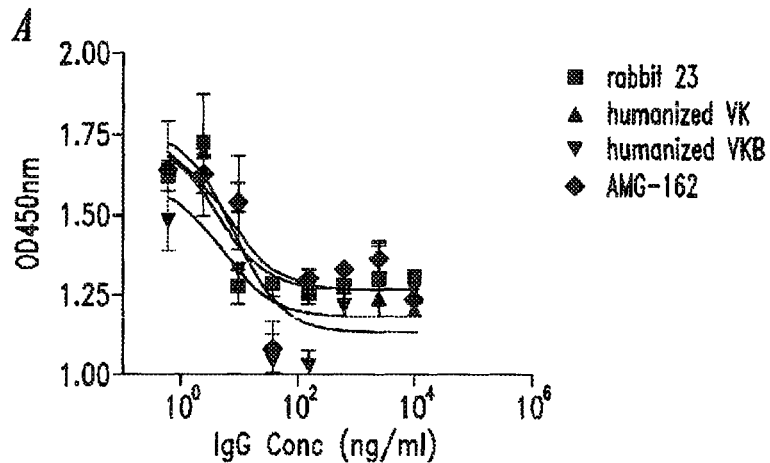
|  | IC50, ng/ml | Ratio (Ab/AMG-162) |
|---|---|---|
| rabbit 23 | 3.697 | 0.56 |
| humanized 23VK | 7.926 | 1.20 |
| humanized 23VKB | 5.163 | 0.78 |
| AMG-162 | 6.579 | 1.00 |
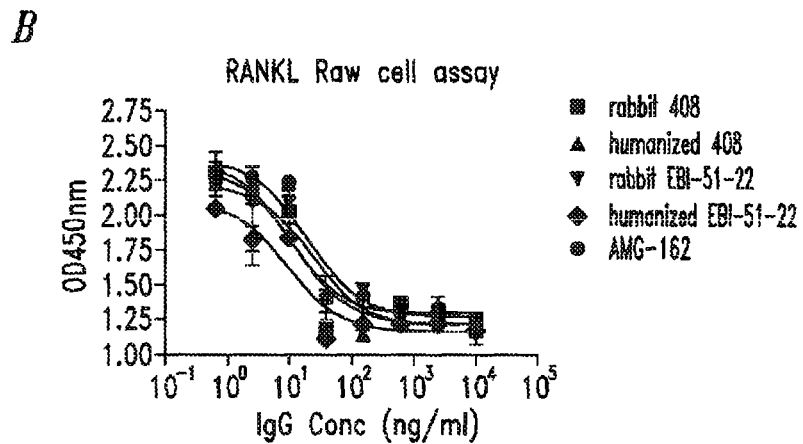
|  | IC50, ng/ml | Ratio (Ab/AMG-162) |
|---|---|---|
| rabbit 408 | 9.35 | 0.50 |
| humanized 408 | 22.81 | 1.22 |
| rabbit EBI-51-22 | 12.62 | 0.67 |
| humanized EBI-51-22 | 9.557 | 0.51 |
| AMG-162 | 18.72 | 1.00 |

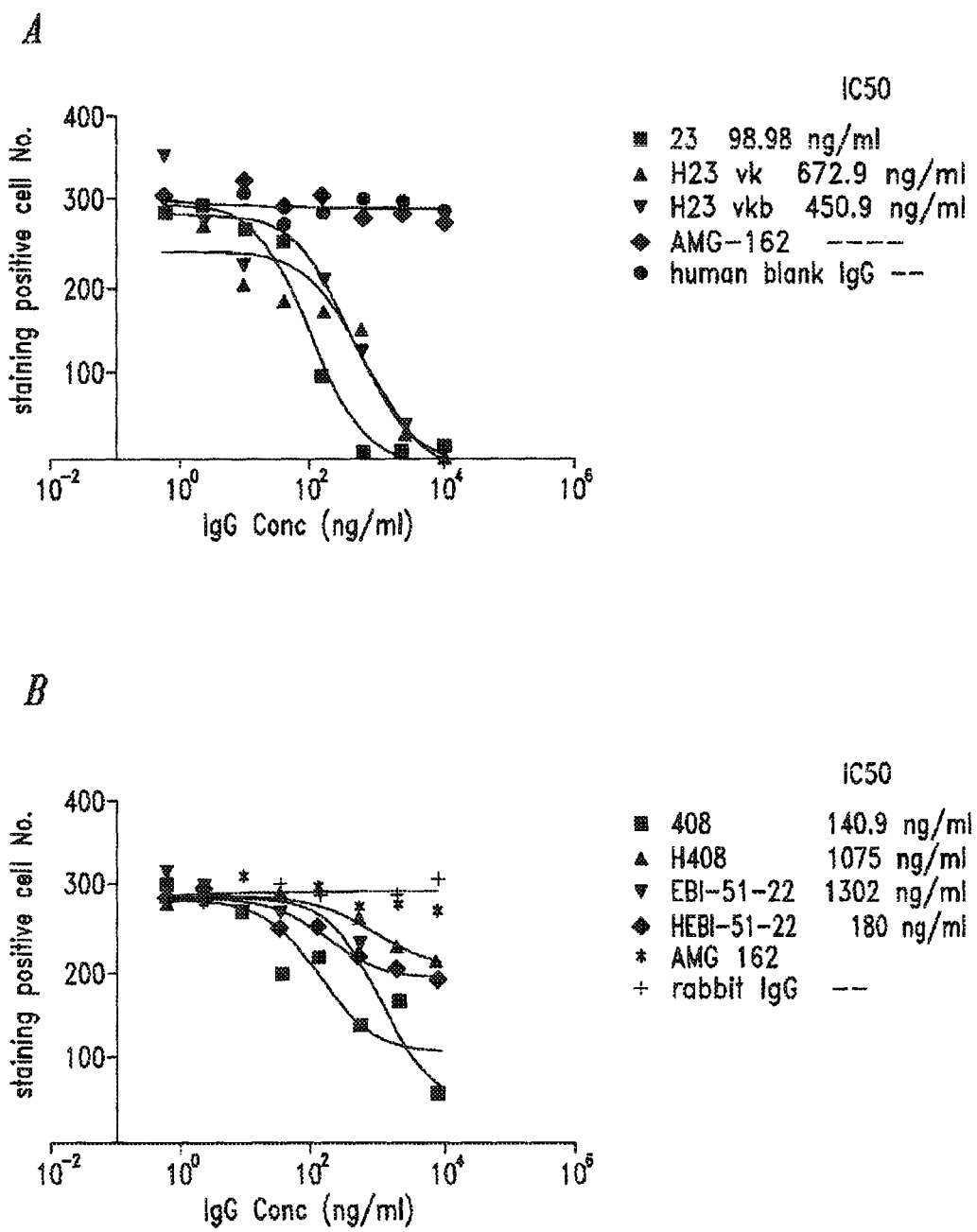
Figure 9: Inhibition of Mouse RANKL-induced Raw Cell Differentiation in vitro

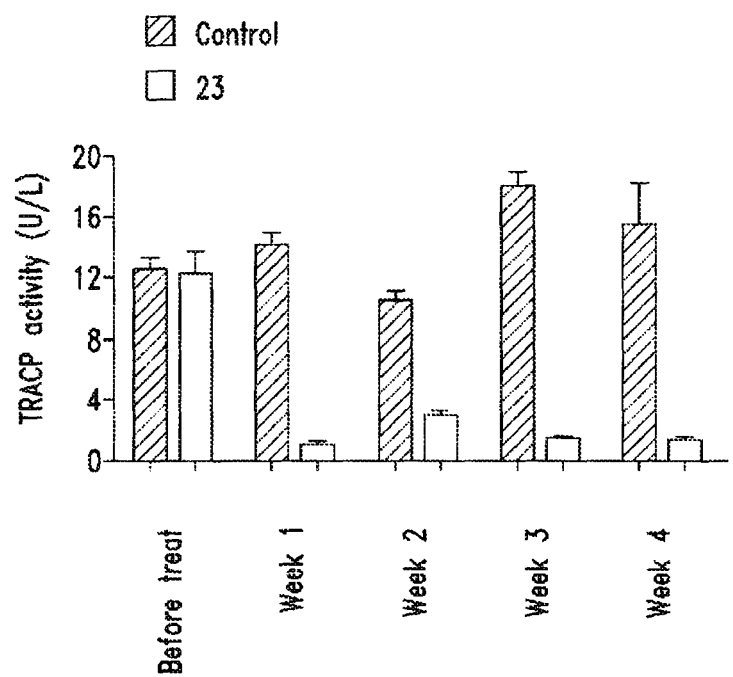
Figure 10: Anti-RANKL Antibody significantly inhibited Osteoclast activity in vivo

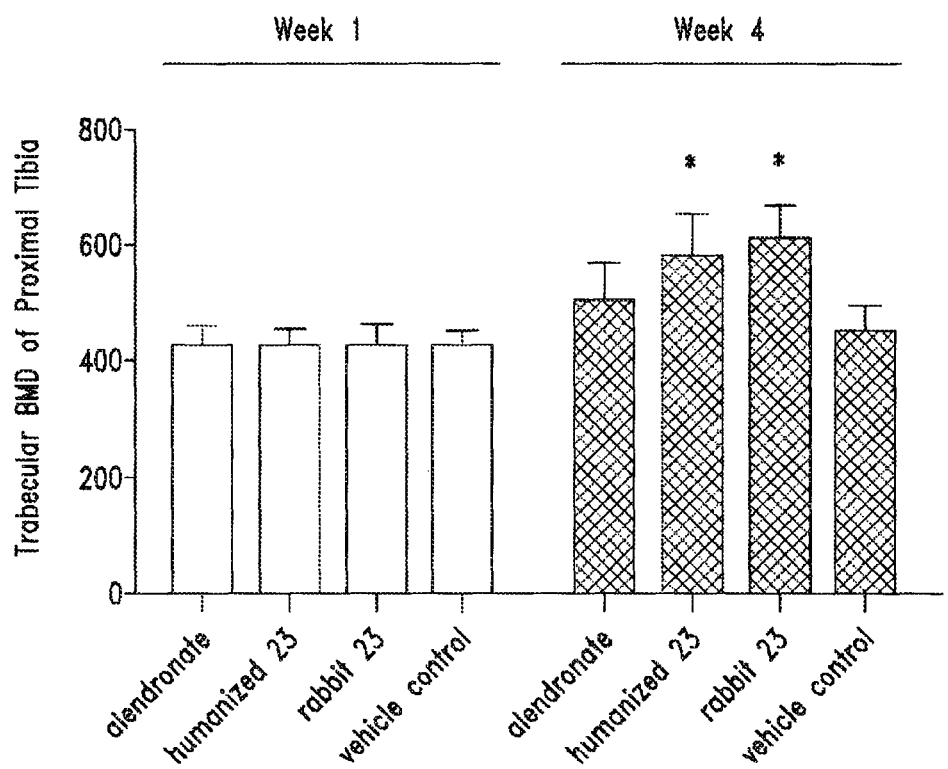
Figure 11: Anti-RANKL Antibody significantly increased bone density in OVX mice

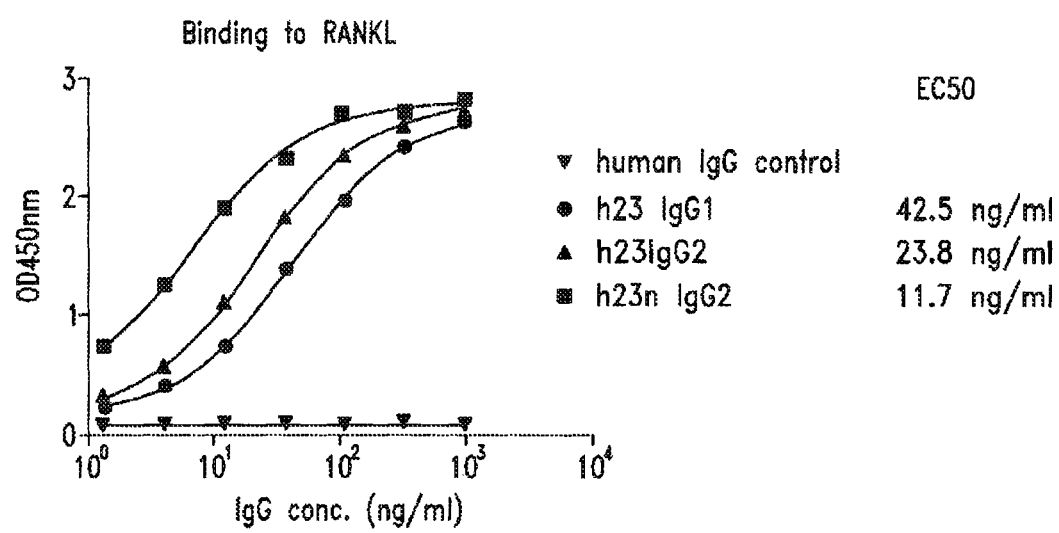
Figure 12: Comparison of h23n IgG2 humanized version of clone 23 with other clone 23 humanized versions

SEQUENCE LISTING

```
<160> NUMBER OF SEQ ID NOS: 235

<210> SEQ ID NO 1
<211> LENGTH: 118
<212> TYPE: PRT
<213> ORGANISM: Oryctolagus cuniculus

<400> SEQUENCE: 1

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Ser Leu Ser Ser Asp
            20                  25                  30

Gly Met Ser Trp Val Arg Gln Ala Pro Gly Lys Gly Leu Glu Trp Ile
        35                  40                  45

Gly Tyr Ile Tyr Ser Gly Ser Ser Pro Tyr Tyr Ala Asn Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

His Gly Ser Gly Gly Gly Trp Tyr Leu Asp Ile Trp Gly Pro Gly Thr
            100                 105                 110

Leu Val Thr Val Ser Ser
        115

<210> SEQ ID NO 2
<211> LENGTH: 110
<212> TYPE: PRT
<213> ORGANISM: Oryctolagus cuniculus
```

```
<400> SEQUENCE: 2

Ala Tyr Asp Met Ile Gln Thr Pro Ala Ser Val Glu Val Ala Val Gly
1               5                   10                  15

Gly Thr Val Thr Ile Asn Cys Gln Ala Ser Gln Thr Ile Gly Thr Asn
            20                  25                  30

Leu Ala Trp Tyr Gln Gln Lys Pro Gly Gln Arg Pro Lys Leu Leu Ile
        35                  40                  45

Tyr Ala Ala Ser Thr Leu Pro Ser Gly Val Ser Ser Arg Phe Lys Gly
    50                  55                  60

Ser Gly Ser Gly Thr Gln Phe Thr Leu Thr Ile Ser Asp Val Glu Cys
65                  70                  75                  80

Ser Asp Ala Ala Thr Tyr Tyr Cys Gln Gln Ala Tyr Ser Val Gly Asn
                85                  90                  95

Val Asp Asn Ala Phe Gly Gly Gly Thr Glu Val Val Val Lys
            100                 105                 110

<210> SEQ ID NO 3
<211> LENGTH: 5
<212> TYPE: PRT
<213> ORGANISM: Oryctolagus cuniculus

<400> SEQUENCE: 3

Ser Asp Gly Met Ser
1               5

<210> SEQ ID NO 4
<211> LENGTH: 16
<212> TYPE: PRT
<213> ORGANISM: Oryctolagus cuniculus

<400> SEQUENCE: 4

Tyr Ile Tyr Ser Gly Ser Ser Pro Tyr Tyr Ala Asn Trp Ala Lys Gly
1               5                   10                  15

<210> SEQ ID NO 5
<211> LENGTH: 11
<212> TYPE: PRT
<213> ORGANISM: Oryctolagus cuniculus

<400> SEQUENCE: 5

His Gly Ser Gly Gly Gly Trp Tyr Leu Asp Ile
1               5                   10

<210> SEQ ID NO 6
<211> LENGTH: 11
<212> TYPE: PRT
<213> ORGANISM: Oryctolagus cuniculus

<400> SEQUENCE: 6

Gln Ala Ser Gln Thr Ile Gly Thr Asn Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Ala Ala Ser Thr Leu Pro Ser
1               5
```

```
<210> SEQ ID NO 8
<211> LENGTH: 12
<212> TYPE: PRT
<213> ORGANISM: Oryctolagus cuniculus

<400> SEQUENCE: 8

Gln Gln Ala Tyr Ser Val Gly Asn Val Asp Asn Ala
1               5                   10

<210> SEQ ID NO 9
<211> LENGTH: 119
<212> TYPE: PRT
<213> ORGANISM: Artificial Sequence
<220> FEATURE:
<223> OTHER INFORMATION: Humanized VH rabbit anti-RANKL antibody clone
      23

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asp
            20                  25                  30

Gly Met Ser Trp Val Arg Gln Ala Pro Gly Lys Gly Leu Glu Trp Ile
        35                  40                  45

Gly Tyr Ile Tyr Ser Gly Ser Ser Pro Tyr Tyr Ala Asn Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg His Gly Ser Gly Gly Gly Trp Tyr Leu Asp Ile Trp Gly Pro Gly
            100                 105                 110

Thr Leu Val Thr Val Ser Ser
        115

<210> SEQ ID NO 10
<211> LENGTH: 110
<212> TYPE: PRT
<213> ORGANISM: Artificial Sequence
<220> FEATURE:
<223> OTHER INFORMATION: Humanized VL rabbit anti-RANKL antibody clone
      23

<400> SEQUENCE: 10

Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Thr Ile Gly Thr Asn
            20                  25                  30

Leu Ala Trp Tyr Gln Gln Lys Pro Gly Lys Arg Pro Lys Leu Leu Ile
        35                  40                  45

Tyr Ala Ala Ser Thr Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Val Gly Asn
                85                  90                  95

Val Asp Asn Ala Phe Gly Gly Gly Thr Lys Val Glu Ile Lys
            100                 105                 110

<210> SEQ ID NO 11
```

<211> LENGTH: 110
<212> TYPE: PRT
<213> ORGANISM: Artificial Sequence
<220> FEATURE:
<223> OTHER INFORMATION: Humanized VL rabbit anti-RANKL antibody clone 23

<400> SEQUENCE: 11

Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Gly Ser Asn
            20                  25                  30

Leu Ala Trp Tyr Gln Gln Lys Pro Gly Lys Arg Pro Lys Leu Leu Ile
        35                  40                  45

Tyr Ala Ala Ser Thr Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Val Gly Asn
                85                  90                  95

Val Asp Asn Ala Phe Gly Gly Gly Thr Lys Val Glu Ile Lys
            100                 105                 110

<210> SEQ ID NO 12
<211> LENGTH: 119
<212> TYPE: PRT
<213> ORGANISM: Artificial Sequence
<220> FEATURE:
<223> OTHER INFORMATION: Humanized VH rabbit anti-RANKL antibody clone 23

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Gly Met Ser Trp Val Arg Gln Ala Pro Gly Lys Gly Leu Glu Trp Ile
        35                  40                  45

Gly Tyr Ile Tyr Ser Gly Gly Ser Pro Tyr Tyr Ala Asn Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg His Gly Gly Gly Gly Trp Tyr Leu Asp Ile Trp Gly Pro Gly
            100                 105                 110

Thr Leu Val Thr Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: Humanized VHCDR1 rabbit anti-RANKL antibody clone 23

<400> SEQUENCE: 13

Ser Asn Gly Met Ser
1               5

```
<210> SEQ ID NO 14
<211> LENGTH: 17
<212> TYPE: PRT
<213> ORGANISM: Artificial Sequence
<220> FEATURE:
<223> OTHER INFORMATION: Humanized VHCDR2 rabbit anti-RANKL antibody
      clone 23

<400> SEQUENCE: 14

Tyr Ile Tyr Ser Gly Gly Ser Pro Tyr Tyr Ala Asn Trp Ala Lys Gly
1               5                   10                  15

Arg

<210> SEQ ID NO 15
<211> LENGTH: 11
<212> TYPE: PRT
<213> ORGANISM: Artificial Sequence
<220> FEATURE:
<223> OTHER INFORMATION: Humanized VLCDR1 rabbit anti-RANKL antibody
      clone 23

<400> SEQUENCE: 15

Gln Ala Ser Gln Ser Ile Gly Ser Asn Leu Ala
1               5                   10

<210> SEQ ID NO 16
<211> LENGTH: 118
<212> TYPE: PRT
<213> ORGANISM: Oryctolagus cuniculus

<400> SEQUENCE: 16

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Ser Leu Thr Thr Asn
                20                  25                  30

Gly Met Ser Trp Val Arg Gln Ala Pro Gly Lys Gly Leu Glu Trp Ile
            35                  40                  45

Gly Tyr Ile Tyr Ser Gly Gly Ser Pro Tyr Tyr Ala Asn Trp Ala Lys
        50                  55                  60

Gly Arg Phe Thr Ile Ser Lys Thr Ser Ser Thr Val Asp Leu Lys
65                  70                  75                  80

Met Thr Ser Leu Thr Thr Glu Asp Thr Ala Thr Tyr Phe Cys Ala Arg
                85                  90                  95

His Leu Ser Gly Gly Gly Trp Tyr Leu Asp Ile Trp Gly Pro Gly Thr
            100                 105                 110

Leu Val Thr Val Ser Leu
        115

<210> SEQ ID NO 17
<211> LENGTH: 118
<212> TYPE: PRT
<213> ORGANISM: Oryctolagus cuniculus

<400> SEQUENCE: 17

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Tyr Leu Ser Ser Asn
                20                  25                  30

Gly Met Ser Trp Val Arg Gln Ala Pro Gly Lys Gly Leu Glu Trp Ile
            35                  40                  45
```

Gly Tyr Ile Tyr Ser Gly Gly Ser Pro Tyr Tyr Ala Ser Trp Ala Lys
            50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

His Ala Ser Gly Gly Gly Trp Tyr Leu Asp Ile Trp Gly Pro Gly Thr
            100                 105                 110

Leu Val Thr Val Ser Phe
            115

<210> SEQ ID NO 18
<211> LENGTH: 115
<212> TYPE: PRT
<213> ORGANISM: Oryctolagus cuniculus

<400> SEQUENCE: 18

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Asp Val
            20                  25                  30

Met Ser Trp Val Arg Gln Ala Pro Gly Lys Gly Leu Glu Trp Ile Gly
        35                  40                  45

Tyr Ile Trp Ser Gly Gly Ser Pro Tyr Tyr Ala Asn Trp Ala Lys Gly
    50                  55                  60

Arg Phe Thr Ile Ser Lys Ser Ser Ser Thr Thr Val Asp Leu Lys Ile
65                  70                  75                  80

Thr Ser Pro Thr Thr Glu Asp Thr Ala Ala Tyr Phe Cys Ala Arg Gly
                85                  90                  95

Phe Gly Ser Ser Gly Leu Asn Ile Trp Gly Pro Gly Thr Leu Val Thr
            100                 105                 110

Val Ser Leu
        115

<210> SEQ ID NO 19
<211> LENGTH: 118
<212> TYPE: PRT
<213> ORGANISM: Oryctolagus cuniculus

<400> SEQUENCE: 19

Gln Glu Gln Leu Lys Glu Ser Gly Gly Gly Leu Val Lys Pro Asp Glu
1               5                   10                  15

Ser Leu Thr Leu Thr Cys Thr Ala Ser Gly Phe Ser Leu Ser Ser Asn
            20                  25                  30

Gly Met Ser Trp Ala Arg Gln Ala Pro Gly Lys Gly Leu Glu Trp Ile
        35                  40                  45

Gly Tyr Ile Tyr Ala Gly Ser Ser Pro Tyr Tyr Ala Asn Trp Ala Lys
    50                  55                  60

Gly Arg Phe Thr Ile Ser Lys Thr Ser Ser Thr Thr Val Asp Leu Lys
65                  70                  75                  80

Val Thr Ser Leu Thr Thr Glu Asp Thr Ala Thr Tyr Phe Cys Ala Arg
                85                  90                  95

His Ala Ser Gly Gly Gly Trp Tyr Leu Ala Ile Trp Gly Pro Gly Thr
            100                 105                 110

Leu Val Thr Val Ser Leu
            115

<210> SEQ ID NO 20
<211> LENGTH: 112
<212> TYPE: PRT
<213> ORGANISM: Oryctolagus cuniculus

<400> SEQUENCE: 20

Gln Ser Leu Glu Glu Ser Gly Gly Arg Leu Val Lys Pro Asp Glu Thr
1               5                   10                  15

Leu Thr Leu Thr Cys Thr Val Ser Gly Ser Ser Leu Tyr Asn Tyr Glu
                20                  25                  30

Ile Asn Trp Val Arg Gln Ala Pro Gly Lys Gly Leu Glu Trp Ile Gly
            35                  40                  45

Tyr Ile Asp Val Gly Ser Gly Thr Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Thr Arg Lys Tyr
                85                  90                  95

Asn Pro Met Asp Leu Trp Gly Pro Gly Thr Leu Val Thr Val Ser Ser
                100                 105                 110

<210> SEQ ID NO 21
<211> LENGTH: 112
<212> TYPE: PRT
<213> ORGANISM: Oryctolagus cuniculus

<400> SEQUENCE: 21

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Gly Val
                20                  25                  30

Val Ser Trp Val Arg Gln Ala Pro Gly Lys Gly Leu Glu Trp Ile Gly
            35                  40                  45

Tyr Ala Trp Ser Gly Gly Ala Thr Tyr Tyr Ala Ser Trp Ala Lys Gly
    50                  55                  60

Arg Phe Thr Ile Ser Lys Ser Ser Thr Thr Val Asp Leu Lys Ile Thr
65                  70                  75                  80

Ser Pro Thr Thr Ala Asp Thr Ala Thr Tyr Phe Cys Ala Arg Gly Tyr
                85                  90                  95

Asn Gly Met Asp Pro Trp Gly Pro Gly Thr Leu Val Thr Val Ser Ser
                100                 105                 110

<210> SEQ ID NO 22
<211> LENGTH: 112
<212> TYPE: PRT
<213> ORGANISM: Oryctolagus cuniculus

<400> SEQUENCE: 22

Gln Ser Val Glu Glu Ser Gly Gly Arg Leu Val Thr Pro Gly Thr Pro
1               5                   10                  15

Gln Thr Leu Thr Cys Thr Val Ser Gly Phe Ser Leu Ser Thr Asp Val
                20                  25                  30

Val Ser Trp Val Arg Gln Ala Pro Gly Lys Gly Leu Glu Trp Ile Gly
            35                  40                  45

Tyr Thr Trp Asn Gly Gly Ala Thr Tyr Tyr Ala Ser Trp Ala Lys Gly
    50                  55                  60

Arg Phe Thr Phe Ser Lys Thr Ser Thr Thr Val Asp Leu Lys Ile Thr

```
            65                  70                  75                  80
Ser Pro Thr Thr Glu Asp Thr Ala Thr Tyr Phe Cys Ala Arg Gly Tyr
                85                  90                  95

Asn Gly Met Asp Pro Trp Gly Pro Gly Thr Leu Val Thr Val Ser Ser
            100                 105                 110

<210> SEQ ID NO 23
<211> LENGTH: 117
<212> TYPE: PRT
<213> ORGANISM: Oryctolagus cuniculus

<400> SEQUENCE: 23

Gln Glu Gln Leu Gln Glu Ser Gly Gly Gly Leu Ile Thr Pro Gly Gly
1               5                   10                  15

Thr Leu Thr Leu Thr Cys Thr Ala Ser Gly Phe Ser Phe Asn Arg Asn
            20                  25                  30

Ala Leu Ser Trp Val Arg Gln Ala Pro Gly Lys Gly Leu Glu Trp Ile
        35                  40                  45

Gly Tyr Ile Tyr Ser Gly Gly Ser Pro Tyr Tyr Ala Asn Trp Ala Lys
    50                  55                  60

Gly Arg Phe Asn Val Ser Arg Thr Ser Thr Thr Val Asp Leu Arg Met
65                  70                  75                  80

Thr Ser Leu Thr Thr Glu Asp Thr Ala Thr Tyr Phe Cys Ala Arg His
                85                  90                  95

Val Ser Gly Gly Gly Trp Tyr Leu Asp Ile Trp Gly Pro Gly Thr Leu
            100                 105                 110

Val Thr Val Ser Leu
        115

<210> SEQ ID NO 24
<211> LENGTH: 117
<212> TYPE: PRT
<213> ORGANISM: Oryctolagus cuniculus

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Tyr Thr Asn Leu
            20                  25                  30

Ile Asn Trp Val Arg Gln Ala Pro Gly Lys Gly Leu Glu Trp Ile Gly
        35                  40                  45

Tyr Ile Asn Tyr Gly Ala Ser Ala Tyr Tyr Ala Asn Trp Ala Lys Gly
    50                  55                  60

Arg Phe Thr Ile Ser Gln Thr Ser Ser Thr Thr Val Asp Leu Lys Met
65                  70                  75                  80

Thr Ser Leu Thr Ile Glu Asp Thr Ala Thr Tyr Phe Cys Ala Arg Gly
                85                  90                  95

Tyr Gly Asn Asp Trp Asp Arg Leu Asp Leu Trp Gly Gln Gly Thr Leu
            100                 105                 110

Val Thr Val Ser Ser
        115

<210> SEQ ID NO 25
<211> LENGTH: 117
<212> TYPE: PRT
<213> ORGANISM: Oryctolagus cuniculus

<400> SEQUENCE: 25
```

-continued

```
Gln Ser Val Glu Glu Ser Gly Gly Arg Leu Val Thr Gly Thr Pro
1               5                   10                  15

Leu Thr Leu Thr Cys Thr Phe Ser Gly Phe Ser Leu Ser Asn Asn Ala
                20                  25                  30

Ile Asn Trp Val Arg Gln Ala Pro Gly Lys Gly Leu Glu Trp Ile Gly
            35                  40                  45

Tyr Thr Trp Ser Gly Gly Thr Tyr Cys Ala Ser Trp Ala Lys Gly
        50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Ala
                85                  90                  95

Tyr Asp Ser Glu Trp Asp Arg Leu Asp Leu Trp Gly Gln Gly Thr Leu
            100                 105                 110

Val Thr Val Ser Ser
            115

<210> SEQ ID NO 26
<211> LENGTH: 116
<212> TYPE: PRT
<213> ORGANISM: Oryctolagus cuniculus

<400> SEQUENCE: 26

Gln Ser Val Lys Glu Ser Gly Gly Gly Leu Val Thr Pro Gly Gly Thr
1               5                   10                  15

Leu Thr Leu Thr Cys Thr Ala Ser Gly Phe Ser Leu Ser Asn Asn Ala
                20                  25                  30

Met Ser Trp Val Arg Gln Ala Pro Gly Lys Gly Leu Glu Trp Ile Gly
            35                  40                  45

Tyr Ile Tyr Pro Gly Gly Ser Pro Tyr Tyr Ala Asn Trp Ala Lys Gly
        50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg His Val
                85                  90                  95

Ser Asp Gly Gly Trp Tyr Leu Tyr Ile Trp Gly Pro Gly Thr Leu Val
            100                 105                 110

Thr Val Ser Leu
        115

<210> SEQ ID NO 27
<211> LENGTH: 112
<212> TYPE: PRT
<213> ORGANISM: Oryctolagus cuniculus

<400> SEQUENCE: 27

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Lys Tyr Glu
                20                  25                  30

Ile Asn Trp Val Arg Gln Ala Pro Gly Lys Gly Leu Glu Trp Ile Gly
            35                  40                  45

Tyr Ile Asp Val Gly Ser Gly Thr Trp Tyr Ala Ser Trp Ala Lys Gly
        50                  55                  60

Arg Phe Thr Ile Ser Lys Thr Ser Thr Thr Val Ala Leu Arg Ile Thr
65                  70                  75                  80
```

Ser Pro Thr Thr Glu Asp Thr Ala Thr Tyr Phe Cys Ser Arg Gln Tyr
                85                  90                  95

Asn Pro Met Asp Leu Trp Gly Pro Gly Thr Leu Val Thr Val Ser Ser
            100                 105                 110

<210> SEQ ID NO 28
<211> LENGTH: 112
<212> TYPE: PRT
<213> ORGANISM: Oryctolagus cuniculus

<400> SEQUENCE: 28

Gln Ser Leu Glu Glu Ser Gly Gly Arg Leu Val Lys Pro Asp Glu Thr
1               5                   10                  15

Leu Thr Leu Thr Cys Thr Val Ser Gly Phe Ser Leu Tyr Asn Tyr Glu
                20                  25                  30

Ile Asn Trp Val Arg Gln Ala Pro Gly Lys Gly Leu Glu Trp Ile Gly
            35                  40                  45

Tyr Ile Asp Val Gly Ser Gly Thr Trp Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Thr Arg Lys Tyr
                85                  90                  95

Asn Pro Met Asp Leu Trp Gly Pro Gly Thr Leu Val Thr Val Ser Ser
            100                 105                 110

<210> SEQ ID NO 29
<211> LENGTH: 117
<212> TYPE: PRT
<213> ORGANISM: Oryctolagus cuniculus

<400> SEQUENCE: 29

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Ser Leu Asn Thr Asn
                20                  25                  30

Ala Met Ser Trp Val Arg Gln Ala Pro Gly Lys Gly Leu Glu Trp Ile
            35                  40                  45

Gly Tyr Ile Tyr Ser Gly Gly Ser Pro Tyr Tyr Ala Asn Trp Ala Lys
        50                  55                  60

Gly Arg Phe Thr Ile Ser Arg Thr Ser Thr Thr Val His Leu Lys Met
65                  70                  75                  80

Thr Ser Leu Thr Thr Glu Asp Thr Ala Thr Tyr Phe Cys Ala Ser His
                85                  90                  95

Thr Ser Gly Gly Gly Trp Tyr Leu Asp Ile Trp Gly Pro Gly Thr Leu
            100                 105                 110

Val Thr Val Ser Leu
            115

<210> SEQ ID NO 30
<211> LENGTH: 117
<212> TYPE: PRT
<213> ORGANISM: Oryctolagus cuniculus

<400> SEQUENCE: 30

Gln Ser Val Lys Glu Ser Gly Gly Gly Leu Val Thr Pro Gly Gly Thr
1               5                   10                  15

Leu Thr Leu Thr Cys Thr Ala Ser Gly Leu Ser Leu Ser Gly Asn Gly
            20                  25                  30

Met Ser Trp Val Arg Gln Ala Pro Gly Lys Gly Leu Glu Trp Ile Gly
        35                  40                  45

Tyr Ile Tyr Ser Gly Ser Ser Pro Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg His
                85                  90                  95

Thr Ser Gly Gly Gly Trp Tyr Leu Asp Ile Trp Gly Pro Gly Thr Leu
            100                 105                 110

Val Thr Val Ser Leu
        115

<210> SEQ ID NO 31
<211> LENGTH: 112
<212> TYPE: PRT
<213> ORGANISM: Oryctolagus cuniculus

<400> SEQUENCE: 31

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Lys Tyr Glu
            20                  25                  30

Ile Asn Trp Val Arg Gln Ala Pro Gly Lys Gly Leu Glu Trp Ile Gly
        35                  40                  45

Tyr Ile Asp Val Gly Ser Gly Thr Trp Tyr Ala Ser Trp Ala Lys Gly
    50                  55                  60

Arg Phe Thr Ile Ser Lys Thr Ser Thr Thr Val Ala Leu Arg Ile Thr
65                  70                  75                  80

Ser Pro Thr Thr Glu Asp Thr Ala Thr Tyr Phe Cys Ser Arg Gln Tyr
                85                  90                  95

Asn Pro Met Asp Leu Trp Gly Pro Gly Thr Leu Val Thr Val Ser Ser
            100                 105                 110

<210> SEQ ID NO 32
<211> LENGTH: 115
<212> TYPE: PRT
<213> ORGANISM: Oryctolagus cuniculus

<400> SEQUENCE: 32

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Val
            20                  25                  30

Met Ser Trp Val Arg Gln Ala Pro Gly Lys Gly Leu Asp Trp Ile Gly
        35                  40                  45

Tyr Ile Trp Ser Gly Gly Arg Pro Tyr Tyr Ala Asn Trp Ala Lys Gly
    50                  55                  60

Arg Phe Thr Ile Ser Lys Ser Ser Ser Thr Thr Val Asp Leu Lys Ile
65                  70                  75                  80

Thr Ser Pro Thr Thr Glu Asp Thr Ala Ala Tyr Phe Cys Ala Arg Gly
                85                  90                  95

Phe Gly Ser Ser Gly Leu Asn Ile Trp Gly Pro Gly Thr Leu Val Thr
            100                 105                 110

Val Ser Leu
        115

<210> SEQ ID NO 33
<211> LENGTH: 118
<212> TYPE: PRT
<213> ORGANISM: Oryctolagus cuniculus

<400> SEQUENCE: 33

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Ser Leu
            20                  25                  30

Met Thr Trp Val Arg Gln Ala Pro Gly Lys Gly Leu Glu Trp Ile Gly
        35                  40                  45

Tyr Ile Trp Ser Gly Gly Ala Pro Phe Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Thr Glu Asp Thr Ala Thr Tyr Phe Cys Ala Ala Arg
                85                  90                  95

Tyr Thr Asp Ser Gly Phe Asp Ala Leu Asp Pro Trp Gly Pro Gly Thr
            100                 105                 110

Leu Val Thr Val Ser Ser
        115

<210> SEQ ID NO 34
<211> LENGTH: 118
<212> TYPE: PRT
<213> ORGANISM: Oryctolagus cuniculus

<400> SEQUENCE: 34

Gln Asp Gln Leu Lys Glu Ser Gly Gly Gly Leu Val Thr Pro Gly Gly
1               5                   10                  15

Thr Leu Thr Leu Thr Cys Thr Ala Ser Gly Phe Ser Leu Gly Ser Asn
            20                  25                  30

Gly Met Ser Trp Val Arg Gln Ala Pro Gly Lys Gly Leu Glu Trp Ile
        35                  40                  45

Gly Tyr Ile Tyr Ser Gly Ser Ser Pro Tyr Tyr Ala Ser Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Gly
                85                  90                  95

His Ala Lys Gly Gly Gly Trp Tyr Leu Asp Ile Trp Gly Pro Gly Thr
            100                 105                 110

Leu Val Thr Val Ser Leu
        115

<210> SEQ ID NO 35
<211> LENGTH: 112
<212> TYPE: PRT
<213> ORGANISM: Oryctolagus cuniculus

<400> SEQUENCE: 35

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Lys Tyr Glu

```
                        20                  25                  30
Ile Asn Trp Val Arg Gln Ala Pro Gly Lys Gly Leu Glu Trp Ile Gly
                35                  40                  45

Tyr Ile Asp Val Gly Ser Gly Thr Trp Tyr Ala Ser Trp Ala Lys Gly
        50                  55                  60

Arg Phe Thr Ile Ser Lys Thr Ser Thr Thr Val Ala Leu Arg Ile Thr
65                  70                  75                  80

Ser Pro Thr Thr Glu Asp Thr Ala Thr Tyr Phe Cys Ser Arg Gln Tyr
                85                  90                  95

Asn Pro Met Asp Leu Trp Gly Pro Gly Thr Leu Val Thr Val Ser Ser
                100                 105                 110

<210> SEQ ID NO 36
<211> LENGTH: 117
<212> TYPE: PRT
<213> ORGANISM: Oryctolagus cuniculus

<400> SEQUENCE: 36

Gln Glu Gln Leu Lys Glu Ser Gly Gly Gly Leu Val Thr Pro Gly Gly
1               5                   10                  15

Thr Leu Thr Leu Thr Cys Thr Ala Ser Arg Phe Ser Leu Ile Asn Ile
                20                  25                  30

Gly Met Ser Trp Val Arg Gln Ala Pro Gly Arg Gly Leu Glu Trp Ile
                35                  40                  45

Gly Tyr Ile Tyr Ser Gly Gly Ser Pro Tyr Tyr Ala Asn Trp Ala Lys
        50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Ala Arg His
                85                  90                  95

Ala Ser Asp Gly Gly Trp Tyr Leu Asp Ile Trp Gly Pro Gly Thr Leu
                100                 105                 110

Val Thr Val Ser Leu
        115

<210> SEQ ID NO 37
<211> LENGTH: 118
<212> TYPE: PRT
<213> ORGANISM: Oryctolagus cuniculus

<400> SEQUENCE: 37

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Arg Tyr Val
                20                  25                  30

Cys Trp Val Arg Gln Ala Pro Gly Lys Gly Leu Glu Trp Ile Gly Cys
                35                  40                  45

Ile Ala Ala Gly Ser Ser Gly Tyr Thr Tyr Tyr Ala Ser Trp Ala Lys
        50                  55                  60

Gly Arg Leu Thr Ile Ser Lys Thr Ser Ser Thr Thr Leu Thr Leu Gln
65                  70                  75                  80

Met Thr Ser Leu Thr Val Ala Asp Thr Ala Thr Tyr Phe Cys Ala Arg
                85                  90                  95

Ser Gly Asp Ser Tyr Val Gly Tyr Phe Asn Leu Trp Gly Pro Gly Thr
                100                 105                 110

Leu Val Thr Val Ser Ser
```

<210> SEQ ID NO 38
<211> LENGTH: 112
<212> TYPE: PRT
<213> ORGANISM: Oryctolagus cuniculus

<400> SEQUENCE: 38

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Gly Val
            20                  25                  30

Val Ser Trp Val Arg Gln Ala Pro Gly Lys Gly Leu Glu Trp Ile Gly
        35                  40                  45

Tyr Ala Trp Ser Gly Gly Pro Thr Tyr Tyr Ala Asn Trp Ala Lys Gly
    50                  55                  60

Arg Phe Thr Ile Ser Lys Ser Ser Thr Thr Val Asp Leu Lys Ile Thr
65                  70                  75                  80

Ser Pro Thr Thr Ala Asp Thr Ala Thr Tyr Phe Cys Ala Arg Gly Tyr
                85                  90                  95

Asn Gly Met Asp Pro Trp Gly Pro Gly Thr Leu Val Thr Val Ser Ser
            100                 105                 110

<210> SEQ ID NO 39
<211> LENGTH: 112
<212> TYPE: PRT
<213> ORGANISM: Oryctolagus cuniculus

<400> SEQUENCE: 39

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Asp Val
            20                  25                  30

Val Ser Trp Val Arg Gln Ala Pro Gly Lys Gly Leu Glu Trp Ile Gly
        35                  40                  45

Tyr Thr Trp Asn Gly Gly Ala Thr Phe Tyr Ala Ser Trp Ala Lys Gly
    50                  55                  60

Arg Phe Thr Phe Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Asn Gly Met Asp Pro Trp Gly Pro Gly Thr Leu Val Thr Val Ser Ser
            100                 105                 110

<210> SEQ ID NO 40
<211> LENGTH: 112
<212> TYPE: PRT
<213> ORGANISM: Oryctolagus cuniculus

<400> SEQUENCE: 40

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Gly Val
            20                  25                  30

Val Ser Trp Val Arg Gln Ala Pro Gly Lys Gly Leu Glu Trp Ile Gly
        35                  40                  45

Tyr Ala Trp Ser Gly Gly Pro Thr Tyr Tyr Ala Asn Trp Ala Lys Gly
    50                  55                  60

```
Arg Phe Thr Ile Ser Lys Ser Thr Thr Val Asp Leu Lys Ile Thr
65                  70                  75                  80

Ser Pro Thr Thr Ala Asp Thr Ala Thr Tyr Phe Cys Ala Arg Gly Tyr
                85                  90                  95

Asn Gly Met Asp Pro Trp Gly Pro Gly Thr Leu Val Thr Val Ser Ser
            100                 105                 110
```

<210> SEQ ID NO 41
<211> LENGTH: 112
<212> TYPE: PRT
<213> ORGANISM: Oryctolagus cuniculus

<400> SEQUENCE: 41

```
Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Asn Tyr Glu
                20                  25                  30

Met Asn Trp Val Arg Gln Ala Pro Gly Lys Gly Leu Glu Trp Ile Gly
            35                  40                  45

Tyr Ile Asp Val Gly Ser Gly Thr Trp Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ser Arg Gln Tyr
                85                  90                  95

Asn Pro Met Asp Leu Trp Gly Pro Gly Thr Leu Val Thr Val Ser Ser
            100                 105                 110
```

<210> SEQ ID NO 42
<211> LENGTH: 116
<212> TYPE: PRT
<213> ORGANISM: Oryctolagus cuniculus

<400> SEQUENCE: 42

```
Gln Ser Val Lys Glu Ser Gly Gly Gly Leu Val Thr Pro Gly Gly Thr
1               5                   10                  15

Leu Thr Leu Thr Cys Thr Val Ser Gly Phe Ser Leu Ser Arg Asn Ala
                20                  25                  30

Met Ser Trp Val Arg Gln Thr Pro Gly Lys Gly Leu Glu Trp Ile Gly
            35                  40                  45

Tyr Ile Tyr Ser Gly Ser Ser Pro Tyr Tyr Ala Asn Trp Ala Lys Gly
        50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg His Val
                85                  90                  95

Ser Asp Gly Gly Trp Tyr Leu Asp Ile Trp Gly Pro Gly Thr Leu Val
            100                 105                 110

Ala Val Ser Leu
        115
```

<210> SEQ ID NO 43
<211> LENGTH: 117
<212> TYPE: PRT
<213> ORGANISM: Oryctolagus cuniculus

<400> SEQUENCE: 43

-continued

Gln Glu Gln Leu Lys Glu Ser Gly Gly Gly Leu Val Thr Pro Gly Gly
1               5                   10                  15

Ile Leu Thr Leu Thr Cys Thr Ala Ser Gly Phe Ser Leu Arg Ser Asn
            20                  25                  30

Ala Met Ser Trp Val Arg Gln Ala Pro Gly Lys Gly Leu Glu Trp Ile
        35                  40                  45

Gly Tyr Ile Tyr Pro Gly Gly Ala Pro His Tyr Ala Ser Trp Ala Lys
    50                  55                  60

Gly Arg Phe Thr Ile Ser Arg Asn Ser Thr Thr Val Asp Leu Lys Met
65                  70                  75                  80

Thr Ser Leu Thr Thr Glu Asp Thr Ala Thr Tyr Phe Cys Ala Arg His
                85                  90                  95

Val Ser Gly Gly Gly Trp Tyr Leu Asp Ile Trp Gly Pro Gly Thr Leu
            100                 105                 110

Val Thr Val Ser Leu
        115

<210> SEQ ID NO 44
<211> LENGTH: 117
<212> TYPE: PRT
<213> ORGANISM: Oryctolagus cuniculus

<400> SEQUENCE: 44

Gln Glu Gln Leu Lys Glu Ser Gly Gly Gly Leu Val Thr Pro Gly Gly
1               5                   10                  15

Ile Leu Thr Leu Thr Cys Thr Ala Ser Gly Phe Ser Leu Arg Ser Asn
            20                  25                  30

Ala Met Ser Trp Val Arg Gln Ala Pro Gly Lys Gly Leu Glu Trp Ile
        35                  40                  45

Gly Tyr Ile Tyr Pro Gly Gly Ala Pro His Tyr Ala Ser Trp Ala Lys
    50                  55                  60

Gly Arg Phe Thr Ile Ser Arg Asn Ser Thr Thr Val Asp Leu Lys Met
65                  70                  75                  80

Thr Ser Leu Thr Thr Glu Asp Thr Ala Thr Tyr Phe Cys Ala Arg His
                85                  90                  95

Val Ser Gly Gly Gly Trp Tyr Leu Asp Ile Trp Gly Pro Gly Thr Leu
            100                 105                 110

Val Thr Val Ser Leu
        115

<210> SEQ ID NO 45
<211> LENGTH: 120
<212> TYPE: PRT
<213> ORGANISM: Oryctolagus cuniculus

<400> SEQUENCE: 45

Gln Ser Leu Glu Glu Ser Gly Gly Gly Leu Val Gln Pro Glu Gly Ser
1               5                   10                  15

Pro Thr Leu Thr Cys Thr Ala Tyr Leu Ile Asp Phe Ser Arg Tyr Gly
            20                  25                  30

Tyr Met Cys Trp Val Arg Gln Ala Pro Gly Lys Gly Leu Glu Trp Ile
        35                  40                  45

Gly Cys Ile His Ala Gly Arg Ser Gly Arg Thr Tyr Tyr Ala Asn Trp
    50                  55                  60

Ala Lys Gly Arg Phe Thr Ile Ser Lys Thr Ser Ser Thr Thr Val Thr
65                  70                  75                  80

```
Leu Gln Met Thr Ser Leu Thr Ala Ala Asp Thr Ala Thr Tyr Phe Cys
                85                  90                  95

Ala Lys Ser Gly Asp Ser Tyr Val Gly Tyr Phe Ala Leu Trp Gly Pro
            100                 105                 110

Gly Thr Leu Val Thr Val Ser Ser
        115                 120

<210> SEQ ID NO 46
<211> LENGTH: 112
<212> TYPE: PRT
<213> ORGANISM: Oryctolagus cuniculus

<400> SEQUENCE: 46

Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Asn Tyr Glu
            20                  25                  30

Ile Asn Trp Val Arg Gln Ala Pro Gly Lys Gly Leu Glu Trp Ile Gly
        35                  40                  45

Tyr Ile Asp Val Gly Ser Gly Thr Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Gly Asp Thr Ala Thr Tyr Phe Cys Ser Arg Ser Tyr
                85                  90                  95

Asn Pro Met Asp Leu Trp Gly Pro Gly Thr Leu Val Thr Val Ser Ser
            100                 105                 110

<210> SEQ ID NO 47
<211> LENGTH: 118
<212> TYPE: PRT
<213> ORGANISM: Oryctolagus cuniculus

<400> SEQUENCE: 47

Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Ser Leu Ser Ser Asn
            20                  25                  30

Gly Met Ser Trp Val Arg Gln Ala Pro Gly Lys Gly Leu Glu Trp Ile
        35                  40                  45

Gly Tyr Ile Tyr Ser Gly Ser Ser Pro Tyr Tyr Ala Ser Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Lys Tyr Phe Cys Ala Arg
                85                  90                  95

His Val Ser Gly Gly Gly Trp Tyr Leu Asp Ile Trp Gly Pro Gly Thr
            100                 105                 110

Leu Val Thr Val Ser Leu
        115

<210> SEQ ID NO 48
<211> LENGTH: 118
<212> TYPE: PRT
<213> ORGANISM: Oryctolagus cuniculus

<400> SEQUENCE: 48

Gln Glu Asp Leu Lys Glu Ser Gly Gly Gly Leu Ile Thr Pro Gly Gly
```

```
            1               5                   10                  15
        Thr Leu Thr Leu Thr Cys Thr Gly Ser Gly Phe Ser Leu Ser Ser Asp
                        20                  25                  30

Gly Met Ser Trp Val Arg Gln Ala Pro Gly Lys Gly Leu Glu Trp Ile
                        35                  40                  45

Gly Tyr Ile Tyr Ser Gly Ser Ser Pro Tyr Tyr Ala Asn Trp Ala Lys
                        50                  55                  60

Gly Arg Phe Thr Ile Ser Lys Thr Ser Ser Thr Val Asp Leu Lys
         65                 70                  75                  80

Met Thr Ser Leu Thr Thr Glu Asp Thr Ala Thr Tyr Phe Cys Ala Arg
                        85                  90                  95

His Leu Ser Gly Gly Gly Trp Tyr Leu Asp Ile Trp Gly Pro Gly Thr
                        100                 105                 110

Leu Val Thr Val Ser Leu
                115
```

<210> SEQ ID NO 49
<211> LENGTH: 121
<212> TYPE: PRT
<213> ORGANISM: Oryctolagus cuniculus

<400> SEQUENCE: 49

```
        Gln Glu Gln Leu Glu Glu Ser Gly Gly Gly Leu Val Lys Pro Glu Gly
         1               5                   10                  15

Ser Leu Thr Leu Thr Cys Thr Ala Ser Gly Phe Asp Leu Ser Thr Tyr
                        20                  25                  30

Tyr Tyr Met Cys Trp Val Arg Gln Ala Pro Gly Lys Gly Leu Glu Trp
                        35                  40                  45

Ile Ala Cys Ile Tyr Thr Gly Arg Ala Ser Thr Tyr Tyr Ala Thr Trp
                        50                  55                  60

Ala Lys Gly Arg Phe Thr Ile Ser Lys Thr Ser Ser Thr Thr Val Thr
         65                 70                  75                  80

Leu Gln Met Thr Ser Leu Thr Ala Ala Asp Thr Ala Thr Phe Phe Cys
                        85                  90                  95

Ala Ser Lys Ala Gly Asp Ile Trp Tyr Tyr Gly Met Asp Leu Trp Gly
                        100                 105                 110

Pro Gly Thr Leu Val Thr Val Ser Ser
                115                 120
```

<210> SEQ ID NO 50
<211> LENGTH: 113
<212> TYPE: PRT
<213> ORGANISM: Oryctolagus cuniculus

<400> SEQUENCE: 50

```
        Gln Ser Leu Glu Glu Ser Gly Gly Arg Leu Val Thr Pro Gly Thr Pro
         1               5                   10                  15

Leu Thr Leu Thr Cys Thr Ala Ser Gly Phe Thr Ile Ser Thr Asp Val
                        20                  25                  30

Ile Ser Trp Val Arg Gln Ala Pro Gly Lys Gly Leu Glu Trp Ile Gly
                        35                  40                  45

Tyr Thr Trp Ser Gly Gly Ser Thr Tyr Tyr Ala Asn Trp Ala Lys Gly
                        50                  55                  60

Arg Phe Thr Leu Ser Lys Thr Ser Ser Thr Val Asp Leu Lys Ile
         65                 70                  75                  80

Thr Ser Pro Thr Ile Glu Asp Thr Ala Thr Tyr Phe Cys Ala Arg Gly
```

-continued

```
                    85                  90                  95

Phe Asn Pro Phe Asp Pro Trp Gly Pro Gly Thr Leu Val Thr Val Ser
                100                 105                 110

Ser

<210> SEQ ID NO 51
<211> LENGTH: 113
<212> TYPE: PRT
<213> ORGANISM: Oryctolagus cuniculus

<400> SEQUENCE: 51

Gln Ser Val Glu Glu Ser Gly Gly Arg Leu Val Lys Pro Gly Glu Ser
1               5                   10                  15

Leu Thr Leu Thr Cys Thr Ala Ser Gly Phe Ser Leu Ser Ser Asp Val
                20                  25                  30

Ile Ser Trp Val Arg Gln Ala Pro Gly Lys Gly Leu Glu Trp Ile Gly
            35                  40                  45

Tyr Gly Trp Ser Gly Gly Pro Thr Tyr Tyr Ala Asn Trp Ala Lys Gly
        50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Phe Asn Pro Phe Asp Pro Trp Gly Pro Gly Thr Leu Val Thr Val Ser
                100                 105                 110

Ser

<210> SEQ ID NO 52
<211> LENGTH: 113
<212> TYPE: PRT
<213> ORGANISM: Oryctolagus cuniculus

<400> SEQUENCE: 52

Gln Ser Val Glu Glu Ser Gly Gly Arg Leu Ile Thr Pro Gly Thr Pro
1               5                   10                  15

Leu Thr Leu Thr Cys Thr Val Ser Gly Phe Ser Leu Ser Thr Asp Val
                20                  25                  30

Val Ser Trp Val Arg Gln Ala Pro Gly Thr Gly Leu Glu Trp Ile Gly
            35                  40                  45

Tyr Thr Trp Ser Gly Gly Ser Thr Tyr Tyr Ala Ile Trp Ala Lys Gly
        50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Phe Asn Pro Phe Asp Pro Trp Gly Pro Gly Thr Leu Val Thr Val Ser
                100                 105                 110

Ser

<210> SEQ ID NO 53
<211> LENGTH: 113
<212> TYPE: PRT
<213> ORGANISM: Oryctolagus cuniculus

<400> SEQUENCE: 53

Gln Ser Val Glu Glu Ser Gly Gly Arg Leu Val Thr Pro Gly Thr Leu
1               5                   10                  15
```

```
Leu Thr Leu Thr Cys Thr Val Ser Gly Phe Ser Leu Ser Thr Asp Val
            20                  25                  30

Leu Ser Trp Val Arg Gln Ala Pro Gly Lys Gly Leu Glu Trp Ile Gly
        35                  40                  45

Tyr Thr Trp Ser Gly Gly Ser Thr Tyr Tyr Ala Ser Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Phe Asn Pro Phe Asp Pro Trp Gly Pro Gly Thr Leu Val Thr Val Ser
            100                 105                 110

Ser

<210> SEQ ID NO 54
<211> LENGTH: 114
<212> TYPE: PRT
<213> ORGANISM: Oryctolagus cuniculus

<400> SEQUENCE: 54

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ile Tyr Glu
            20                  25                  30

Ile Ser Trp Val Arg Gln Ala Pro Gly Lys Glu Leu Glu Trp Ile Gly
        35                  40                  45

Tyr Ile Gly Val Gly Gly Val Thr Tyr Tyr Ala Asn Trp Ala Lys Ser
    50                  55                  60

Arg Ser Thr Ile Thr Arg Asn Thr Asn Gln Lys Met Val Ala Leu Lys
65                  70                  75                  80

Met Thr Ser Leu Thr Ala Ala Asp Thr Ala Thr Tyr Phe Cys Ala Arg
                85                  90                  95

Gly Tyr Asn Pro Phe Asp Leu Trp Gly Pro Gly Thr Leu Val Thr Val
            100                 105                 110

Ser Ser

<210> SEQ ID NO 55
<211> LENGTH: 108
<212> TYPE: PRT
<213> ORGANISM: Oryctolagus cuniculus

<400> SEQUENCE: 55

Asp Met Thr Gln Thr Pro Ala Ser Val Glu Val Ala Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Gly
        35                  40                  45

Ala Ser Thr Leu Ala Ser Gly Val Ser Ser Arg Phe Lys Gly Ser Gly
    50                  55                  60

Ser Gly Thr Gln Phe Thr Phe Thr Ile Ser Asp Val Glu Cys Thr Asp
65                  70                  75                  80

Pro Ala Thr Tyr Tyr Cys Gln Gln Ala Tyr Ser Ile Ser Asn Val Asp
                85                  90                  95

Asn Pro Phe Gly Gly Gly Thr Glu Val Val Val Lys
```

```
                    100                 105

<210> SEQ ID NO 56
<211> LENGTH: 107
<212> TYPE: PRT
<213> ORGANISM: Oryctolagus cuniculus

<400> SEQUENCE: 56

Gln Met Cys Leu Arg His Asp Pro Asp Ser Ser Leu Cys Gly Gly Ser
1               5                   10                  15

Cys Gly Arg His Ser His His Gln Leu Pro Gly Gln Ser Glu His Trp
            20                  25                  30

Phe Ser Leu Val Ser Ala Glu Thr Arg Ala Ala Ser Gln Ala Pro Asp
        35                  40                  45

Leu Trp Cys Ile His Ser Gly Ile Trp Gly Leu Ile Ala Val Gln Arg
    50                  55                  60

Gln Trp Ile Trp Asp Thr Val His Phe His Gln Arg Arg Gly Val
65                  70                  75                  80

Tyr Arg Cys Cys His Leu Leu Leu Ser Thr Gly Ile Cys Ala Cys Arg
                85                  90                  95

Cys Phe Arg Arg Arg Asp Arg Asp Gly Gly Gln
            100                 105

<210> SEQ ID NO 57
<211> LENGTH: 108
<212> TYPE: PRT
<213> ORGANISM: Oryctolagus cuniculus

<400> SEQUENCE: 57

Asp Met Thr Gln Thr Pro Ala Ser Val Glu Val Ala Val Gly Gly Thr
1               5                   10                  15

Val Thr Ile Lys Cys Gln Ala Ser Gln Ser Ile Gly Ser Asn Leu Ala
            20                  25                  30

Trp Tyr Gln Gln Lys Pro Gly Gln Ser Pro Lys Leu Leu Ile Tyr Ser
        35                  40                  45

Ala Ser Ile Leu Ala Ser Gly Val Pro Ser Arg Phe Lys Gly Ser Gly
    50                  55                  60

Ser Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Val Gly Asn Ile Asp
                85                  90                  95

Asn Ala Phe Gly Gly Gly Thr Glu Val Val Val Lys
            100                 105

<210> SEQ ID NO 58
<211> LENGTH: 108
<212> TYPE: PRT
<213> ORGANISM: Oryctolagus cuniculus

<400> SEQUENCE: 58

Asp Met Ile Gln Thr Pro Ala Ser Val Glu Val Ala Val Gly Gly Thr
1               5                   10                  15

Val Thr Ile Gly Cys Gln Ala Ser Gln Ser Ile Gly Ser Asn Leu Gly
            20                  25                  30

Trp Tyr Gln Gln Lys Pro Gly Gln Pro Pro Lys Leu Leu Ile Tyr Ser
        35                  40                  45

Ala Ser Thr Leu Ala Ser Gly Val Ser Ser Arg Phe Lys Gly Ser Gly
    50                  55                  60
```

Ser Gly Thr Glu Phe Thr Leu Thr Ile Ser Asp Val Glu Cys Asp Asp
65                  70                  75                  80

Ala Ala Thr Tyr Tyr Cys Gln Gln Ala Tyr Ser Val Ser Asn Val Asp
                85                  90                  95

Asn Ala Phe Gly Gly Gly Thr Glu Val Val Val Lys
            100                 105

<210> SEQ ID NO 59
<211> LENGTH: 108
<212> TYPE: PRT
<213> ORGANISM: Oryctolagus cuniculus

<400> SEQUENCE: 59

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Ser
        35                  40                  45

Thr Ser Thr Val Ala Ser Gly Val Pro Ser Arg Phe Lys Gly Ser Gly
    50                  55                  60

Phe Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Ala Gly Asn Val Asn
                85                  90                  95

Asn Pro Phe Gly Gly Gly Thr Glu Val Val Val Lys
            100                 105

<210> SEQ ID NO 60
<211> LENGTH: 108
<212> TYPE: PRT
<213> ORGANISM: Oryctolagus cuniculus

<400> SEQUENCE: 60

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Lys
        35                  40                  45

Ala Ser Thr Leu Ala Ser Gly Val Pro Ser Arg Phe Arg Gly Ser Gly
    50                  55                  60

Ser Gly Thr Glu Phe Thr Leu Ala Ile Ser Asp Leu Glu Cys Ala Asp
65                  70                  75                  80

Ala Ala Thr Tyr Tyr Cys Gln Gln Gly Tyr Thr Thr Lys Asp Leu Val
                85                  90                  95

Asn Pro Phe Gly Gly Gly Thr Glu Val Val Val Lys
            100                 105

<210> SEQ ID NO 61
<211> LENGTH: 108
<212> TYPE: PRT
<213> ORGANISM: Oryctolagus cuniculus

<400> SEQUENCE: 61

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Ser Lys
            35                  40                  45

Ala Ser Thr Leu Ala Ser Gly Val Pro Ser Arg Phe Lys Gly Ser Gly
 50                      55                  60

Ser Gly Thr Glu Phe Thr Leu Ala Ile Ser Asp Leu Glu Cys Ala Asp
65                  70                  75                  80

Ala Ala Thr Tyr Tyr Cys Gln Gln Gly Tyr Thr Thr Lys Asn Val Val
                85                  90                  95

Asn Pro Phe Gly Gly Gly Thr Glu Val Val Val Lys
            100                 105

<210> SEQ ID NO 62
<211> LENGTH: 108
<212> TYPE: PRT
<213> ORGANISM: Oryctolagus cuniculus

<400> SEQUENCE: 62

Asp Met Ile Gln Thr Pro Ala Ser Val Glu Val Ala Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Gly
            35                  40                  45

Thr Ser Thr Leu Ala Ser Gly Val Ser Ser Arg Phe Lys Gly Ser Gly
 50                      55                  60

Phe Gly Thr Gln Phe Thr Phe Thr Ile Ser Asp Val Glu Cys Thr Asp
65                  70                  75                  80

Ala Ala Thr Tyr Tyr Cys Gln Gln Ala Tyr Ser Ile Ser Asn Val Asp
                85                  90                  95

Asn Ala Phe Gly Gly Gly Thr Glu Val Val Val Lys
            100                 105

<210> SEQ ID NO 63
<211> LENGTH: 108
<212> TYPE: PRT
<213> ORGANISM: Oryctolagus cuniculus

<400> SEQUENCE: 63

Ile Val Met Thr Gln Thr Pro Ser Pro Val Ser Gly Ala Val Gly Gly
1               5                   10                  15

Thr Val Thr Ile Asn Cys Gln Ala Ser Gln Ser Ile Gly Ser Asn Leu
            20                  25                  30

Ala Trp Tyr Gln Gln Lys Pro Gly Gln Pro Pro Lys Leu Leu Ile Tyr
            35                  40                  45

Ser Ala Ser Ile Leu Ala Ser Gly Ala Pro Ser Arg Val Ser Gly Ser
 50                      55                  60

Gly Tyr Gly Thr Glu Phe Thr Leu Thr Ile Ser Gly Val Gln Cys Ala
65                  70                  75                  80

Asp Ala Ala Thr Tyr Tyr Cys Gln Gln Gly Tyr Thr Thr Asn Ala Asp
                85                  90                  95

Asn Ile Phe Gly Gly Gly Thr Glu Val Val Val Glu
            100                 105

<210> SEQ ID NO 64
<211> LENGTH: 108

<212> TYPE: PRT
<213> ORGANISM: Oryctolagus cuniculus

<400> SEQUENCE: 64

Val Met Thr Gln Thr Pro Ala Ser Val Ser Gly Pro Val Gly Gly Thr
1               5                   10                  15

Val Thr Ile Lys Cys Gln Ala Ser Gln Ser Ile Gly Ser Asn Leu Gly
            20                  25                  30

Trp Tyr Gln Gln Lys Pro Gly Gln Pro Pro Lys Leu Leu Ile Phe Ser
        35                  40                  45

Ala Ser Asn Leu Glu Ser Gly Val Pro Ser Arg Phe Lys Gly Ser Gly
    50                  55                  60

Ser Gly Thr Gln Phe Thr Leu Thr Ile Ser Asp Leu Glu Cys Asp Asp
65                  70                  75                  80

Ala Ala Thr Tyr Tyr Cys Gln Gln Gly Tyr Thr Thr Asn Asn Val Leu
                85                  90                  95

Asn Ala Phe Ala Gly Gly Thr Glu Val Val Val Lys
            100                 105

<210> SEQ ID NO 65
<211> LENGTH: 108
<212> TYPE: PRT
<213> ORGANISM: Oryctolagus cuniculus

<400> SEQUENCE: 65

Asp Met Ile Gln Thr Pro Ala Ser Val Glu Val Ala Val Gly Gly Thr
1               5                   10                  15

Val Thr Ile Asn Cys Gln Ala Ser Gln Ser Ile Gly Ser Asn Leu Ala
            20                  25                  30

Trp Tyr Gln Gln Lys Pro Gly Gln Pro Pro Lys Leu Leu Ile Tyr Gly
        35                  40                  45

Ala Ser Thr Leu Ala Ser Gly Val Pro Ser Arg Phe Lys Gly Ser Gly
    50                  55                  60

Ser Gly Thr Gln Phe Thr Phe Thr Ile Ser Asp Val Glu Cys Thr Ala
65                  70                  75                  80

Ala Ala Thr Tyr Tyr Cys Gln Gln Ala Tyr Ser Ile Ser Asn Val Asp
                85                  90                  95

Asn Ala Phe Gly Gly Gly Thr Glu Val Val Val Lys
            100                 105

<210> SEQ ID NO 66
<211> LENGTH: 108
<212> TYPE: PRT
<213> ORGANISM: Oryctolagus cuniculus

<400> SEQUENCE: 66

Asp Met Thr Gln Thr Pro Ala Ser Val Glu Ala Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Ser
        35                  40                  45

Ala Ser Thr Leu Ala Ser Gly Val Pro Ser Arg Phe Lys Gly Ser Gly
    50                  55                  60

Ser Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Val Gly Asn Val Asn

-continued

```
                    85                  90                  95

Asn Ala Phe Gly Gly Gly Thr Glu Val Val Val Lys
            100                 105

<210> SEQ ID NO 67
<211> LENGTH: 108
<212> TYPE: PRT
<213> ORGANISM: Oryctolagus cuniculus

<400> SEQUENCE: 67

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Ser
        35                  40                  45

Thr Ser Thr Val Ala Ser Gly Val Pro Ser Arg Phe Lys Gly Ser Gly
    50                  55                  60

Phe Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Ala Gly Asn Val Asn
                85                  90                  95

Asn Pro Phe Gly Gly Gly Thr Glu Val Val Val Lys
            100                 105

<210> SEQ ID NO 68
<211> LENGTH: 108
<212> TYPE: PRT
<213> ORGANISM: Oryctolagus cuniculus

<400> SEQUENCE: 68

Asp Met Ile Gln Thr Pro Ala Ser Val Glu Val Ala Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Gly
        35                  40                  45

Thr Ser Thr Leu Ala Ser Gly Val Ser Ser Arg Phe Lys Gly Ser Gly
    50                  55                  60

Phe Gly Thr Gln Phe Thr Phe Thr Ile Ser Asp Val Glu Cys Thr Asp
65                  70                  75                  80

Ala Ala Thr Tyr Tyr Cys Gln Gln Ala Tyr Ser Thr Ser Lys Ile Asp
                85                  90                  95

Asn Ala Phe Gly Gly Gly Thr Glu Val Val Val Lys
            100                 105

<210> SEQ ID NO 69
<211> LENGTH: 108
<212> TYPE: PRT
<213> ORGANISM: Oryctolagus cuniculus

<400> SEQUENCE: 69

Asp Met Ile Gln Thr Pro Ala Ser Val Glu Val Ala Val Gly Gly Thr
1               5                   10                  15

Val Thr Ile Asn Cys Gln Ala Ser Gln Ser Ile Gly Ser Asn Leu Ala
            20                  25                  30

Trp Tyr Gln Gln Lys Pro Gly Gln Pro Pro Lys Leu Leu Ile Tyr Ser
        35                  40                  45
```

Ala Ser Thr Leu Ala Ser Gly Val Ser Ser Arg Phe Lys Gly Ser Gly
        50                  55                  60

Ser Gly Thr Asp Tyr Thr Leu Thr Ile Ser Asp Val Glu Cys Thr Asp
 65                  70                  75                  80

Ala Ala Thr Tyr Tyr Cys Gln Gln Ala Tyr Ser Ile Ser Asn Val Glu
                85                  90                  95

Asn Pro Phe Gly Gly Gly Thr Glu Val Val Val Lys
            100                 105

<210> SEQ ID NO 70
<211> LENGTH: 108
<212> TYPE: PRT
<213> ORGANISM: Oryctolagus cuniculus

<400> SEQUENCE: 70

Asp Met Thr Gln Thr Pro Ala Ser Val Glu Ala Ala Val Gly Gly Thr
 1               5                  10                  15

Val Thr Ile Lys Cys Gln Ala Ser Gln Asn Ile Gly Ser Asn Leu Ala
                20                  25                  30

Trp Tyr Gln Gln Lys Pro Gly Gln Arg Pro Lys Leu Leu Ile Tyr Ser
            35                  40                  45

Ala Ser Thr Leu Ala Ser Gly Val Pro Ser Arg Phe Lys Gly Ser Gly
        50                  55                  60

Ser Gly Thr Gln Phe Thr Leu Thr Ile Ser Gly Val Gln Cys Asp Asp
 65                  70                  75                  80

Ala Ala Thr Tyr Tyr Cys Gln Gln Gly Tyr Ser Val Gly Asn Val Asn
                85                  90                  95

Asn Ala Phe Gly Gly Gly Thr Glu Val Val Val Lys
            100                 105

<210> SEQ ID NO 71
<211> LENGTH: 108
<212> TYPE: PRT
<213> ORGANISM: Oryctolagus cuniculus

<400> SEQUENCE: 71

Asp Met Thr Gln Thr Pro Ala Ser Val Glu Val Ala Val Gly Gly Thr
 1               5                  10                  15

Val Thr Ile Lys Cys Gln Ala Ser Gln Asn Ile Gly Tyr Asn Leu Ala
                20                  25                  30

Trp Tyr Gln Gln Lys Pro Gly Gln Pro Pro Lys Leu Leu Ile Tyr Gly
            35                  40                  45

Ala Ser Thr Leu Ala Ser Gly Val Pro Ser Arg Phe Lys Gly Ser Gly
        50                  55                  60

Ser Gly Thr Gln Phe Thr Leu Thr Ile Ser Gly Val Gln Cys Asp Asp
 65                  70                  75                  80

Ala Ala Thr Tyr Tyr Cys Gln Gln Gly Tyr Ser Val Ser Asn Ile Asp
                85                  90                  95

Asn Ala Phe Gly Gly Gly Thr Glu Val Val Val Lys
            100                 105

<210> SEQ ID NO 72
<211> LENGTH: 107
<212> TYPE: PRT
<213> ORGANISM: Oryctolagus cuniculus

<400> SEQUENCE: 72

Asp Met Thr Gln Thr Pro Ala Ser Val Glu Ala Ala Val Gly Gly Thr
1               5                   10                  15

Val Thr Ile Lys Cys Gln Ala Ser Gln Ser Ile Gly Ser Tyr Leu Ser
            20                  25                  30

Trp Tyr His Gln Lys Pro Gly Gln Pro Pro Lys Leu Leu Ile Tyr Arg
                35                  40                  45

Ala Ser Thr Leu Ala Ser Gly Val Pro Ser Arg Phe Lys Gly Ser Gly
        50                  55                  60

Ser Gly Thr Gln Phe Thr Leu Thr Ile Ser Asp Leu Glu Cys Ala Asp
65                  70                  75                  80

Ala Ala Thr Tyr Tyr Cys Gln Gln Gly Tyr Ser Ala Asn Val Asp Asn
                85                  90                  95

Ala Phe Gly Gly Gly Thr Glu Val Val Val Lys
            100                 105

<210> SEQ ID NO 73
<211> LENGTH: 108
<212> TYPE: PRT
<213> ORGANISM: Oryctolagus cuniculus

<400> SEQUENCE: 73

Asp Met Thr Gln Thr Pro Ala Ser Val Ser Ala Ala Val Gly Gly Thr
1               5                   10                  15

Val Thr Ile Asn Cys Gln Ala Ser Gln Ser Ile Gly Ser Asn Leu Gly
            20                  25                  30

Trp Tyr Gln Gln Lys Pro Gly Gln Pro Pro Lys Leu Leu Ile Tyr Gly
                35                  40                  45

Ala Ser Thr Leu Ala Ser Gly Val Ser Ser Arg Phe Lys Gly Ser Gly
        50                  55                  60

Ser Gly Thr His Phe Ala Phe Thr Ile Ser Asp Val Glu Cys Thr Asp
65                  70                  75                  80

Ala Ala Thr Tyr Tyr Cys Gln Gln Ala Tyr Ser Val Gly Asn Val Asp
                85                  90                  95

Asn Ala Phe Gly Gly Gly Thr Glu Val Val Val Lys
            100                 105

<210> SEQ ID NO 74
<211> LENGTH: 108
<212> TYPE: PRT
<213> ORGANISM: Oryctolagus cuniculus

<400> SEQUENCE: 74

Asp Met Thr Gln Thr Pro Ala Ser Val Glu Ala Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Ser
                35                  40                  45

Ala Ser Thr Leu Ala Ser Gly Val Pro Ser Arg Phe Lys Gly Ser Gly
        50                  55                  60

Ser Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Val Gly Asn Val Asn
                85                  90                  95

Asn Ala Phe Gly Gly Gly Thr Glu Val Val Val Lys
            100                 105

<210> SEQ ID NO 75
<211> LENGTH: 108
<212> TYPE: PRT
<213> ORGANISM: Oryctolagus cuniculus

<400> SEQUENCE: 75

Asp Met Ile Gln Thr Pro Ala Ser Val Glu Val Ala Val Gly Gly Thr
1               5                   10                  15

Val Thr Ile Asn Cys Gln Ala Ser Gln Ser Ile Gly Ser Asn Leu Ala
            20                  25                  30

Trp Tyr Gln Gln Lys Pro Gly Gln Pro Pro Lys Leu Leu Ile Tyr Leu
        35                  40                  45

Ala Ser Thr Leu Pro Ser Gly Val Pro Ser Arg Phe Lys Gly Ser Gly
    50                  55                  60

Ser Gly Thr Gln Phe Thr Phe Thr Ile Ser Asp Val Glu Cys Thr Asp
65                  70                  75                  80

Ala Ala Thr Tyr Tyr Cys Gln Gln Ala Tyr Thr Ala Ser Asn Val Asp
                85                  90                  95

Asn Ala Phe Gly Gly Gly Thr Glu Val Val Val Lys
            100                 105

<210> SEQ ID NO 76
<211> LENGTH: 111
<212> TYPE: PRT
<213> ORGANISM: Oryctolagus cuniculus

<400> SEQUENCE: 76

Ile Val Met Thr Gln Thr Pro Ala Ser Val Glu Ala Ala Val Gly Gly
1               5                   10                  15

Thr Val Thr Ile Lys Cys Gln Ala Ser Gln Asn Ile Tyr Asn Tyr Leu
            20                  25                  30

Ala Trp Tyr Gln Gln Gln Pro Gly Gln Pro Pro Lys Leu Leu Ile Tyr
        35                  40                  45

Ser Ala Ser Asn Leu Ala Ser Gly Val Ser Ser Arg Phe Lys Gly Ser
    50                  55                  60

Gly Ser Gly Thr Glu Phe Thr Leu Thr Ile Ser Asp Leu Glu Cys Gly
65                  70                  75                  80

Asp Ala Ala Thr Tyr Tyr Cys Gln Ser Tyr Tyr Asp Ser Ser Arg Ile
                85                  90                  95

Ser Tyr Gly Ser Ala Phe Gly Gly Gly Thr Glu Val Val Val Lys
            100                 105                 110

<210> SEQ ID NO 77
<211> LENGTH: 108
<212> TYPE: PRT
<213> ORGANISM: Oryctolagus cuniculus

<400> SEQUENCE: 77

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Lys
        35                  40                  45

Ala Ser Thr Leu Ala Ser Gly Val Pro Ser Arg Phe Arg Gly Ser Gly
    50                  55                  60

Ser Gly Thr Glu Phe Thr Leu Ala Ile Ser Asp Leu Glu Cys Ala Asp

```
                65                  70                  75                  80
Ala Ala Thr Tyr Tyr Cys Gln Gln Gly Tyr Thr Thr Lys Asp Val Val
                85                  90                  95

Asn Pro Phe Gly Gly Gly Thr Glu Val Val Val Lys
            100                 105

<210> SEQ ID NO 78
<211> LENGTH: 108
<212> TYPE: PRT
<213> ORGANISM: Oryctolagus cuniculus

<400> SEQUENCE: 78

Asp Met Thr Gln Thr Pro Ala Ser Val Glu Ala Val Gly Gly Ala
1               5                   10                  15

Val Thr Ile Lys Cys Gln Ala Ser Gln Asn Ile Gly Ser Asn Leu Ala
                20                  25                  30

Trp Tyr His Gln Lys Pro Gly Gln Pro Pro Lys Leu Leu Ile Ser Lys
            35                  40                  45

Ala Ser Thr Leu Ala Ser Gly Val Pro Ser Arg Phe Lys Gly Ser Gly
        50                  55                  60

Ser Gly Thr Glu Phe Thr Leu Ala Ile Ser Asp Leu Glu Cys Ala Asp
65                  70                  75                  80

Ala Ala Thr Tyr Tyr Cys Gln Gln Gly Tyr Thr Thr Lys Asn Val Val
                85                  90                  95

Asn Pro Phe Gly Gly Gly Thr Glu Val Val Val Lys
            100                 105

<210> SEQ ID NO 79
<211> LENGTH: 108
<212> TYPE: PRT
<213> ORGANISM: Oryctolagus cuniculus

<400> SEQUENCE: 79

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
                20                  25                  30

Trp Tyr Gln Gln Lys Pro Gly Gln Pro Pro Lys Leu Leu Ile Tyr Lys
            35                  40                  45

Ala Ser Thr Leu Ala Ser Gly Val Pro Ser Arg Phe Arg Gly Ser Gly
        50                  55                  60

Ser Gly Thr Glu Phe Thr Leu Ala Ile Ser Asp Leu Glu Cys Ala Asp
65                  70                  75                  80

Ala Ala Thr Tyr Tyr Cys Gln Gln Gly Tyr Thr Thr Lys Asp Val Val
                85                  90                  95

Asn Pro Phe Gly Gly Gly Thr Glu Val Val Val Lys
            100                 105

<210> SEQ ID NO 80
<211> LENGTH: 108
<212> TYPE: PRT
<213> ORGANISM: Oryctolagus cuniculus

<400> SEQUENCE: 80

Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
                20                  25                  30
```

Trp Tyr Gln Gln Lys Pro Gly Gln Arg Pro Lys Leu Leu Ile Tyr Ser
            35                  40                  45

Ala Ser Thr Leu Ala Ser Gly Val Pro Ser Arg Phe Lys Gly Ser Gly
    50                  55                  60

Ser Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Val Gly Asn Val Asn
                85                  90                  95

Asn Ala Phe Gly Gly Gly Thr Glu Val Val Val Lys
            100                 105

<210> SEQ ID NO 81
<211> LENGTH: 108
<212> TYPE: PRT
<213> ORGANISM: Oryctolagus cuniculus

<400> SEQUENCE: 81

Asp Met Ile Gln Thr Pro Ala Ser Val Glu Val Val Gly Gly Thr
1               5                   10                  15

Val Thr Phe Asn Cys Gln Ala Ser Gln Asn Ile Gly Ser Asn Leu Ala
            20                  25                  30

Trp Tyr Gln Gln Lys Pro Gly Gln Pro Pro Lys Leu Leu Ile Tyr Ser
            35                  40                  45

Ala Ser Thr Leu Ala Ser Gly Val Pro Ser Arg Phe Lys Gly Ser Gly
    50                  55                  60

Ser Gly Thr Gln Phe Thr Phe Thr Ile Ser Asp Val Glu Cys Thr Asp
65                  70                  75                  80

Ala Ala Thr Tyr Tyr Cys Gln Gln Ala Tyr Ser Ile Ser Asn Val Asp
                85                  90                  95

Asn Ala Phe Gly Gly Gly Thr Glu Val Val Val Lys
            100                 105

<210> SEQ ID NO 82
<211> LENGTH: 108
<212> TYPE: PRT
<213> ORGANISM: Oryctolagus cuniculus

<400> SEQUENCE: 82

Asp Met Ile Gln Thr Pro Ala Ser Val Glu Val Gly Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Pro Lys Phe Leu Ile Tyr Gly
            35                  40                  45

Ala Ser Thr Leu Ala Ser Gly Val Ser Ser Arg Phe Lys Gly Ser Gly
    50                  55                  60

Ser Gly Thr Arg Phe Thr Phe Thr Ile Ser Asp Val Glu Cys Thr Asp
65                  70                  75                  80

Ala Ala Thr Tyr Tyr Cys Gln Gln Ala Tyr Ser Val Gly Asn Val Asp
                85                  90                  95

Asn Ala Phe Gly Gly Gly Thr Glu Val Val Val Lys
            100                 105

<210> SEQ ID NO 83
<211> LENGTH: 108
<212> TYPE: PRT
<213> ORGANISM: Oryctolagus cuniculus

<400> SEQUENCE: 83

```
Asp Met Ile Gln Thr Pro Ala Ser Val Glu Val Gly Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Pro Lys Phe Leu Ile Tyr Gly
        35                  40                  45

Ala Ser Thr Leu Ala Ser Gly Val Ser Ser Arg Phe Lys Gly Ser Gly
    50                  55                  60

Ser Gly Thr Arg Phe Thr Phe Thr Ile Ser Asp Val Glu Cys Thr Asp
65                  70                  75                  80

Ala Ala Thr Tyr Tyr Cys Gln Gln Ala Tyr Ser Val Gly Asn Val Asp
                85                  90                  95

Asn Ala Phe Gly Gly Gly Thr Glu Val Val Val Lys
            100                 105
```

<210> SEQ ID NO 84
<211> LENGTH: 112
<212> TYPE: PRT
<213> ORGANISM: Oryctolagus cuniculus

<400> SEQUENCE: 84

```
Asp Ile Val Met Thr Gln Thr Pro Ala Ser Val Glu Ala Ala Val Gly
1               5                   10                  15

Gly Thr Val Thr Ile Lys Cys Gln Ala Ser Glu Asn Ile Tyr Asn Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Asp Val Thr Ser
                85                  90                  95

His Ser Tyr Asp Asn Pro Phe Gly Gly Gly Thr Glu Val Val Val Ser
            100                 105                 110
```

<210> SEQ ID NO 85
<211> LENGTH: 108
<212> TYPE: PRT
<213> ORGANISM: Oryctolagus cuniculus

<400> SEQUENCE: 85

```
Asp Met Thr Gln Thr Pro Ala Ser Val Glu Val Ala Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Ser
        35                  40                  45

Ala Ser Thr Leu Ala Ser Gly Val Pro Ser Arg Phe Lys Gly Ser Gly
    50                  55                  60

Ser Gly Thr Gln Phe Thr Leu Thr Ile Ser Gly Val Gln Cys Asp Asp
65                  70                  75                  80

Ala Ala Thr Tyr Tyr Cys Gln Gln Gly Tyr Ser Val Gly Asn Val Asn
                85                  90                  95
```

-continued

Asn Ala Phe Gly Gly Gly Thr Glu Val Val Val Lys
            100                 105

<210> SEQ ID NO 86
<211> LENGTH: 108
<212> TYPE: PRT
<213> ORGANISM: Oryctolagus cuniculus

<400> SEQUENCE: 86

Asp Met Ile Gln Thr Pro Ala Ser Val Glu Val Ala Val Gly Gly Thr
1               5                   10                  15

Val Thr Ile Asn Cys Gln Ala Ser Gln Ser Ile Gly Ser Asn Leu Ala
            20                  25                  30

Trp Tyr Gln Gln Lys Pro Gly Gln Arg Pro Lys Leu Leu Ile Tyr Gly
        35                  40                  45

Ala Ser Thr Leu Ala Ser Gly Val Ser Ser Arg Val Lys Gly Ser Gly
    50                  55                  60

Ser Gly Thr Gln Phe Thr Phe Thr Ile Ser Asp Val Glu Cys Thr Asp
65                  70                  75                  80

Ala Ala Thr Tyr Tyr Cys Gln Gln Ala Tyr Ser Ile Ser Asn Val Asp
                85                  90                  95

Asn Ala Phe Gly Gly Gly Thr Glu Val Val Val Lys
            100                 105

<210> SEQ ID NO 87
<211> LENGTH: 108
<212> TYPE: PRT
<213> ORGANISM: Oryctolagus cuniculus

<400> SEQUENCE: 87

Asp Met Ile Gln Thr Pro Ala Ser Val Ser Glu Pro Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Gln Pro Ser Lys Leu Leu Ile Tyr Lys
        35                  40                  45

Ala Ser Thr Leu Ala Ser Gly Val Pro Ser Arg Phe Lys Gly Ser Gly
    50                  55                  60

Ser Gly Thr Asp Phe Thr Leu Thr Ile Ser Asp Leu Glu Cys Ala Asp
65                  70                  75                  80

Ala Ala Thr Tyr Tyr Cys Gln Gln Ala Tyr Thr Ile Ser Asn Val Asp
                85                  90                  95

Asn Ala Phe Gly Gly Gly Thr Glu Val Val Val Lys
            100                 105

<210> SEQ ID NO 88
<211> LENGTH: 109
<212> TYPE: PRT
<213> ORGANISM: Oryctolagus cuniculus

<400> SEQUENCE: 88

Asp Met Thr Gln Thr Pro Ala Ser Val Ser Glu Pro Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Arg
        35                  40                  45

Ala Ser Thr Leu Ala Ser Gly Val Ser Ser Arg Phe Lys Gly Ser Gly

```
                    50                  55                  60
Ser Gly Thr Gln Phe Thr Leu Thr Ile Ser Asp Leu Glu Cys Ala Asp
 65                  70                  75                  80

Ala Ala Thr Tyr Tyr Cys Gln Gln Gly Tyr Ser Ala Gly Asn Val Asp
                 85                  90                  95

Asn Asn Thr Phe Gly Gly Gly Thr Glu Val Val Val Lys
            100                 105
```

<210> SEQ ID NO 89
<211> LENGTH: 108
<212> TYPE: PRT
<213> ORGANISM: Oryctolagus cuniculus

<400> SEQUENCE: 89

```
Asp Met Ile Gln Thr Pro Ala Ser Val Ser Glu Pro Val Gly Gly Thr
  1               5                  10                  15

Val Thr Ile Val Cys Gln Ala Ser Gln Asn Ile Gly Ser Asn Phe Ala
                 20                  25                  30

Trp Tyr Gln Gln Lys Pro Gly Gln Pro Pro Lys Leu Leu Ile Tyr Arg
             35                  40                  45

Ala Ser Thr Leu Ala Ser Gly Val Ser Ser Arg Phe Lys Gly Ser Gly
         50                  55                  60

Phe Gly Thr Gln Phe Thr Leu Thr Ile Ser Asp Leu Glu Cys Ala Asp
 65                  70                  75                  80

Ala Ala Thr Tyr Tyr Cys Gln Gln Gly Tyr Ser Ala Gly Asn Val Asp
                 85                  90                  95

Asn Asn Phe Gly Gly Gly Thr Glu Val Val Val Lys
            100                 105
```

<210> SEQ ID NO 90
<211> LENGTH: 108
<212> TYPE: PRT
<213> ORGANISM: Oryctolagus cuniculus

<400> SEQUENCE: 90

```
Asp Met Thr Gln Thr Pro Ala Ser Val Ser Glu Pro Val Gly Gly Thr
  1               5                  10                  15

Val Thr Ile Lys Cys Gln Ala Ser Gln Asn Ile Gly Ser Asn Leu Ala
                 20                  25                  30

Trp Tyr Gln Gln Lys Pro Gly Gln Arg Pro Lys Leu Leu Ile Tyr Arg
             35                  40                  45

Ala Ser Thr Leu Ala Ser Gly Val Ser Ser Arg Phe Lys Gly Ser Gly
         50                  55                  60

Ser Gly Thr Gln Phe Thr Leu Thr Ile Ser Asp Leu Glu Cys Ala Asp
 65                  70                  75                  80

Ala Ala Thr Tyr Tyr Cys Gln Gln Gly Tyr Ser Ala Gly Asn Val Asp
                 85                  90                  95

Asn Ser Phe Gly Gly Gly Thr Glu Val Val Val Lys
            100                 105
```

<210> SEQ ID NO 91
<211> LENGTH: 109
<212> TYPE: PRT
<213> ORGANISM: Oryctolagus cuniculus

<400> SEQUENCE: 91

```
Asp Met Thr Gln Thr Pro Ala Ser Val Ser Glu Pro Val Gly Gly Thr
  1               5                  10                  15
```

```
Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Arg
        35                  40                  45

Ala Ser Thr Leu Ala Ser Gly Val Ser Ser Arg Phe Lys Gly Ser Gly
    50                  55                  60

Ser Gly Thr Gln Phe Thr Leu Thr Ile Ser Asp Leu Glu Cys Ala Asp
65                  70                  75                  80

Ala Ala Thr Tyr Tyr Cys Gln Gln Gly Tyr Ser Ala Gly Asn Val Asp
                85                  90                  95

Lys His Val Phe Gly Gly Gly Thr Glu Val Val Val Lys
            100                 105

<210> SEQ ID NO 92
<211> LENGTH: 109
<212> TYPE: PRT
<213> ORGANISM: Oryctolagus cuniculus

<400> SEQUENCE: 92

Asp Met Thr Gln Thr Pro Ala Ser Val Ser Asp Pro Val Gly Gly Thr
1               5                   10                  15

Val Thr Ile Lys Cys Gln Ala Ser Gln Asn Ile Gly Ser Asn Leu Ala
            20                  25                  30

Trp Tyr Gln Gln Lys Pro Gly Gln Arg Pro Lys Leu Leu Ile Tyr Arg
        35                  40                  45

Ala Ser Thr Leu Ala Ser Gly Val Ser Ser Arg Phe Lys Gly Ser Gly
    50                  55                  60

Ser Gly Thr Gln Phe Thr Leu Thr Ile Ser Asp Leu Glu Cys Ala Asp
65                  70                  75                  80

Ala Ala Thr Tyr Tyr Cys Gln Gln Gly Tyr Ser Ala Gly Asn Val Asp
                85                  90                  95

Asn Asn Ala Phe Gly Gly Gly Thr Glu Val Val Val Lys
            100                 105

<210> SEQ ID NO 93
<211> LENGTH: 108
<212> TYPE: PRT
<213> ORGANISM: Oryctolagus cuniculus

<400> SEQUENCE: 93

Asp Met Thr Gln Thr Pro Ala Ser Val Glu Val Ala Val Gly Gly Thr
1               5                   10                  15

Val Thr Ile Asn Cys Gln Ala Ser Gln Asn Ile Gly Ser Asn Leu Ala
            20                  25                  30

Trp Tyr Gln Gln Lys Pro Gly Pro Pro Lys Leu Leu Ile Tyr Lys
        35                  40                  45

Ala Ser Thr Leu Ala Ser Gly Val Pro Ser Arg Leu Lys Gly Ser Gly
    50                  55                  60

Ser Gly Thr Glu Phe Thr Leu Thr Ile Ser Gly Val Gln Cys Asp Asp
65                  70                  75                  80

Ala Ala Thr Tyr Tyr Cys Gln Gln Gly Tyr Thr Thr Gly Asn Val Asp
                85                  90                  95

Asn Pro Phe Gly Gly Gly Thr Glu Val Val Val Lys
            100                 105

<210> SEQ ID NO 94
```

```
<211> LENGTH: 5
<212> TYPE: PRT
<213> ORGANISM: Oryctolagus cuniculus

<400> SEQUENCE: 94

Gly Asn Gly Met Ser
1               5

<210> SEQ ID NO 95
<211> LENGTH: 5
<212> TYPE: PRT
<213> ORGANISM: Oryctolagus cuniculus

<400> SEQUENCE: 95

Ile Tyr Glu Ile Ser
1               5

<210> SEQ ID NO 96
<211> LENGTH: 5
<212> TYPE: PRT
<213> ORGANISM: Oryctolagus cuniculus

<400> SEQUENCE: 96

Lys Tyr Glu Ile Asn
1               5

<210> SEQ ID NO 97
<211> LENGTH: 5
<212> TYPE: PRT
<213> ORGANISM: Oryctolagus cuniculus

<400> SEQUENCE: 97

Asn Asp Val Met Ser
1               5

<210> SEQ ID NO 98
<211> LENGTH: 5
<212> TYPE: PRT
<213> ORGANISM: Oryctolagus cuniculus

<400> SEQUENCE: 98

Asn Ile Gly Met Ser
1               5

<210> SEQ ID NO 99
<211> LENGTH: 5
<212> TYPE: PRT
<213> ORGANISM: Oryctolagus cuniculus

<400> SEQUENCE: 99

Asn Asn Ala Ile Asn
1               5

<210> SEQ ID NO 100
<211> LENGTH: 5
<212> TYPE: PRT
<213> ORGANISM: Oryctolagus cuniculus

<400> SEQUENCE: 100

Asn Asn Ala Met Ser
1               5

<210> SEQ ID NO 101
<211> LENGTH: 5
<212> TYPE: PRT
```

```
<213> ORGANISM: Oryctolagus cuniculus

<400> SEQUENCE: 101

Asn Tyr Glu Ile Asn
1               5

<210> SEQ ID NO 102
<211> LENGTH: 5
<212> TYPE: PRT
<213> ORGANISM: Oryctolagus cuniculus

<400> SEQUENCE: 102

Asn Tyr Glu Met Asn
1               5

<210> SEQ ID NO 103
<211> LENGTH: 5
<212> TYPE: PRT
<213> ORGANISM: Oryctolagus cuniculus

<400> SEQUENCE: 103

Arg Asn Ala Leu Ser
1               5

<210> SEQ ID NO 104
<211> LENGTH: 5
<212> TYPE: PRT
<213> ORGANISM: Oryctolagus cuniculus

<400> SEQUENCE: 104

Arg Asn Ala Met Ser
1               5

<210> SEQ ID NO 105
<211> LENGTH: 6
<212> TYPE: PRT
<213> ORGANISM: Oryctolagus cuniculus

<400> SEQUENCE: 105

Arg Tyr Gly Tyr Met Cys
1               5

<210> SEQ ID NO 106
<211> LENGTH: 4
<212> TYPE: PRT
<213> ORGANISM: Oryctolagus cuniculus

<400> SEQUENCE: 106

Arg Tyr Val Cys
1

<210> SEQ ID NO 107
<211> LENGTH: 5
<212> TYPE: PRT
<213> ORGANISM: Oryctolagus cuniculus

<400> SEQUENCE: 107

Ser Asp Gly Met Ser
1               5

<210> SEQ ID NO 108
<211> LENGTH: 5
<212> TYPE: PRT
<213> ORGANISM: Oryctolagus cuniculus
```

```
<400> SEQUENCE: 108

Ser Asp Val Ile Ser
1               5

<210> SEQ ID NO 109
<211> LENGTH: 5
<212> TYPE: PRT
<213> ORGANISM: Oryctolagus cuniculus

<400> SEQUENCE: 109

Ser Asp Val Met Ser
1               5

<210> SEQ ID NO 110
<211> LENGTH: 5
<212> TYPE: PRT
<213> ORGANISM: Oryctolagus cuniculus

<400> SEQUENCE: 110

Ser Gly Val Val Ser
1               5

<210> SEQ ID NO 111
<211> LENGTH: 5
<212> TYPE: PRT
<213> ORGANISM: Oryctolagus cuniculus

<400> SEQUENCE: 111

Ser Asn Ala Met Ser
1               5

<210> SEQ ID NO 112
<211> LENGTH: 5
<212> TYPE: PRT
<213> ORGANISM: Oryctolagus cuniculus

<400> SEQUENCE: 112

Ser Asn Gly Met Ser
1               5

<210> SEQ ID NO 113
<211> LENGTH: 5
<212> TYPE: PRT
<213> ORGANISM: Oryctolagus cuniculus

<400> SEQUENCE: 113

Ser Ser Leu Met Thr
1               5

<210> SEQ ID NO 114
<211> LENGTH: 5
<212> TYPE: PRT
<213> ORGANISM: Oryctolagus cuniculus

<400> SEQUENCE: 114

Thr Asp Val Ile Ser
1               5

<210> SEQ ID NO 115
<211> LENGTH: 5
<212> TYPE: PRT
<213> ORGANISM: Oryctolagus cuniculus

<400> SEQUENCE: 115
```

Thr Asp Val Leu Ser
1               5

<210> SEQ ID NO 116
<211> LENGTH: 5
<212> TYPE: PRT
<213> ORGANISM: Oryctolagus cuniculus

<400> SEQUENCE: 116

Thr Asp Val Val Ser
1               5

<210> SEQ ID NO 117
<211> LENGTH: 5
<212> TYPE: PRT
<213> ORGANISM: Oryctolagus cuniculus

<400> SEQUENCE: 117

Thr Asn Ala Met Ser
1               5

<210> SEQ ID NO 118
<211> LENGTH: 5
<212> TYPE: PRT
<213> ORGANISM: Oryctolagus cuniculus

<400> SEQUENCE: 118

Thr Asn Gly Met Ser
1               5

<210> SEQ ID NO 119
<211> LENGTH: 5
<212> TYPE: PRT
<213> ORGANISM: Oryctolagus cuniculus

<400> SEQUENCE: 119

Thr Asn Leu Ile Asn
1               5

<210> SEQ ID NO 120
<211> LENGTH: 6
<212> TYPE: PRT
<213> ORGANISM: Oryctolagus cuniculus

<400> SEQUENCE: 120

Thr Tyr Tyr Tyr Met Cys
1               5

<210> SEQ ID NO 121
<211> LENGTH: 18
<212> TYPE: PRT
<213> ORGANISM: Oryctolagus cuniculus

<400> SEQUENCE: 121

Cys Ile Ala Ala Gly Ser Ser Gly Tyr Thr Tyr Tyr Ala Ser Trp Ala
1               5                   10                  15

Lys Gly

<210> SEQ ID NO 122
<211> LENGTH: 18
<212> TYPE: PRT
<213> ORGANISM: Oryctolagus cuniculus

<400> SEQUENCE: 122

Cys Ile His Ala Gly Arg Ser Gly Arg Thr Tyr Tyr Ala Asn Trp Ala
1               5                   10                  15

Lys Gly

<210> SEQ ID NO 123
<211> LENGTH: 17
<212> TYPE: PRT
<213> ORGANISM: Oryctolagus cuniculus

<400> SEQUENCE: 123

Cys Ile Tyr Thr Gly Arg Ala Ser Thr Tyr Tyr Ala Thr Trp Ala Lys
1               5                   10                  15

Gly

<210> SEQ ID NO 124
<211> LENGTH: 16
<212> TYPE: PRT
<213> ORGANISM: Oryctolagus cuniculus

<400> SEQUENCE: 124

Tyr Ala Trp Ser Gly Gly Ala Thr Tyr Tyr Ala Ser Trp Ala Lys Gly
1               5                   10                  15

<210> SEQ ID NO 125
<211> LENGTH: 16
<212> TYPE: PRT
<213> ORGANISM: Oryctolagus cuniculus

<400> SEQUENCE: 125

Tyr Ala Trp Ser Gly Gly Pro Thr Tyr Tyr Ala Asn Trp Ala Lys Gly
1               5                   10                  15

<210> SEQ ID NO 126
<211> LENGTH: 16
<212> TYPE: PRT
<213> ORGANISM: Oryctolagus cuniculus

<400> SEQUENCE: 126

Tyr Gly Trp Ser Gly Gly Pro Thr Tyr Tyr Ala Asn Trp Ala Lys Gly
1               5                   10                  15

<210> SEQ ID NO 127
<211> LENGTH: 16
<212> TYPE: PRT
<213> ORGANISM: Oryctolagus cuniculus

<400> SEQUENCE: 127

Tyr Ile Asp Val Gly Ser Gly Thr Trp Tyr Ala Ser Trp Ala Lys Gly
1               5                   10                  15

<210> SEQ ID NO 128
<211> LENGTH: 16
<212> TYPE: PRT
<213> ORGANISM: Oryctolagus cuniculus

<400> SEQUENCE: 128

Tyr Ile Gly Val Gly Gly Val Thr Tyr Tyr Ala Asn Trp Ala Lys Ser
1               5                   10                  15

<210> SEQ ID NO 129
<211> LENGTH: 16
<212> TYPE: PRT
<213> ORGANISM: Oryctolagus cuniculus

<400> SEQUENCE: 129

Tyr Ile Asn Tyr Gly Ala Ser Ala Tyr Ala Asn Trp Ala Lys Gly
1               5                   10                  15

<210> SEQ ID NO 130
<211> LENGTH: 16
<212> TYPE: PRT
<213> ORGANISM: Oryctolagus cuniculus

<400> SEQUENCE: 130

Tyr Ile Trp Ser Gly Gly Ala Pro Phe Tyr Ala Ser Trp Ala Lys Gly
1               5                   10                  15

<210> SEQ ID NO 131
<211> LENGTH: 16
<212> TYPE: PRT
<213> ORGANISM: Oryctolagus cuniculus

<400> SEQUENCE: 131

Tyr Ile Trp Ser Gly Gly Arg Pro Tyr Tyr Ala Asn Trp Ala Lys Gly
1               5                   10                  15

<210> SEQ ID NO 132
<211> LENGTH: 16
<212> TYPE: PRT
<213> ORGANISM: Oryctolagus cuniculus

<400> SEQUENCE: 132

Tyr Ile Trp Ser Gly Gly Ser Pro Tyr Tyr Ala Asn Trp Ala Lys Gly
1               5                   10                  15

<210> SEQ ID NO 133
<211> LENGTH: 16
<212> TYPE: PRT
<213> ORGANISM: Oryctolagus cuniculus

<400> SEQUENCE: 133

Tyr Ile Tyr Ala Gly Ser Ser Pro Tyr Tyr Ala Asn Trp Ala Lys Gly
1               5                   10                  15

<210> SEQ ID NO 134
<211> LENGTH: 16
<212> TYPE: PRT
<213> ORGANISM: Oryctolagus cuniculus

<400> SEQUENCE: 134

Tyr Ile Tyr Pro Gly Gly Ala Pro His Tyr Ala Ser Trp Ala Lys Gly
1               5                   10                  15

<210> SEQ ID NO 135
<211> LENGTH: 16
<212> TYPE: PRT
<213> ORGANISM: Oryctolagus cuniculus

<400> SEQUENCE: 135

Tyr Ile Tyr Pro Gly Gly Ser Pro Tyr Tyr Ala Asn Trp Ala Lys Gly
1               5                   10                  15

<210> SEQ ID NO 136
<211> LENGTH: 16
<212> TYPE: PRT
<213> ORGANISM: Oryctolagus cuniculus

<400> SEQUENCE: 136

Tyr Ile Tyr Ser Gly Gly Ser Pro Tyr Tyr Ala Asn Trp Ala Lys Gly
1               5                   10                  15

<210> SEQ ID NO 137
<211> LENGTH: 16
<212> TYPE: PRT
<213> ORGANISM: Oryctolagus cuniculus

<400> SEQUENCE: 137

Tyr Ile Tyr Ser Gly Gly Ser Pro Tyr Tyr Ala Ser Trp Ala Lys Gly
1               5                   10                  15

<210> SEQ ID NO 138
<211> LENGTH: 16
<212> TYPE: PRT
<213> ORGANISM: Oryctolagus cuniculus

<400> SEQUENCE: 138

Tyr Ile Tyr Ser Gly Ser Ser Pro Tyr Tyr Ala Asn Trp Ala Lys Gly
1               5                   10                  15

<210> SEQ ID NO 139
<211> LENGTH: 16
<212> TYPE: PRT
<213> ORGANISM: Oryctolagus cuniculus

<400> SEQUENCE: 139

Tyr Ile Tyr Ser Gly Ser Ser Pro Tyr Tyr Ala Ser Trp Ala Lys Gly
1               5                   10                  15

<210> SEQ ID NO 140
<211> LENGTH: 16
<212> TYPE: PRT
<213> ORGANISM: Oryctolagus cuniculus

<400> SEQUENCE: 140

Tyr Thr Trp Asn Gly Gly Ala Thr Phe Tyr Ala Ser Trp Ala Lys Gly
1               5                   10                  15

<210> SEQ ID NO 141
<211> LENGTH: 16
<212> TYPE: PRT
<213> ORGANISM: Oryctolagus cuniculus

<400> SEQUENCE: 141

Tyr Thr Trp Asn Gly Gly Ala Thr Tyr Tyr Ala Ser Trp Ala Lys Gly
1               5                   10                  15

<210> SEQ ID NO 142
<211> LENGTH: 16
<212> TYPE: PRT
<213> ORGANISM: Oryctolagus cuniculus

<400> SEQUENCE: 142

Tyr Thr Trp Ser Gly Gly Gly Thr Tyr Cys Ala Ser Trp Ala Lys Gly
1               5                   10                  15

<210> SEQ ID NO 143
<211> LENGTH: 16
<212> TYPE: PRT
<213> ORGANISM: Oryctolagus cuniculus

<400> SEQUENCE: 143

Tyr Thr Trp Ser Gly Gly Ser Thr Tyr Tyr Ala Ile Trp Ala Lys Gly
1               5                   10                  15

<210> SEQ ID NO 144
<211> LENGTH: 16
<212> TYPE: PRT
<213> ORGANISM: Oryctolagus cuniculus

<400> SEQUENCE: 144

Tyr Thr Trp Ser Gly Gly Ser Thr Tyr Tyr Ala Asn Trp Ala Lys Gly
1               5                   10                  15

<210> SEQ ID NO 145
<211> LENGTH: 16
<212> TYPE: PRT
<213> ORGANISM: Oryctolagus cuniculus

<400> SEQUENCE: 145

Tyr Thr Trp Ser Gly Gly Ser Thr Tyr Tyr Ala Ser Trp Ala Lys Gly
1               5                   10                  15

<210> SEQ ID NO 146
<211> LENGTH: 11
<212> TYPE: PRT
<213> ORGANISM: Oryctolagus cuniculus

<400> SEQUENCE: 146

Ala Tyr Asp Ser Glu Trp Asp Arg Leu Asp Leu
1               5                   10

<210> SEQ ID NO 147
<211> LENGTH: 9
<212> TYPE: PRT
<213> ORGANISM: Oryctolagus cuniculus

<400> SEQUENCE: 147

Gly Phe Gly Ser Ser Gly Leu Asn Ile
1               5

<210> SEQ ID NO 148
<211> LENGTH: 7
<212> TYPE: PRT
<213> ORGANISM: Oryctolagus cuniculus

<400> SEQUENCE: 148

Gly Phe Asn Pro Phe Asp Pro
1               5

<210> SEQ ID NO 149
<211> LENGTH: 11
<212> TYPE: PRT
<213> ORGANISM: Oryctolagus cuniculus

<400> SEQUENCE: 149

Gly Tyr Gly Asn Asp Trp Asp Arg Leu Asp Leu
1               5                   10

<210> SEQ ID NO 150
<211> LENGTH: 7
<212> TYPE: PRT
<213> ORGANISM: Oryctolagus cuniculus

<400> SEQUENCE: 150

Gly Tyr Asn Gly Met Asp Pro
1               5

<210> SEQ ID NO 151
<211> LENGTH: 7
<212> TYPE: PRT
<213> ORGANISM: Oryctolagus cuniculus

<400> SEQUENCE: 151

Gly Tyr Asn Pro Phe Asp Leu
1               5

<210> SEQ ID NO 152
<211> LENGTH: 11
<212> TYPE: PRT
<213> ORGANISM: Oryctolagus cuniculus

<400> SEQUENCE: 152

His Ala Lys Gly Gly Gly Trp Tyr Leu Asp Ile
1               5                   10

<210> SEQ ID NO 153
<211> LENGTH: 11
<212> TYPE: PRT
<213> ORGANISM: Oryctolagus cuniculus

<400> SEQUENCE: 153

His Ala Ser Asp Gly Gly Trp Tyr Leu Asp Ile
1               5                   10

<210> SEQ ID NO 154
<211> LENGTH: 11
<212> TYPE: PRT
<213> ORGANISM: Oryctolagus cuniculus

<400> SEQUENCE: 154

His Ala Ser Gly Gly Gly Trp Tyr Leu Ala Ile
1               5                   10

<210> SEQ ID NO 155
<211> LENGTH: 11
<212> TYPE: PRT
<213> ORGANISM: Oryctolagus cuniculus

<400> SEQUENCE: 155

His Ala Ser Gly Gly Gly Trp Tyr Leu Asp Ile
1               5                   10

<210> SEQ ID NO 156
<211> LENGTH: 11
<212> TYPE: PRT
<213> ORGANISM: Oryctolagus cuniculus

<400> SEQUENCE: 156

His Leu Ser Gly Gly Gly Trp Tyr Leu Asp Ile
1               5                   10

<210> SEQ ID NO 157
<211> LENGTH: 11
<212> TYPE: PRT
<213> ORGANISM: Oryctolagus cuniculus

<400> SEQUENCE: 157

His Thr Ser Gly Gly Gly Trp Tyr Leu Asp Ile
1               5                   10

<210> SEQ ID NO 158
<211> LENGTH: 11

<212> TYPE: PRT
<213> ORGANISM: Oryctolagus cuniculus

<400> SEQUENCE: 158

His Val Ser Asp Gly Gly Trp Tyr Leu Asp Ile
1               5                   10

<210> SEQ ID NO 159
<211> LENGTH: 11
<212> TYPE: PRT
<213> ORGANISM: Oryctolagus cuniculus

<400> SEQUENCE: 159

His Val Ser Asp Gly Gly Trp Tyr Leu Tyr Ile
1               5                   10

<210> SEQ ID NO 160
<211> LENGTH: 11
<212> TYPE: PRT
<213> ORGANISM: Oryctolagus cuniculus

<400> SEQUENCE: 160

His Val Ser Gly Gly Gly Trp Tyr Leu Asp Ile
1               5                   10

<210> SEQ ID NO 161
<211> LENGTH: 12
<212> TYPE: PRT
<213> ORGANISM: Oryctolagus cuniculus

<400> SEQUENCE: 161

Lys Ala Gly Asp Ile Trp Tyr Tyr Gly Met Asp Leu
1               5                   10

<210> SEQ ID NO 162
<211> LENGTH: 7
<212> TYPE: PRT
<213> ORGANISM: Oryctolagus cuniculus

<400> SEQUENCE: 162

Lys Tyr Asn Pro Met Asp Leu
1               5

<210> SEQ ID NO 163
<211> LENGTH: 7
<212> TYPE: PRT
<213> ORGANISM: Oryctolagus cuniculus

<400> SEQUENCE: 163

Gln Tyr Asn Pro Met Asp Leu
1               5

<210> SEQ ID NO 164
<211> LENGTH: 12
<212> TYPE: PRT
<213> ORGANISM: Oryctolagus cuniculus

<400> SEQUENCE: 164

Arg Tyr Thr Asp Ser Gly Phe Asp Ala Leu Asp Pro
1               5                   10

<210> SEQ ID NO 165
<211> LENGTH: 11
<212> TYPE: PRT
<213> ORGANISM: Oryctolagus cuniculus

<400> SEQUENCE: 165

Ser Gly Asp Ser Tyr Val Gly Tyr Phe Ala Leu
1               5                   10

<210> SEQ ID NO 166
<211> LENGTH: 11
<212> TYPE: PRT
<213> ORGANISM: Oryctolagus cuniculus

<400> SEQUENCE: 166

Ser Gly Asp Ser Tyr Val Gly Tyr Phe Asn Leu
1               5                   10

<210> SEQ ID NO 167
<211> LENGTH: 7
<212> TYPE: PRT
<213> ORGANISM: Oryctolagus cuniculus

<400> SEQUENCE: 167

Ser Tyr Asn Pro Met Asp Leu
1               5

<210> SEQ ID NO 168
<211> LENGTH: 14
<212> TYPE: PRT
<213> ORGANISM: Oryctolagus cuniculus

<400> SEQUENCE: 168

Gly Arg His Ser His His Gln Leu Pro Gly Gln Ser Glu His
1               5                   10

<210> SEQ ID NO 169
<211> LENGTH: 11
<212> TYPE: PRT
<213> ORGANISM: Oryctolagus cuniculus

<400> SEQUENCE: 169

Gln Ala Ser Glu Asn Ile Tyr Asn Tyr Leu Ser
1               5                   10

<210> SEQ ID NO 170
<211> LENGTH: 11
<212> TYPE: PRT
<213> ORGANISM: Oryctolagus cuniculus

<400> SEQUENCE: 170

Gln Ala Ser Gln Asn Ile Gly Ser Asn Phe Ala
1               5                   10

<210> SEQ ID NO 171
<211> LENGTH: 11
<212> TYPE: PRT
<213> ORGANISM: Oryctolagus cuniculus

<400> SEQUENCE: 171

Gln Ala Ser Gln Asn Ile Gly Ser Asn Leu Ala
1               5                   10

<210> SEQ ID NO 172
<211> LENGTH: 11
<212> TYPE: PRT
<213> ORGANISM: Oryctolagus cuniculus

<400> SEQUENCE: 172

Gln Ala Ser Gln Asn Ile Gly Tyr Asn Leu Ala
1               5                   10

<210> SEQ ID NO 173
<211> LENGTH: 11
<212> TYPE: PRT
<213> ORGANISM: Oryctolagus cuniculus

<400> SEQUENCE: 173

Gln Ala Ser Gln Asn Ile Tyr Asn Tyr Leu Ala
1               5                   10

<210> SEQ ID NO 174
<211> LENGTH: 11
<212> TYPE: PRT
<213> ORGANISM: Oryctolagus cuniculus

<400> SEQUENCE: 174

Gln Ala Ser Gln Ser Ile Gly Ser Asn Leu Ala
1               5                   10

<210> SEQ ID NO 175
<211> LENGTH: 11
<212> TYPE: PRT
<213> ORGANISM: Oryctolagus cuniculus

<400> SEQUENCE: 175

Gln Ala Ser Gln Ser Ile Gly Ser Asn Leu Gly
1               5                   10

<210> SEQ ID NO 176
<211> LENGTH: 11
<212> TYPE: PRT
<213> ORGANISM: Oryctolagus cuniculus

<400> SEQUENCE: 176

Gln Ala Ser Gln Ser Ile Gly Ser Tyr Leu Ser
1               5                   10

<210> SEQ ID NO 177
<211> LENGTH: 7
<212> TYPE: PRT
<213> ORGANISM: Oryctolagus cuniculus

<400> SEQUENCE: 177

Glu Ala Ser Lys Leu Ala Ser
1               5

<210> SEQ ID NO 178
<211> LENGTH: 7
<212> TYPE: PRT
<213> ORGANISM: Oryctolagus cuniculus

<400> SEQUENCE: 178

Gly Ala Ser Thr Leu Ala Ser
1               5

<210> SEQ ID NO 179
<211> LENGTH: 7
<212> TYPE: PRT
<213> ORGANISM: Oryctolagus cuniculus

<400> SEQUENCE: 179

Gly Thr Ser Thr Leu Ala Ser

```
<210> SEQ ID NO 180
<211> LENGTH: 7
<212> TYPE: PRT
<213> ORGANISM: Oryctolagus cuniculus

<400> SEQUENCE: 180

Lys Ala Ser Thr Leu Ala Ser
1               5

<210> SEQ ID NO 181
<211> LENGTH: 7
<212> TYPE: PRT
<213> ORGANISM: Oryctolagus cuniculus

<400> SEQUENCE: 181

Leu Ala Ser Thr Leu Pro Ser
1               5

<210> SEQ ID NO 182
<211> LENGTH: 7
<212> TYPE: PRT
<213> ORGANISM: Oryctolagus cuniculus

<400> SEQUENCE: 182

Pro Asp Leu Trp Cys Ile His
1               5

<210> SEQ ID NO 183
<211> LENGTH: 7
<212> TYPE: PRT
<213> ORGANISM: Oryctolagus cuniculus

<400> SEQUENCE: 183

Arg Ala Ser Thr Leu Ala Ser
1               5

<210> SEQ ID NO 184
<211> LENGTH: 7
<212> TYPE: PRT
<213> ORGANISM: Oryctolagus cuniculus

<400> SEQUENCE: 184

Ser Ala Ser Ile Leu Ala Ser
1               5

<210> SEQ ID NO 185
<211> LENGTH: 7
<212> TYPE: PRT
<213> ORGANISM: Oryctolagus cuniculus

<400> SEQUENCE: 185

Ser Ala Ser Asn Leu Ala Ser
1               5

<210> SEQ ID NO 186
<211> LENGTH: 7
<212> TYPE: PRT
<213> ORGANISM: Oryctolagus cuniculus

<400> SEQUENCE: 186

Ser Ala Ser Asn Leu Glu Ser
1               5
```

<210> SEQ ID NO 187
<211> LENGTH: 7
<212> TYPE: PRT
<213> ORGANISM: Oryctolagus cuniculus

<400> SEQUENCE: 187

Ser Ala Ser Thr Leu Ala Ser
1               5

<210> SEQ ID NO 188
<211> LENGTH: 7
<212> TYPE: PRT
<213> ORGANISM: Oryctolagus cuniculus

<400> SEQUENCE: 188

Ser Thr Ser Thr Val Ala Ser
1               5

<210> SEQ ID NO 189
<211> LENGTH: 12
<212> TYPE: PRT
<213> ORGANISM: Oryctolagus cuniculus

<400> SEQUENCE: 189

Gln Gln Ala Tyr Ser Ile Ser Asn Val Asp Asn Pro
1               5                   10

<210> SEQ ID NO 190
<211> LENGTH: 14
<212> TYPE: PRT
<213> ORGANISM: Oryctolagus cuniculus

<400> SEQUENCE: 190

Cys His Leu Leu Leu Ser Thr Gly Ile Cys Ala Cys Arg Cys
1               5                   10

<210> SEQ ID NO 191
<211> LENGTH: 12
<212> TYPE: PRT
<213> ORGANISM: Oryctolagus cuniculus

<400> SEQUENCE: 191

Gln Gln Gly Tyr Ser Val Gly Asn Ile Asp Asn Ala
1               5                   10

<210> SEQ ID NO 192
<211> LENGTH: 12
<212> TYPE: PRT
<213> ORGANISM: Oryctolagus cuniculus

<400> SEQUENCE: 192

Gln Gln Ala Tyr Ser Val Ser Asn Val Asp Asn Ala
1               5                   10

<210> SEQ ID NO 193
<211> LENGTH: 12
<212> TYPE: PRT
<213> ORGANISM: Oryctolagus cuniculus

<400> SEQUENCE: 193

Gln Gln Gly Tyr Ser Ala Gly Asn Val Asn Asn Pro
1               5                   10

<210> SEQ ID NO 194

```
<211> LENGTH: 12
<212> TYPE: PRT
<213> ORGANISM: Oryctolagus cuniculus

<400> SEQUENCE: 194

Gln Gln Gly Tyr Thr Thr Lys Asp Leu Val Asn Pro
1               5                   10

<210> SEQ ID NO 195
<211> LENGTH: 12
<212> TYPE: PRT
<213> ORGANISM: Oryctolagus cuniculus

<400> SEQUENCE: 195

Gln Gln Gly Tyr Thr Thr Lys Asn Val Val Asn Pro
1               5                   10

<210> SEQ ID NO 196
<211> LENGTH: 12
<212> TYPE: PRT
<213> ORGANISM: Oryctolagus cuniculus

<400> SEQUENCE: 196

Gln Gln Ala Tyr Ser Ile Ser Asn Val Asp Asn Ala
1               5                   10

<210> SEQ ID NO 197
<211> LENGTH: 11
<212> TYPE: PRT
<213> ORGANISM: Oryctolagus cuniculus

<400> SEQUENCE: 197

Gln Gln Gly Tyr Thr Thr Asn Ala Asp Asn Ile
1               5                   10

<210> SEQ ID NO 198
<211> LENGTH: 12
<212> TYPE: PRT
<213> ORGANISM: Oryctolagus cuniculus

<400> SEQUENCE: 198

Gln Gln Gly Tyr Thr Thr Asn Asn Val Leu Asn Ala
1               5                   10

<210> SEQ ID NO 199
<211> LENGTH: 12
<212> TYPE: PRT
<213> ORGANISM: Oryctolagus cuniculus

<400> SEQUENCE: 199

Gln Gln Ala Tyr Ser Ile Ser Asn Val Asp Asn Ala
1               5                   10

<210> SEQ ID NO 200
<211> LENGTH: 12
<212> TYPE: PRT
<213> ORGANISM: Oryctolagus cuniculus

<400> SEQUENCE: 200

Gln Gln Gly Tyr Ser Val Gly Asn Val Asn Asn Ala
1               5                   10

<210> SEQ ID NO 201
<211> LENGTH: 12
<212> TYPE: PRT
```

<213> ORGANISM: Oryctolagus cuniculus

<400> SEQUENCE: 201

Gln Gln Gly Tyr Ser Ala Gly Asn Val Asn Asn Pro
1               5                   10

<210> SEQ ID NO 202
<211> LENGTH: 12
<212> TYPE: PRT
<213> ORGANISM: Oryctolagus cuniculus

<400> SEQUENCE: 202

Gln Gln Ala Tyr Ser Thr Ser Lys Ile Asp Asn Ala
1               5                   10

<210> SEQ ID NO 203
<211> LENGTH: 12
<212> TYPE: PRT
<213> ORGANISM: Oryctolagus cuniculus

<400> SEQUENCE: 203

Gln Gln Ala Tyr Ser Ile Ser Asn Val Glu Asn Pro
1               5                   10

<210> SEQ ID NO 204
<211> LENGTH: 12
<212> TYPE: PRT
<213> ORGANISM: Oryctolagus cuniculus

<400> SEQUENCE: 204

Gln Gln Gly Tyr Ser Val Gly Asn Val Asn Asn Ala
1               5                   10

<210> SEQ ID NO 205
<211> LENGTH: 12
<212> TYPE: PRT
<213> ORGANISM: Oryctolagus cuniculus

<400> SEQUENCE: 205

Gln Gln Gly Tyr Ser Val Ser Asn Ile Asp Asn Ala
1               5                   10

<210> SEQ ID NO 206
<211> LENGTH: 11
<212> TYPE: PRT
<213> ORGANISM: Oryctolagus cuniculus

<400> SEQUENCE: 206

Gln Gln Gly Tyr Ser Ala Asn Val Asp Asn Ala
1               5                   10

<210> SEQ ID NO 207
<211> LENGTH: 12
<212> TYPE: PRT
<213> ORGANISM: Oryctolagus cuniculus

<400> SEQUENCE: 207

Gln Gln Ala Tyr Ser Val Gly Asn Val Asp Asn Ala
1               5                   10

<210> SEQ ID NO 208
<211> LENGTH: 12
<212> TYPE: PRT
<213> ORGANISM: Oryctolagus cuniculus

<400> SEQUENCE: 208

Gln Gln Gly Tyr Ser Val Gly Asn Val Asn Asn Ala
1               5                   10

<210> SEQ ID NO 209
<211> LENGTH: 12
<212> TYPE: PRT
<213> ORGANISM: Oryctolagus cuniculus

<400> SEQUENCE: 209

Gln Gln Ala Tyr Thr Ala Ser Asn Val Asp Asn Ala
1               5                   10

<210> SEQ ID NO 210
<211> LENGTH: 14
<212> TYPE: PRT
<213> ORGANISM: Oryctolagus cuniculus

<400> SEQUENCE: 210

Gln Ser Tyr Tyr Asp Ser Ser Arg Ile Ser Tyr Gly Ser Ala
1               5                   10

<210> SEQ ID NO 211
<211> LENGTH: 12
<212> TYPE: PRT
<213> ORGANISM: Oryctolagus cuniculus

<400> SEQUENCE: 211

Gln Gln Gly Tyr Thr Thr Lys Asp Val Val Asn Pro
1               5                   10

<210> SEQ ID NO 212
<211> LENGTH: 12
<212> TYPE: PRT
<213> ORGANISM: Oryctolagus cuniculus

<400> SEQUENCE: 212

Gln Gln Gly Tyr Thr Thr Lys Asn Val Val Asn Pro
1               5                   10

<210> SEQ ID NO 213
<211> LENGTH: 12
<212> TYPE: PRT
<213> ORGANISM: Oryctolagus cuniculus

<400> SEQUENCE: 213

Gln Gln Gly Tyr Ser Val Gly Asn Val Asn Asn Ala
1               5                   10

<210> SEQ ID NO 214
<211> LENGTH: 12
<212> TYPE: PRT
<213> ORGANISM: Oryctolagus cuniculus

<400> SEQUENCE: 214

Gln Gln Ala Tyr Ser Ile Ser Asn Val Asp Asn Ala
1               5                   10

<210> SEQ ID NO 215
<211> LENGTH: 12
<212> TYPE: PRT
<213> ORGANISM: Oryctolagus cuniculus

<400> SEQUENCE: 215

Gln Gln Ala Tyr Ser Val Gly Asn Val Asp Asn Ala
1               5                   10

<210> SEQ ID NO 216
<211> LENGTH: 14
<212> TYPE: PRT
<213> ORGANISM: Oryctolagus cuniculus

<400> SEQUENCE: 216

Gln Ser Tyr Tyr Asp Val Thr Ser His Ser Tyr Asp Asn Pro
1               5                   10

<210> SEQ ID NO 217
<211> LENGTH: 12
<212> TYPE: PRT
<213> ORGANISM: Oryctolagus cuniculus

<400> SEQUENCE: 217

Gln Gln Gly Tyr Ser Val Gly Asn Val Asn Asn Ala
1               5                   10

<210> SEQ ID NO 218
<211> LENGTH: 12
<212> TYPE: PRT
<213> ORGANISM: Oryctolagus cuniculus

<400> SEQUENCE: 218

Gln Gln Ala Tyr Ser Ile Ser Asn Val Asp Asn Ala
1               5                   10

<210> SEQ ID NO 219
<211> LENGTH: 12
<212> TYPE: PRT
<213> ORGANISM: Oryctolagus cuniculus

<400> SEQUENCE: 219

Gln Gln Ala Tyr Thr Ile Ser Asn Val Asp Asn Ala
1               5                   10

<210> SEQ ID NO 220
<211> LENGTH: 13
<212> TYPE: PRT
<213> ORGANISM: Oryctolagus cuniculus

<400> SEQUENCE: 220

Gln Gln Gly Tyr Ser Ala Gly Asn Val Asp Asn Asn Thr
1               5                   10

<210> SEQ ID NO 221
<211> LENGTH: 12
<212> TYPE: PRT
<213> ORGANISM: Oryctolagus cuniculus

<400> SEQUENCE: 221

Gln Gln Gly Tyr Ser Ala Gly Asn Val Asp Asn Asn
1               5                   10

<210> SEQ ID NO 222
<211> LENGTH: 12
<212> TYPE: PRT
<213> ORGANISM: Oryctolagus cuniculus

<400> SEQUENCE: 222

Gln Gln Gly Tyr Ser Ala Gly Asn Val Asp Asn Ser
1               5                   10

<210> SEQ ID NO 223
<211> LENGTH: 13
<212> TYPE: PRT
<213> ORGANISM: Oryctolagus cuniculus

<400> SEQUENCE: 223

Gln Gln Gly Tyr Ser Ala Gly Asn Val Asp Lys His Val
1               5                   10

<210> SEQ ID NO 224
<211> LENGTH: 13
<212> TYPE: PRT
<213> ORGANISM: Oryctolagus cuniculus

<400> SEQUENCE: 224

Gln Gln Gly Tyr Ser Ala Gly Asn Val Asp Asn Asn Ala
1               5                   10

<210> SEQ ID NO 225
<211> LENGTH: 12
<212> TYPE: PRT
<213> ORGANISM: Oryctolagus cuniculus

<400> SEQUENCE: 225

Gln Gln Gly Tyr Thr Thr Gly Asn Val Asp Asn Pro
1               5                   10

<210> SEQ ID NO 226
<211> LENGTH: 119
<212> TYPE: PRT
<213> ORGANISM: Artificial Sequence
<220> FEATURE:
<223> OTHER INFORMATION: Humanized VH rabbit antibody clone 23

<400> SEQUENCE: 226

Gln Glu Gln Leu Val Glu Ser Gly Gly Gly Leu Val Gln Pro Gly Gly
1               5                   10                  15

Ser Leu Arg Leu Ser Cys Val Ala Ser Gly Phe Ser Leu Ser Ser Asp
            20                  25                  30

Gly Met Ser Trp Val Arg Gln Ala Pro Gly Lys Gly Leu Glu Trp Ile
        35                  40                  45

Gly Tyr Ile Tyr Ser Gly Ser Ser Pro Tyr Tyr Ala Asn Trp Ala Lys
    50                  55                  60

Gly Arg Phe Thr Ile Ser Lys Asp Ser Ser Thr Asn Thr Val Phe Leu
65                  70                  75                  80

Gln Met Asn Ser Leu Arg Ala Glu Asp Thr Ala Val Tyr Phe Cys Ala
                85                  90                  95

Arg His Gly Asp Gly Gly Trp Tyr Leu Asp Ile Trp Gly Pro Gly
            100                 105                 110

Thr Leu Val Thr Val Ser Ser
        115

<210> SEQ ID NO 227
<211> LENGTH: 110
<212> TYPE: PRT
<213> ORGANISM: Artificial Sequence
<220> FEATURE:
<223> OTHER INFORMATION: Humanized VL rabbit antibody clone 23

<400> SEQUENCE: 227

Asp Ile Gln Met Thr Gln Ser Pro Ser Ser Leu Ser Ala Ser Val Gly

```
                1               5                  10                  15
Asp Arg Val Thr Ile Asn Cys Gln Ala Ser Gln Ser Ile Gly Ser Asn
                        20                  25                  30

Leu Ala Trp Tyr Gln Gln Lys Pro Gly Lys Ala Pro Lys Leu Leu Ile
            35                  40                  45

Tyr Ala Ala Ser Thr Leu Pro Ser Gly Val Ser Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ala Tyr Ser Val Gly Asn
                85                  90                  95

Val Asp Asn Ala Phe Gly Gly Gly Thr Lys Val Glu Ile Lys
                100                 105                 110
```

<210> SEQ ID NO 228
<211> LENGTH: 11
<212> TYPE: PRT
<213> ORGANISM: Artificial Sequence
<220> FEATURE:
<223> OTHER INFORMATION: Humanized VHCDR3 rabbit antibody clone 23

<400> SEQUENCE: 228

```
His Gly Asp Gly Gly Gly Trp Tyr Leu Asp Ile
1               5                   10
```

<210> SEQ ID NO 229
<211> LENGTH: 115
<212> TYPE: PRT
<213> ORGANISM: Artificial Sequence
<220> FEATURE:
<223> OTHER INFORMATION: Humanized VH rabbit antibody clone 408

<400> SEQUENCE: 229

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Thr Asp
                20                  25                  30

Val Val Ser Trp Val Arg Gln Ala Pro Gly Lys Gly Leu Glu Trp Ile
            35                  40                  45

Gly Tyr Thr Trp Asn Gly Gly Ala Thr Phe Tyr Ala Ser Trp Ala Lys
        50                  55                  60

Gly Arg Phe Thr Phe Ser Lys Asp Ser Ser Lys Asn Thr Val Tyr Leu
65                  70                  75                  80

Gln Met Asn Ser Pro Arg Ala Glu Asp Thr Ala Val Tyr Phe Cys Ala
                85                  90                  95

Arg Gly Tyr Asn Gly Met Asp Pro Trp Gly Pro Gly Thr Leu Val Thr
                100                 105                 110

Val Ser Ser
        115
```

<210> SEQ ID NO 230
<211> LENGTH: 110
<212> TYPE: PRT
<213> ORGANISM: Artificial Sequence
<220> FEATURE:
<223> OTHER INFORMATION: Humanized VL rabbit antibody clone 408

<400> SEQUENCE: 230

```
Asp Ile Gln Met Thr Gln Ser Pro Ser Ser Leu Ser Ala Ser Val Gly
1               5                   10                  15
```

-continued

Asp Arg Val Thr Ile Lys Cys Gln Ala Ser Gln Asn Ile Gly Ser Asn
            20                  25                  30

Leu Ala Trp Tyr Gln Gln Lys Pro Gly Lys Pro Lys Leu Leu Ile
        35                  40                  45

Ser Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Thr Lys Asn
                85                  90                  95

Val Val Asn Pro Phe Gly Gly Thr Lys Val Glu Ile Lys
            100                 105                 110

<210> SEQ ID NO 231
<211> LENGTH: 115
<212> TYPE: PRT
<213> ORGANISM: Artificial Sequence
<220> FEATURE:
<223> OTHER INFORMATION: Humanized VH rabbit antibody clone EBI51-22

<400> SEQUENCE: 231

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Thr Asp
            20                  25                  30

Val Leu Ser Trp Val Arg Gln Ala Pro Gly Lys Gly Leu Glu Trp Ile
        35                  40                  45

Gly Tyr Thr Trp Ser Gly Gly Ser Thr Tyr Tyr Ala Ser Trp Ala Lys
50                  55                  60

Gly Arg Phe Thr Ile Ser Lys Asp Ser Ser Lys Asn Thr Val Tyr Leu
65                  70                  75                  80

Gln Met Asn Ser Pro Arg Ala Glu Asp Thr Ala Val Tyr Phe Cys Ala
                85                  90                  95

Arg Gly Phe Asn Pro Phe Asp Pro Trp Gly Pro Gly Thr Leu Val Thr
            100                 105                 110

Val Ser Ser
        115

<210> SEQ ID NO 232
<211> LENGTH: 111
<212> TYPE: PRT
<213> ORGANISM: Artificial Sequence
<220> FEATURE:
<223> OTHER INFORMATION: Humanized VL rabbit antibody clone EBI51-22

<400> SEQUENCE: 232

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Asn Ile Gly Ser Asn
            20                  25                  30

Leu Ala Trp Tyr Gln Gln Lys Pro Gly Lys Arg Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ala Gly Asn

```
                    85                  90                  95
Val Asp Asn Asn Ala Phe Gly Gly Gly Thr Lys Val Glu Ile Lys
                    100                 105                 110

<210> SEQ ID NO 233
<211> LENGTH: 14
<212> TYPE: PRT
<213> ORGANISM: Artificial Sequence
<220> FEATURE:
<223> OTHER INFORMATION: peptide linker

<400> SEQUENCE: 233

Glu Gly Lys Ser Ser Gly Ser Gly Ser Glu Ser Lys Val Asp
1               5                   10

<210> SEQ ID NO 234
<211> LENGTH: 18
<212> TYPE: PRT
<213> ORGANISM: Artificial Sequence
<220> FEATURE:
<223> OTHER INFORMATION: peptide linker

<400> SEQUENCE: 234

Lys Glu Ser Gly Ser Val Ser Ser Glu Gln Leu Ala Gln Phe Arg Ser
1               5                   10                  15

Leu Asp

<210> SEQ ID NO 235
<211> LENGTH: 5
<212> TYPE: PRT
<213> ORGANISM: Artificial Sequence
<220> FEATURE:
<223> OTHER INFORMATION: peptide linker

<400> SEQUENCE: 235

Gly Gly Gly Gly Ser
1               5
```

ANTI-RANKL ANTIBODIES AND METHODS OF USE

CROSS REFERENCE TO RELATED APPLICATIONS

This application is a U.S. national phase application of International Patent Application No. PCT/US2014/023623, filed on Mar. 11, 2014, which claims priority under 35 U.S.C. § 119(e) to U.S. Provisional Application No. 61/786,050 filed on Mar. 14, 2013, which applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is APEX_014_01WO_ST25.txt. The text file is 117 KB, was created on Mar. 11, 2014 and is being submitted electronically via EFS-Web.

BACKGROUND

Technical Field

The present invention relates generally to anti-RANKL antibodies, compositions and methods of using same. The invention is more specifically related to anti-RANKL antibodies and their manufacture and use. Such antibodies are useful, for example, in methods for treating any of a variety of bone resorption disease and oncological diseases such as bone metastasis.

Description of the Related Art

Morphogenesis and remodeling of bone are accomplished by the coordinated actions of bone-resorbing osteoclasts and bone-forming osteoblasts, which metabolize and remodel bone structure throughout development and adult life. Bone is constantly being resorbed and formed at specific sites in the skeleton called basic multicellular units. An estimated 10% of the total bone mass in the human body is remodeled each year. Upon activation, osteoclasts, which differentiate from hematopoietic monocyte/macrophage precursors, migrate to the basic multicellular unit, resorb a portion of bone and finally undergo apoptosis. Subsequently, newly generated osteoblasts, arising from preosteoblastic/stromal cells, form bone at the site of resorption. The development of osteoclasts is controlled by preosteoblastic cells, so that the processes of bone resorption and formation are tightly coordinated, thus allowing for a wave of bone formation to follow each cycle of bone resorption. Imbalances between osteoclast and osteoblast activities can result in skeletal abnormalities characterized by decreased (osteoporosis) or increased (osteopetrosis) bone mass (Khosla, Endocrinology, 2001, 142, 5050-5055; Nakashima et al., Curr. Opin. Rheumatol., 2003, 15, 280-287).

Communication between osteoblasts and osteoclasts occurs through cytokines and cell-to-cell contacts. A cytokine that performs a key regulatory role in bone remodeling is receptor activator of NF-kappaB ligand (RANKL). RANKL was first identified as a tumor necrosis factor (TNF) superfamily member [also known as tumor necrosis-factor-related activation-induced cytokine (TRANCE), osteoprotegerin ligand (OPGL), and osteoclast differentiation factor (ODF) and tumor necrosis factor (ligand) superfamily member 11 (TNFSF11)] and was subsequently identified as a factor that is capable of inducing osteoclast differentiation in vitro (Anderson et al., Nature, 1997, 390, 175-179; Lacey et al., Cell, 1998, 93, 165-176; Wong et al., J. Exp. Med., 1997, 186, 2075-2080; Yasuda et al., Proc. Natl. Acad. Sci. USA, 1998, 95, 3597-3602). The human RANKL gene maps to chromosome 13q14. The highest expression levels of RANKL are found in bone, bone marrow and lymphoid tissues (Anderson et al., Nature, 1997, 390, 175-179; Lacey et al., Cell, 1998, 93, 165-176; Wong et al., J. Exp. Med., 1997, 186, 2075-2080; Yasuda et al., Proc. Natl. Acad. Sci. USA, 1998, 95, 3597-3602) and it can also be detected in brain, heart, kidney, skeletal muscle and skin (Kartsogiannis et al., Bone, 1999, 25, 525-534).

RANKL is assembled from three RANKL subunits to form the functional trimeric molecule. RANKL is initially anchored to the cell membrane, and a small fraction of the protein released from the cell surface by the proteolytic action of the metalloprotease-disintegrin TNF-alpha convertase (TACE) (Lum et al., J. Biol. Chem., 1999, 274, 13613-13618). RANKL is both necessary and sufficient to stimulate of osteoclast differentiation and activity as well as to inhibit osteoclast apoptosis (Fuller et al., J. Exp. Med., 1998, 188, 997-1001; Lacey et al., Cell, 1998, 93, 165-176; Lum et al., J. Biol. Chem., 1999, 274, 13613-13618; Yasuda et al., Proc. Natl. Acad. Sci. USA, 1998, 95, 3597-3602). RANK is expressed on the surface of preosteoblastic and bone marrow stromal cells. Its expression can be positively or negatively modulated by various hormones, cytokines, growth factors and glucocorticoids, including, vitamin-D3, parathyroid hormone (PTH), interleukin 1-beta and TNF-alpha, all of which increase RANKL expression (Kong et al., Immunol. Today, 2000, 21, 495-502).

At the initiation of the cycle of bone resorption and formation, RANKL binds to its functional receptor RANK on preosteoclastic cells (Anderson et al., Nature, 1997, 390, 175-179; Lacey et al., Cell, 1998, 93, 165-176). This interaction between RANKL and RANK stimulates the formation of mature osteoclasts, which are phenotypically characterized by multinucleation, bone-resorbing function and expression of the lineage specific marker tartrate-resistant acid phosphatase (TRAP) (Burgess et al., J. Cell. Biol., 1999, 145, 527-538; Hsu et al., Proc. Natl. Acad. Sci. U.S.A., 1999, 96, 3540-3545; Lum et al., J. Biol. Chem., 1999, 274, 13613-13618; Yasuda et al., Proc. Natl. Acad. Sci. USA, 1998, 95, 3597-3602). Alternatively, RANKL can bind to the soluble receptor osteoprotegerin (OPG), which is expressed primarily by bone marrow stromal cells and serves to inhibit osteoclast maturation and activation by RANKL (Lacey et al., Cell, 1998, 93, 165-176; Yasuda et al., Proc. Natl. Acad. Sci. USA, 1998, 95, 3597-3602). PTH, a major regulator of bone remodeling, stimulates osteoclast function by simultaneously increasing RANKL expression while decreasing OPG expression (Lee and Lorenzo, Endocrinology, 1999, 140, 3552-3561). As preosteoblastic cells differentiate, RANKL mRNA levels are significantly reduced, whereas OPG mRNA levels increase (Gori et al., Endocrinology, 2000, 141, 4768-4776). Such a dynamic relationship between RANKL and OPG levels allows for a wave of osteoclast activity to be followed by a wave osteoblast activity, thereby completing the cycle of bone resorption and formation.

RANKL induces a transient elevation of calcium in osteoclasts due to release of calcium from intracellular stores (Komarova et al., J. Biol. Chem., 2003, 278, 8286-8293). In T-cells, T-cell receptor activation-induced calcium mobilization is solely responsible for the induction of RANKL expression (Wang et al., Eur. J. Immunol., 2002, 32, 1090-1098).

Mice homozygous for disruption of the RANKL gene are born at the expected frequency, but show severely retarded growth after weaning at three weeks of age. RANKL deficient mice exhibit severe osteopetrosis (thickening of bone), defects in tooth eruption and a complete lack of osteoclasts due to the inability of osteoblasts to support osteoclastogenesis (Kong et al., Immunol. Today, 2000, 21, 495-502).

RANKL function is not restricted to bone morphogenesis and remodeling. RANKL-deficient mice also display defects in early differentiation of T- and B-lymphocytes and lack all lymph nodes, demonstrating that RANKL is a regulator of lymph-node organogenesis and lymphocyte development, in addition to being an essential osteoclast differentiation factor (Kong et al., Immunol. Today, 2000, 21, 495-502). T-cell receptor stimulation induces RANKL gene expression, which subsequently leads to activation of c-Jun N-terminal kinase in T-cells (Wong et al., J. Biol. Chem., 1997, 272, 25190-25194). RANKL also participates in immune system function as an important survival factor for bone marrow derived dendritic cells by inhibiting apoptosis in these cells (Lum et al., J. Biol. Chem., 1999, 274, 13613-13618; Wong et al., J. Exp. Med., 1997, 186, 2075-2080). Additionally, RANKL is also required for the development of lobulo-alveolar mammary structures during pregnancy in mice (Fata et al., Cell, 2000, 103, 41-50).

Inappropriate activation of osteoclasts by RANKL can create an imbalance between the processes of bone resorption, resulting in the rate of bone resorption exceeding that of bone formation. Local or generalized bone loss is observed in many osteopenic disorders, including postmenopausal and age-related osteoporosis, periodontitis, familial expansile osteolysis and Paget's disease (Khosla, Endocrinology, 2001, 142, 5050-5055). Upregulation of RANKL mRNA has been reported in several of these diseases.

Paget's disease is characterized by large numbers of abnormal osteoclasts that induce increased bone resorption. RANKL mRNA expression is elevated in both cell lines and bone marrow derived from patients with Paget's disease. Furthermore, osteoclast precursors from Paget's disease patients undergo osteoclastogenesis at a much lower concentration of RANKL than normal cells (Menaa et al., J. Clin. Invest., 2000, 105, 1833-1838).

Other diseases with osteopenic pathologies, such as rheumatoid arthritis, chronic viral infection and adult and child leukemias, are characterized by activated T-cells and bone destruction (Kong et al., Immunol. Today, 2000, 21, 495-502). Rheumatoid arthritis is a chronic inflammatory disease characterized by progressive osteoclast-mediated bone resorption. Rheumatoid arthritis synovial fluid contains osteoclast precursors, RANKL-expressing T-cells and OPG-producing B-cells. Cultured macrophages from rheumatoid arthritis synovial fluid can differentiate into osteoclasts in a RANKL-dependent process (Itonaga et al., J. Pathol., 2000, 192, 97-104). In a T-cell dependent rat model of experimentally-induced arthritis that mimics many of the clinical features of human rheumatoid arthritis, inhibition of RANKL function through OPG treatment prevents bone destruction (Kong et al., Nature, 1999, 402, 304-309).

Multiple myeloma is a cancer in which osteoporosis and bone destruction are prominent features. Myeloma cell lines stimulate RANKL expression while inhibiting OPG expression by bone marrow stromal cells, resulting in a disruption of the balance between RANKL and OPG levels, followed by the aberrant production and activation of osteoclasts (Pearse et al., Proc. Natl. Acad. Sci. USA, 2001, 98, 11581-11586). A secreted form of RANKL is also expressed by cancer cells responsible for humoral hypercalcemia of malignancy (Nagai et al., Biochem. Biophys. Res. Commun., 2000, 269, 532-536). An increase in RANKL with a concurrent decrease in OPG expression is also observed following glucocorticoid treatment of osteoblastic lineage cells, which also stimulates osteoclastogenesis of these cells, suggesting a mechanism by which systemic glucocorticoid use leads to severe osteoporosis (Hofbauer et al., Endocrinology, 1999, 140, 4382-4389).

These findings demonstrate a link between immune function and bone physiology and also provide a molecular explanation for bone density loss associated with immune disorders and suggest that inhibition of RANKL function, and consequently osteoclast activity, can ameliorate osteopenic conditions (Kong et al., Immunol. Today, 2000, 21, 495-502).

As a consequence of RANKL involvement in many diseases, there remains a need for additional agents capable of effectively inhibiting RANKL function which is especially important in the treatment of disorders characterized by bone destruction, given that the upregulation of expression of RANKL is associated with so many different types of osteopenic diseases.

The present invention provides compositions and methods for inhibiting RANKL function.

BRIEF SUMMARY

One aspect of the present invention provides an isolated antibody, or an antigen-binding fragment thereof, that binds to RANKL, comprising (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising: the VLCDR1 region set forth in SEQ ID NO:6 or 15, the VLCDR2 region set forth in SEQ ID NO:7, and the VLCDR3 region set forth in SEQ ID NO: 8; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment of the isolated antibody, or antigen binding fragment thereof as described herein, the heavy chain variable region comprises the amino acid sequence set forth in SEQ ID NO:1. In another embodiment of the isolated antibody, or antigen binding fragment thereof as described herein, the light chain variable region comprises the amino acid sequence set forth in SEQ ID NO:2.

Another aspect of the present invention provides an isolated antibody, or an antigen-binding fragment thereof, that binds to RANKL, comprising a heavy chain variable region comprising the amino acid sequence set forth in SEQ ID NO:1. In one embodiment, the isolated antibody, or antigen-binding fragment thereof comprising a heavy chain variable region comprising the amino acid sequence set forth in SEQ ID NO:1, also comprises a light chain variable region which comprises an amino acid sequence having at least 90% identity to the amino acid sequence set forth in SEQ ID NO:2. In a further embodiment, the isolated antibody, or antigen-binding fragment thereof comprising a heavy chain variable region comprising the amino acid sequence set forth in SEQ ID NO:1, also comprises a light chain variable region which comprises the amino acid sequence set forth in SEQ ID NO:2.

Another aspect of the invention provides an isolated antibody, or an antigen-binding fragment thereof, that binds to human RANKL, comprising a light chain variable region comprising the amino acid sequence set forth in SEQ ID NO:2. In one embodiment, The isolated antibody, or antigen binding fragment thereof, comprising a light chain variable region comprising the amino acid sequence set forth in SEQ ID NO:2 also comprises a heavy chain variable region which comprises an amino acid sequence having at least 90% identity to the amino acid sequence set forth in SEQ ID NO:1.

In certain embodiments, the antibodies herein are humanized. Illustrative humanized antibodies may comprise the VH region comprising the amino acid sequence set forth in SEQ ID NO:9 and the VL region comprises the amino acid sequence set forth in SEQ ID NO:10 or 11. In certain other embodiments, the humanized antibodies may comprise the VH region comprising the amino acid sequence set forth in SEQ ID NO:226 and the VL region comprises the amino acid sequence set forth in SEQ ID NO:227. In other embodiments, the humanized antibodies may comprise the VH region comprising the amino acid sequence set forth in SEQ ID NO:229 and the VL region comprises the amino acid sequence set forth in SEQ ID NO:230. In yet other embodiments, the humanized antibodies may comprise the VH region comprising the amino acid sequence set forth in SEQ ID NO:231 and the VL region comprises the amino acid sequence set forth in SEQ ID NO:232.

In certain embodiments, the antibodies herein may be selected from the group consisting of a single chain antibody, a ScFv, a univalent antibody lacking a hinge region, and a minibody. In one embodiment, the antibody is a Fab or a Fab' fragment. In another embodiment, the antibody is a $F(ab')_2$ fragment or a whole antibody. In certain other embodiments, the antibodies described herein comprising a human IgG constant domain. In one embodiment, the IgG constant domain comprises an IgG2 CH1 domain. In other embodiments the IgG constant domain comprises an IgG2 Fc region.

Another aspect of the present invention provides antibodies which compete with any of the antibodies described herein for binding to RANKL, in particular human RANKL.

Another aspect of the present invention provides for an isolated antibody, or antigen-binding fragment thereof, that binds RANKL with a KD of about 0.16 nM or lower. In certain embodiments, the antibodies described herein bind to RANKL with a KD of between about 0.016 nM and 0.36 nM. In certain embodiments, the antibodies described herein bind to RANKL with a KD of between about 0.026 nM and 0.26 nM. In certain embodiments, the antibodies described herein bind to RANKL with a KD of between about 0.036 nM and 0.36 nM. In certain embodiments, the antibodies described herein bind to RANKL with a KD of about 0.05 nM, 0.06 nM, 0.07 nM, 0.08 nM, 0.09 nM, 0.1 nM, 0.15 nM, 0.16 nM, 0.17 nM, 0.18 nM, 0.19 nM, 0.2 nM, 0.25 nM, 0.3 nM, 0.35 nM, or 0.4 nM.

Another aspect of the present invention provides an isolated antibody, or antigen-binding fragment thereof, wherein the isolated antibody, or antigen-binding fragment thereof: (a) blocks binding of RANKL to RANK; (b) inhibits RANKL-induced osteoclast differentiation; (c) inhibits osteoclast cell activity; (d) inhibits bone loss and increase bone density; (e) Binds and inhibits both human and rodent RANKL; or (f) a combination of any one or more of a. -e.

Another aspect of the present invention also provides isolated polynucleotides encoding the isolated antibodies, or antigen-binding fragment thereof, as described herein. The present invention also provides expression vectors comprising the polynucleotide encoding the isolated antibodies, and isolated host cells comprising the vectors.

Another aspect of the present invention provides a composition comprising a physiologically acceptable carrier and a therapeutically effective amount of an isolated antibody or antigen-binding fragment thereof as described herein.

Yet another aspect of the present invention provides a method for treating a patient having an osteopenic disorder, comprising administering to the patient a composition comprising a physiologically acceptable carrier and a therapeutically effective amount of an isolated antibody or antigen-binding fragment thereof as described herein, thereby treating the osteopenic disorder. In this regard, the osteopenic disorder is selected from the group consisting of osteoporosis, periodontitis, cancer associated bone metastasis, multiple myeloma, rheumatoid arthritis, psoriatic arthritis, familial expansile osteolysis, Paget's disease, juvenile Paget's disease, osteoclastoma, bone loss associated with chronic viral infection and adult and child leukemias, and periprosthetic bone loss.

Another aspect of the present invention provides an isolated antibody, or an antigen-binding fragment thereof, that binds to RANKL, comprising (i) a heavy chain variable region comprising the VHCDR1, VHCDR2, and VHCDR3 of any one of the VH regions shown in FIG. 1; and (ii) a light chain variable region comprising the VLCDR1, the VLCDR2, and the VLCDR3 region of the corresponding VL region of any one of the antibodies shown in FIG. 1; or a variant of said antibody, or an antigen-binding fragment thereof, comprising heavy and light chain variable regions identical to the heavy and light chain variable regions of (i) and (ii) except for up to 8 amino acid substitutions in said CDR regions.

Yet another aspect of the present invention provides an isolated antibody, or an antigen-binding fragment thereof, that binds to RANKL, comprising a heavy chain variable region comprising any one of the VH regions shown in FIG. 1. In this regard, such an antibody may further comprising a light chain variable region comprising an amino acid sequence having at least 90% identity to the corresponding VL region as shown in FIG. 1. In another embodiment such an antibody may further comprise the corresponding light chain variable region as shown in FIG. 1.

Yet a further aspect of the present invention provides an isolated antibody, or an antigen-binding fragment thereof, that binds to RANKL, comprising a light chain variable region comprising any one of the VL regions shown in FIG. 1. In this regard, such antibodies may further comprise a heavy chain variable region comprising an amino acid sequence having at least 90% identity to the corresponding VH region as shown in FIG. 1 or may further comprise the corresponding heavy chain variable region as shown in FIG. 1.

BRIEF DESCRIPTION OF THE SEVERAL VIEWS OF THE DRAWINGS

FIG. 1A and FIG. 1B show amino acid sequence alignments of 40 anti-RANKL rabbit antibody heavy chain variable regions (VH) and a light chain variable region (VL), respectively. FIG. 1C shows the amino acid sequence alignment of clone 23 rabbit parental clone and humanized clone 23 VH and VL. The SEQ ID NOs for the VH and VL sequences shown in FIG. 1 are set forth in SEQ ID NOs:1, 2, 9-11 and 16-93. The underlined CDR sequences are set forth in SEQ ID NOs:3-8, 13-15 and 94-225. FIG. 1D shows the amino acid sequence alignment of clone 408 rabbit parental clone and humanized clone 408 VH and VL. FIG. 1E shows the amino acid sequence alignment of clone EBI51-22 rabbit parental clone and humanized clone EBI-51-22 VH and VL.

FIG. 2A-FIG. 2D are graphs showing the binding of 40 anti-RANKL antibodies to RANKL-transfected 293 cells.

FIG. 3A-FIG. 3G show the ability of anti-RANKL antibodies to block the binding of RANKL to its cognate receptor (RANK).

FIG. 4A-FIG. 4D are bar graph showing the cross-reactivity of anti-RANKL antibody with human RANKL and mouse RANKL.

FIG. 5 is a graph showing inhibition by anti-RANKL antibodies of osteoclast cell differentiation induced by RANKL.

FIG. 6A and FIG. 6B are graphs showing binding of humanized anti-RANKL antibody 23 and 408 to RANKL expressed on the surface of 293 cells as compared to their parental rabbit antibodies. The clone 23 humanized heavy and light chains used were VH 23HZD-1 HC (VH sequence is provided in SEQ ID NO: 9) with either the humanized VL provided in SEQ ID NO:10 (23 Vk) or 11 (23 Vkb) as noted.

FIG. 7A-FIG. 7C shows that humanized antibodies 23, 408 and EBI-51-22 demonstrated comparable blocking activity of RANKL binding to RANK as compared to their parental rabbit clones. The clone 23 humanized heavy and light chains used were VH 23HZD-1 HC (VH sequence is provided in SEQ ID NO: 9) with either the humanized VL provided in SEQ ID NO:10 (23 Vk) or 11 (23 Vkb) as noted.

FIG. 8A and FIG. 8B show the ability of humanized anti-RANKL antibodies 23, 408 and EBI-51-22 to inhibit osteoclast differentiation induced by human RANKL. The clone 23 humanized heavy and light chains used were VH 23HZD-1 HC (VH sequence is provided in SEQ ID NO: 9) with either the humanized VL provided in SEQ ID NO:10 (23 Vk) or 11 (23 Vkb) as noted.

FIG. 9A and FIG. 9B shows the ability of humanized anti-RANKL antibodies 23, 408 and EBI-51-22 to inhibit osteoclast differentiation induced by mouse RANKL. The clone 23 humanized heavy and light chains used were VH 23HZD-1 HC (VH sequence is provided in SEQ ID NO: 9) with either the humanized VL provided in SEQ ID NO:10 (23 Vk) or 11 (23 Vkb) as noted.

FIG. 10 shows that rabbit anti-RANKL antibody 23 significantly inhibited osteoclast activity in vivo.

FIG. 11 is a bar graph demonstrating that anti-RANKL antibody 23 significantly increased bone density in OVX mice. The clone 23 humanized heavy and light chain used were VH 23HZD-1 HC (VH sequence is provided in SEQ ID NO: 9) with the humanized VL provided in SEQ ID NO: 11 (23 Vkb).

FIG. 12 is a graph comparing h23n IgG2 humanized clone 23 antibody to the clone 23 humanized VH 23HZD-1 HC/humanized Vkb light chain with IgG1 or IgG2 as noted.

BRIEF DESCRIPTION OF THE SEQUENCES

SEQ ID NO:1 is the amino acid sequence of the VH region of the clone 23 rabbit anti-RANKL antibody.

SEQ ID NO:2 is the amino acid sequence of the VL region of the clone 23 rabbit anti-RANKL antibody.

SEQ ID NO:3 is the amino acid sequence of the VHCDR1 region of the clone 23 rabbit anti-RANKL antibody.

SEQ ID NO:4 is the amino acid sequence of the VHCDR2 region of the clone 23 rabbit anti-RANKL antibody.

SEQ ID NO:5 is the amino acid sequence of the VHCDR3 region of the clone 23 rabbit anti-RANKL antibody.

SEQ ID NO:6 is the amino acid sequence of the VLCDR1 region of the clone 23 rabbit anti-RANKL antibody.

SEQ ID NO:7 is the amino acid sequence of the VLCDR2 region of the clone 23 rabbit anti-RANKL antibody.

SEQ ID NO:8 is the amino acid sequence of the VLCDR3 region of the clone 23 rabbit anti-RANKL antibody.

SEQ ID NO:9 is the amino acid sequence of a humanized sequence of the VH region of the clone 23 rabbit anti-RANKL antibody (23HZD-1 HC).

SEQ ID NO:10 is the amino acid sequence of a humanized sequence of the VL region of the clone 23 rabbit anti-RANKL antibody. Also referred to herein as 23LHZD or Vk.

SEQ ID NO:11 is the amino acid sequence of a second humanized sequence of the VL region of the clone 23 rabbit anti-RANKL antibody. Also referred to herein as 23LHZD_b or Vkb).

SEQ ID NO:12 is the amino acid sequence of a second humanized sequence of the VH region of the clone 23 rabbit anti-RANKL antibody (23HZD-2 HC).

SEQ ID NO:13 is the amino acid sequence of the VHCDR1 of the 23HZD-2 humanized clone 23 rabbit anti-RANKL antibody.

SEQ ID NO:14 is the amino acid sequence of the VHCDR2 of the 23HZD-2 humanized clone 23 rabbit anti-RANKL antibody.

SEQ ID NO:15 is the amino acid sequence of the VLCDR1 of the second humanized VL sequence of the clone 23 rabbit anti-RANKL antibody (VLbCDR1).

| VH amino acid sequences | |
|---|---|
| Clone Number | SEQ ID NO: |
| 7 | 16 |
| 20 | 17 |
| 37 | 18 |
| 68 | 19 |
| 91 | 20 |
| 130 | 21 |
| 147 | 22 |
| 174 | 23 |
| 191 | 24 |
| 193 | 25 |
| 210 | 26 |
| 220 | 27 |
| 227 | 28 |
| 238 | 29 |
| 246 | 30 |
| 256 | 31 |
| 270 | 32 |
| 299 | 33 |
| 318 | 34 |
| 327 | 35 |
| 379 | 36 |
| 383 | 37 |
| 388 | 38 |
| 408 | 39 |
| 411 | 40 |
| 415 | 41 |
| 416 | 42 |
| 420 | 43 |
| 447 | 44 |
| 476 | 45 |
| 480 | 46 |
| 547 | 47 |
| 565 | 48 |
| EBI-51-1 | 49 |
| EBI-51-2 | 50 |
| EBI-51-4 | 51 |
| EBI-51-11 | 52 |

| EBI-51-22 | 53 |
| EBI-51-23 | 54 |

| VL amino acid sequences ||
| Clone No. | SEQ ID NO: |
| --- | --- |
| 7 | 55 |
| 20 | 56 |
| 37 | 57 |
| 68 | 58 |
| 91 | 59 |
| 130 | 60 |
| 147 | 61 |
| 174 | 62 |
| 191 | 63 |
| 193 | 64 |
| 210 | 65 |
| 220 | 66 |
| 227 | 67 |
| 238 | 68 |
| 246 | 69 |
| 256 | 70 |
| 270 | 71 |
| 299 | 72 |
| 318 | 73 |
| 327 | 74 |
| 379 | 75 |
| 383 | 76 |
| 388 | 77 |
| 408 | 78 |
| 411 | 79 |
| 415 | 80 |
| 416 | 81 |
| 420 | 82 |
| 447 | 83 |
| 476 | 84 |
| 480 | 85 |
| 547 | 86 |
| 565 | 87 |
| EBI-51-1 | 88 |
| EBI-51-2 | 89 |
| EBI-51-4 | 90 |
| EBI-51-11 | 91 |
| EBI-51-22 | 92 |
| EBI-51-23 | 93 |

| VHCDR1 amino acid sequences ||
| Clone No(s). | SEQ ID NO: |
| --- | --- |
| 246 | 94 |
| EBI-51-23 | 95 |
| 220, 256, 327 | 96 |
| 37 | 97 |
| 379 | 98 |
| 193 | 99 |
| 210 | 100 |
| 91, 227, 480 | 101 |
| 415 | 102 |
| 174 | 103 |
| 416 | 104 |
| 476 | 105 |
| 383 | 106 |
| 565 | 107 |
| EBI-51-4 | 108 |
| 270 | 109 |
| 130, 388, 411 | 110 |
| 420, 447 | 111 |
| 20, 68, 318, 547 | 112 |
| 299 | 113 |
| EBI-51-2 | 114 |
| EBI-51-22 | 115 |
| 147, 408, EBI-51-11 | 116 |
| 238 | 117 |
| 7 | 118 |
| 191 | 119 |
| EBI-51-1 | 120 |

| VHCDR2 amino acid sequences ||
| Clone No. | SEQ ID NO: |
| --- | --- |
| 383 | 121 |
| 476 | 122 |
| EBI-51-1 | 123 |
| 130 | 124 |
| 388, 411 | 125 |
| EBI-51-4 | 126 |
| 91, 220, 227, 256, 327, 415, 480 | 127 |
| EBI-51-23 | 128 |
| 191 | 129 |
| 299 | 130 |
| 270 | 131 |
| 37 | 132 |
| 68 | 133 |
| 420, 447 | 134 |
| 210 | 135 |
| 7, 174, 238, 379 | 136 |
| 20 | 137 |
| 416, 565 | 138 |
| 246, 318, 547 | 139 |
| 408 | 140 |
| 147 | 141 |
| 193 | 142 |
| EBI-51-11 | 143 |
| EBI-51-2 | 144 |
| EBI-51-22 | 145 |

| VHCDR3 amino acid sequences ||
| Clone No. | SEQ ID NO: |
| --- | --- |
| 193 | 146 |
| 37, 270 | 147 |
| EBI-51-2; EBI-51-4; EBI-51-11; EBI-51-22 | 148 |
| 191 | 149 |
| 130, 147, 388, 408, 411 | 150 |
| EBI-51-23 | 151 |
| 318 | 152 |
| 379 | 153 |
| 68 | 154 |
| 20 | 155 |
| 7, 565 | 156 |
| 238, 246 | 157 |
| 416 | 158 |
| 210 | 159 |
| 174, 420, 447, 547 | 160 |
| EBI-51-1 | 161 |
| 91, 227 | 162 |
| 220, 256, 327, 415 | 163 |
| 299 | 164 |
| 476 | 165 |
| 383 | 166 |
| 480 | 167 |

| VLCDR1 amino acid sequences ||
| Clone No. | SEQ ID NO: |
| --- | --- |
| 20 | 168 |
| 476 | 169 |
| EBI-51-2 | 170 |
| 7 91; 130; 147; 174; 220; 227; 238; 256; 327; 388; 408; 411; 415; 416; 420; 447; 480; 565; EBI-51-1; EBI-51-4; EBI-51-11; EBI-51-22; EBI-51-23; | 171 |
| 270 | 172 |
| 383 | 173 |
| 37, 191, 210, 246, 379, 547 | 174 |
| 68, 193, 318 | 175 |
| 299 | 176 |

-continued

VLCDR2 amino acid sequences

| Clone No. | SEQ ID NO: |
|---|---|
| 476 | 177 |
| 7, 210, 270, 318, 420, 447, 547 | 178 |
| 174, 238 | 179 |
| 130, 147, 388, 408, 411, 565, EBI-51-23 | 180 |
| 379 | 181 |
| 20 | 182 |
| 299, EBI-51-1, EBI-51-2, EBI-51-4, EBI-51-11, EBI-51-22 | 183 |
| 37, 191 | 184 |
| 383 | 185 |
| 193 | 186 |
| 68, 220, 246, 256, 327, 415, 416, 480 | 187 |
| 91, 227 | 188 |

VLCDR3 amino acid sequences

| Clone No. | SEQ ID NO: |
|---|---|
| 7 | 189 |
| 20 | 190 |
| 37 | 191 |
| 68 | 192 |
| 91 | 193 |
| 130 | 194 |
| 147 | 195 |
| 174 | 196 |
| 191 | 197 |
| 193 | 198 |
| 210 | 199 |
| 220 | 200 |
| 227 | 201 |
| 238 | 202 |
| 246 | 203 |
| 256 | 204 |
| 270 | 205 |
| 299 | 206 |
| 318 | 207 |
| 327 | 208 |
| 379 | 209 |
| 383 | 210 |
| 388, 411 | 211 |
| 408 | 212 |
| 415 | 213 |
| 416 | 214 |
| 420, 447 | 215 |
| 476 | 216 |
| 480 | 217 |
| 547 | 218 |
| 565 | 219 |
| EBI-51-1 | 220 |
| EBI-51-2 | 221 |
| EBI-51-4 | 222 |
| EBI-51-11 | 223 |
| EBI-51-22 | 224 |
| EBI-51-23 | 225 |

SEQ ID NO:226 is the amino acid sequence of a third humanized sequence of the VH region of the clone 23 rabbit anti-RANKL antibody (h23n VH).

SEQ ID NO:227 is the amino acid sequence of a third humanized sequence of the VL region of the clone 23 rabbit anti-RANKL antibody (h23n VL).

SEQ ID N0:228 is the amino acid sequence of the h23n VHCDR3.

SEQ ID NO:229 is the amino acid sequence of a humanized VH region of the clone 408 rabbit anti-RANKL antibody.

SEQ ID NO:230: is the amino acid sequence of a humanized VL region of the clone 408 rabbit anti-RANKL antibody.

SEQ ID N0:231: is the amino acid sequence of a humanized VH region of the clone EBI51-22 rabbit anti-RANKL antibody.

SEQ ID NO:232: is the amino acid sequence of a humanized VL for clone EBI51-22 rabbit anti-RANKL antibody.

DETAILED DESCRIPTION

The present disclosure relates to antibodies and antigen-binding fragments thereof that specifically bind to RANKL, in particular antibodies having specific epitopic specificity and functional properties. One embodiment of the invention encompasses specific humanized antibodies and fragments thereof capable of binding to RANKL, blocking RANKL binding with RANK and inhibiting RANK induced downstream cell signaling and biological effects. In more specific embodiments of the invention, the antibodies described herein specifically bind to RANKL with affinity of about 0.16 nM and block RANKL binding to RANK. In further embodiments, the antibodies described herein specifically bind to RANKL with an affinity of about 0.05 nM to about 0.25 nM and block RANKL binding to RANK. In another embodiment, the antibodies described herein specifically bind to RANKL with an affinity of about 0.08, 0.09, 0.095, 0.11, 0.12, 0.13, 0.14, 0.15, 0.16, 0.17, 0.18, 0.19, or about 0.2 nM to about 0.25 nM. In a further embodiment, the antibodies described herein specifically bind to RANKL with an affinity of about 0.16 nM or lower and block RANKL binding to RANK.

Embodiments of the invention pertain to the use of anti-RANKL antibodies or antigen-binding fragments thereof for the diagnosis, assessment and treatment of diseases and disorders associated with RANK or aberrant expression thereof. The subject antibodies are used in the treatment or prevention of osteopenic disorders, including osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss, among other diseases.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to the RANKL. In particular, the antibodies described herein specifically bind to RANKL with unexpectedly high affinity, block RANK binding to RANKL, block RANK activity and have therapeutic utility for the treatment of diseases associated with aberrant expression of RANK. The antibodies described herein also have advantageous properties such as the ability to inhibit a variety of RANKL-mediated biological effects (e.g., osteoclast cell differentiation and/or activity; loss/decrease of bone density). The antibodies described herein may also have effects on RANKL receptor internalization.

Sequences of illustrative antibodies, or antigen-binding fragments, or VH, VL, or complementarity determining regions (CDRs) thereof, including humanized versions, are set forth in SEQ ID NOs:1-232.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to the RANKL. In this regard, an antigen-binding fragment of the herein described antibodies may comprise 1, 2, 3, 4, 5, or all 6 CDRs of a VH and VL sequence set forth herein from antibodies that bind RANKL. An antigen-binding fragment of the RANKL-specific antibodies described herein is capable of binding to RANKL. In certain embodiments, an antigen-binding fragment or an antibody comprising an antigen-binding fragment, prevents or inhibits RANK binding to the RANKL and subsequent signaling events. In certain embodiments, the antigen-binding fragment binds specifically to and/or inhibits or modulates the biological activity of human RANKL.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (III et al., *Prot. Eng.* 10: 949-57 (1997); minibodies (Martin et al., *EMBO J* 13: 5305-9 (1994); diabodies (Holliger et al., *PNAS* 90: 6444-8 (1993); or Janusins (Traunecker et al., *EMBO J* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to RANKL through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an RANKL binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.,* 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a nanobody. Nanobodies® are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces*, *Kluyvermyces, Hansenula* or *Pichia* (see e.g. U.S. Pat. No. 6,838,254). The production process is scalable and multi-kilogram quantities of nanobodies have been produced. Nanobodies® may be formulated as a ready-to-use solution having a long shelf life. The Nanoclone® method (see, e.g., WO 06/079372) is a proprietary method for generating Nanobodies® against a desired target, based on automated high-throughput selection of B-cells.

In certain embodiments, the anti-RANKL antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of the anti-RANKL antibodies disclosed herein include the methods described in U.S. Pat. No. 7,462,697. Illustrative humanized antibodies according to certain embodiments of the present invention comprise the humanized sequences provided in SEQ ID NOs:9, 10, 19, 20 and 226-232.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-RANKL antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-RANKL antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, an RANKL-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al. (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds RANKL. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for RANKL. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to RANKL. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for RANKL antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for RANKL and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a RANKL epitope is an antibody that binds one RANKL epitope with greater affinity, avidity, more readily, and/or with greater duration than it binds to other RANKL epitopes or non-RANKL epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the anti-RANKL antibodies described herein have an affinity of about 100, 150, 155, 160, 170, 175, 180, 185, 190, 191, 192, 193, 194, 195, 196, 197, 198 or 199 picomolar, and in some embodiments, the antibodies may have even higher affinity for RANKL.

The term "immunologically active", with reference to an epitope being or "remaining immunologically active", refers to the ability of an antibody (e.g., anti-RANKL antibody) to bind to the epitope under different conditions, for example, after the epitope has been subjected to reducing and denaturing conditions.

An antibody or antigen-binding fragment thereof according to certain preferred embodiments of the present application may be one that competes for binding to RANKL with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to RANKL.

In this regard, as used herein, the terms "competes with", "inhibits binding" and "blocks binding" (e.g., referring to inhibition/blocking of binding of RANKL to RANK or referring to inhibition/blocking of binding of an anti-RANKL antibody to RANKL) are used interchangeably and encompass both partial and complete inhibition/blocking. The inhibition/blocking of RANKL binding to RANK preferably reduces or alters the normal level or type of cell signaling that occurs when RANKL binds to RANK without inhibition or blocking. Inhibition and blocking are also intended to include any measurable decrease in the binding of RANKL to RANK when in contact with an anti-RANKL antibody as disclosed herein as compared to RANKL not in contact with an anti-RANKL antibody, e.g., the blocking of RANKL binding to RANK by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 1IIS and 1 IIX)(Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ M$^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders, that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of an RANKL-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-RANKL antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

In another contemplated embodiment, a RANKL-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros E V., et al., 2010 Mol Cancer Ther; 9(11); 3033-40; Polito L., et al. 2009 British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In one embodiment, an antibody or antigen-binding fragment thereof of the disclosure is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. Nos. 5,714,586; 5,712,374; 5,264,586; 5,773,001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between an RANKL-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}Y$, $^{123}I$, $^{125}I$, $^{131}I$, $^{186}Re$, $^{188}Re$, $^{211}At$, and $^{212}Bi$.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and antimitotic agents (e.g., vincristine and vinblastine).

Moreover, a RANKL-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

The desired functional properties of anti-RANKL antibodies may be assessed using a variety of methods known to the skilled person affinity/binding assays (for example, surface plasmon resonance, competitive inhibition assays); cytotoxicity assays, cell viability assays, cell proliferation or differentiation assays in response to RANKL (e.g., Raw cell assays or other osteoclast cell differentiation assay), bone density assays, measurement of inhibition of bone loss, tartrate-resistant acid phosphatase (TRAP) activity assays, and the like, using in vitro or in vivo models. Other assays may test the ability of antibodies described herein to block normal RANK/RANKL-mediated responses, such as osteoclast cell differentiation and/or activity or may test the in vivo inhibition of loss of bone density. The antibodies described herein may also be tested for effects on RANKL receptor internalization, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind RANKL as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include hnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-RANKL antibodies described herein. In certain embodiments, polynucleotides are provided that comprise some or all of a polynucleotide sequence encoding an antibody as described herein and complements of such polynucleotides.

In other related embodiments, polynucleotide variants may have substantial identity to a polynucleotide sequence encoding an anti-RANKL antibody described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind RANKL, or antigen-binding fragments thereof. In other embodiments, such polynucleotides encode antibodies or antigen-binding fragments, or CDRs thereof, that bind to RANKL at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to RANKL with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant RANKL-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the MegAlign™ program in the Lasergene® suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encodes antibodies that bind to RANKL. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefore. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an RANKL-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to RANKL of the present disclosure, or sequences that have deletions from, additions to, and/or substitutions of one or more amino acid of an anti-RANKL antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-RANKL antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. Any polypeptide amino acid sequences provided herein that include a signal peptide are also contemplated for any use described herein without such a signal or leader peptide. As would be recognized by the skilled person, the signal peptide is usually cleaved during processing and is not included in the active antibody protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art. Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., Gene 40:39 46 (1985); Murphy et al., Proc. Natl. Acad. Sci. USA 83:8258 8262 (1986); U.S. Pat. Nos. 4,935,233 and 4,751,180.

Other illustrative spacers may include, for example, Glu-Gly-Lys-Ser-Ser-Gly-Ser-Gly-Ser-Glu-Ser-Lys-Val-Asp (Chaudhary et al., 1990, Proc. Natl. Acad. Sci. U.S.A. 87:1066-1070) (SEQ ID NO:233) and Lys-Glu-Ser-Gly-Ser-Val-Ser-Ser-Glu-Gln-Leu-Ala-Gln-Phe-Arg-Ser-Leu-Asp (Bird et al., 1988, Science 242:423-426) (SEQ ID NO:234).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO:235) repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to RANKL). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to RANKL at least about 50%, at least about 70%, and in certain embodiments, at least about 90% as well as an antibody sequence specifically set forth herein. In further embodiments, such variant antibodies or antigen-binding fragments, or CDRs thereof, bind to RANKL with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable region having an amino acid sequence that is at least 80% identical, at least 85%, at least 90%, 91%, 92%, 93%, 94%, 95%, 96%, 97%, 98%, or at least 99% identical, to the heavy chain variable region of an anti-RANKL antibody described herein; or b) a light chain variable region having an amino acid sequence that is at least 80% identical, at least 85%, at least 90%, 91%, 92%, 93%, 94%, 95%, 96%, 97%, 98%, or at least 99% identical, to the light chain variable region of an anti-RANKL antibody described herein; or both a) and b). The amino acid sequence of illustrative heavy and light chain regions are set forth in SEQ ID NOs:1, 2, 9-12 and 16-93.

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., RANKL). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167). The amino acid sequences of the VH and VL CDRs of the anti-RANKL antibodies described herein (and shown in FIG. 1A-FIG. 1D) are provided in SEQ ID NOs: 3-8, 13-15, 94-225 and 228.

Determination of the three-dimensional structures of representative polypeptides (e.g., variant RANKL-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. Science 327:1014-1018 (2010). Some additional non-limiting examples of computer algorithms that may be used for these and related embodiments, such as for rational design of RANKL-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

In another embodiment of invention, the anti-RANKL antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see, e.g., U.S. Pat. No. 7,462, 697). Thus, illustrative methods for making the anti-RANKL antibodies of the present disclosure include the RabMab® rabbit monoclonal antibody technology described, for example, in U.S. Pat. Nos. 5,675,063 and 7,429,487. In this regard, in certain embodiments, the anti-RANKL antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions and Methods of Use

The present disclosure provides compositions comprising the RANKL-specific antibodies, antigen-binding fragments thereof and administration of such composition in a variety of therapeutic settings.

Administration of the RANKL-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in symptoms associated with osteopenic disorders, including osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss. Such clinically relevant symptoms are known to the skilled clinician and include but are not limited to bone loss, back pain, swollen gums, red or purplish gums, tender gums, pus between the teeth, bad breath, tender, warm, swollen joints, morning stiffness that may last for hours; firm bumps of tissue under the skin on arms (rheumatoid nodules); fatigue, fever and weight loss. As would be understood by the skilled clinician signs and symptoms may vary in severity and from patient to patient.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The RANKL-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described RANKL-specific antibody in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, an injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an RANKL-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an RANKL-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., RANKL-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the RANKL-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-RANKL antibody compositions of this disclosure in combination with one or more other therapeutic agents. Such therapeutic agents may be accepted in the art as a standard treatment for a particular disease state as described herein, such as rheumatoid arthritis, inflammation or cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the anti-RANKL antibodies disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-RANKL antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the antibodies described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

The compositions comprising herein described RANKL-specific antibodies may be administered to an individual afflicted with a disease as described herein, including, but not limited to osteopenic disorders, including osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss. For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising RANKL-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Provided herein are methods of treatment using the antibodies that bind RANKL. In one embodiment, an antibody of the present invention is administered to a patient having a disease involving inappropriate expression of RANKL, which is meant in the context of the present disclosure to include diseases and disorders characterized by aberrant RANKL expression or activity, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of RANKL relative to that which is normally detectable. Such an overabundance of RANKL can be measured relative to normal expression, appearance, or activity of RANKL signaling events, and said measurement may play an important role in the development and/or clinical testing of the antibodies described herein.

In particular, the present antibodies are useful for the treatment of a variety of osteopenic disorders associated with the expression of RANKL. For example, one embodiment of the invention provides a method for the treatment of a disorder including, but not limited to, osteopenic disorders, including osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss, by administering to a cancer patient a therapeutically effective amount of a herein disclosed RANKL-specific antibody. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for preventing progression of an osteopenic disorder including, but not limited to osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss, by administering to a patient in need thereof a therapeutically effective amount of a herein disclosed RANKL-specific antibody (e.g., an amount that, following administration, inhibits, prevents or delays metastasis of a cancer in a statistically significant manner, i.e., relative to an appropriate control as will be known to those skilled in the art).

Another embodiment provides a method for preventing an osteopenic disorder including, but not limited to, osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss, by administering to a patient having one or more of these disorders a therapeutically effective amount of a herein disclosed RANKL-specific antibody.

Another embodiment provides a method for treating, inhibiting the progression of or prevention of osteopenic disorders, including osteoporosis, periodontitis, cancer associated bone metastasis, multiple myeloma, rheumatoid arthritis, psoriatic arthritis, familial expansile osteolysis, Paget's disease (including juvenile Paget's disease) osteoclastoma, bone loss associated with chronic viral infection and adult and child leukemias, and periprosthetic bone loss, by administering to a patient afflicted by one or more of these diseases a therapeutically effective amount of a herein disclosed RANKL-specific antibody.

In another embodiment, anti-RANKL antibodies of the present invention are used to determine the structure of bound antigen, e.g., conformational epitopes, which structure may then be used to develop compounds having or mimicking this structure, e.g., through chemical modeling and SAR methods.

Various other embodiments of the present invention relate, in part, to diagnostic applications for detecting the presence of cells or tissues expressing RANKL. Thus, the present disclosure provides methods of detecting RANKL in a sample, such as detection of cells or tissues expressing RANKL. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies described herein are conjugated to a detectable label that may be detected directly or indirectly. In this regard, an antibody "conjugate" refers to an anti-RANKL antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting RANKL or cells or tissues expressing RANKL in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Production and Humanization of Anti-RANKL Antibodies

Four New Zealand white rabbits were immunized subcutaneously with recombinant human RabFc-RANKL in complete Freund's adjuvant. The rabbit with the highest serum titers and RANKL neutralizing activity was intravenously boosted with RabFC-RANKL in PBS four days before splenectomy for cell fusion.

Antibody Generation

Splenocytes were harvested from the immunized rabbit and fused with rabbit plasmacytoma cells 240E-W2 using PEG4000 (Sigma Chemical, St. Louis, Mo.). After being selected by HAT (hypoxanthine, aminopterin, and thymidine), hybridoma clones growing in the original 96-well plates were transferred to new 96-well plates with a medium change. Hybridoma supernatants were collected and screened for specific binding to RANKL in a direct ELISA. 120 hybridomas that were positive in the ELISA binding assay were selected for functional screening.

Functional Screening of Hybridomas

For initial functional screening, the supernatant from the confirmed 120 positive clones were tested for RANKL binding by FACS and for neutralizing RANKL/RANK binding by ELISA. These experiments identified 56 unique positive clones which were further tested for functional activity in a RAW cell assay. The RAW cell assay measures inhibition of RAW cell osteoclast differentiation induced by RANKL. 56 clones were found to neutralize RANKL activity. The top 40 clones that neutralized RANKL activity were further selected for molecular cloning and recombinant expression for further functional characterization. FIG. 1A and FIG. 1B shows an alignment of the amino acid sequences of the VH and VL, respectively, of the top 40 clones.

Recombinant Anti-RANKL Antibodies

DNA fragments of L chains and the variable region (VH) of H chains of rabbit IgG from the top 40 clones were amplified by PCR. The L chain fragment was cloned into pTT5 vector at Hind III and Not I sites and the VH fragment into the constant region of H chain built-in pTT5 vector at Hind III and Kpn I sites. For each hybridoma, three DNA clones of L or H chain were sequenced and the plasmid with a consensus sequence was identified and used for recombinant expression. To express the recombinant antibody, the L and H chain plasmids were co-transfected into 293-6E cells (National Research Council Canada). The supernatants were harvested 5 days later and quantified using an ELISA assay to measure the IgG concentration before functional assays.

Functional Screening of Recombinant Anti-RANKL Antibodies

Numerous assays were used to characterize the potency of the selected anti-RANKL antibodies identified above. As shown in FIG. 2, the selected anti-RANKL antibodies were tested for binding to RANKL on the cell surface using flow cytometry. All forty anti-RANKL antibodies specifically bind to RANKL expressed on the surface of 293 cells, with clone 23, 408 and EBI-51-22 showing the best binding of the 40 clones. Additionally, as shown in FIG. 3, the selected anti-RANKL antibodies were tested for blocking of RANKL binding to its receptor. In particular, human RANK purchased from R&D (8 ug/ml) was coated onto 96-well plates 16 hours before the experiment. The plates were subsequently treated with 0.5 ug/ml RANKL pre-incubated with various concentrations of recombinant anti-RANKL antibody for 30 min at 37° C. A mouse anti-human RANKL antibody was used to detect RANKL bound to coated RANK and a secondary goat anti-mouse HRP was used to detect the signal. All 40 anti-RANKL antibodies specifically block binding of RANKL to RANK, with clones 23, 408 and EBI-51-22 being the best blockers.

In further experiments, the selected anti-RANKL antibodies were tested for cross-reactivity to mouse RANKL (see FIG. 4). Table 1 below summarizes the results and indicates that, among others, clones 7, 37, 193, 20, 210, 23, 220, 227, 246, 256, 270, 299, 318, 327, 379, 383, 416, 420, 447, 476, 480,547, 565, EBI-51-4 and EBI-51-23 have strong cross-reactivity to mouse RANKL.

TABLE 1

Cross-reactivity of selected anti-RANKL antibodies with mouse RANKL

| Cross-reactivity | Clones showing reactivity |
| --- | --- |
| strong cross (24 clone) | 7, 37, 193, 20, 210, 23, 220, 227, 246, 256, 270, 299, 318, 327, 379, 383, 416, 420, 447, 476, 480, 547, 565, EBI-51-4, EBI-51-23 |
| no cross (7 clone) | 68, 147, 174, 238, EBI-51-1, EBI-51-22, AMG162 |
| weak cross (9 clone) | 91, 130, 191, 388, 408, 411, 415, 476, EBI-51-2, EBI-51-11 |

The anti-RANKL antibodies were further evaluated using the RAW cell (RAW246.7 cells) assay which tests for inhibition of osteoclast differentiation stimulated by RANKL. The Raw264.7 cell line is a murine macrophage cell line that was derived from a murine leukemia virus-induced tumor. In brief, RAW264.7 cells will differentiate into osteoclast-like cells in the presence of RANKL, and the osteoclast cell differentiation can be measured by TRAP activity, a property of osteoclasts. RAW264.7 cells were incubated for 4 days in the presence of a constant amount of RANKL (40 ng/ml) and various amounts of anti-RANKL antibodies in cell culture medium. At the end of 4 days, the cells were stained for tartrate-resistant acid phosphatase (TRAP) activity by permeabilization and acidification, followed by treatment with para-nitrophenylphosphate for 5 minutes. The reaction was terminated by adding 50 ul of 0.5M NaOH solution. In this assay, the para-nitrophenyl-phosphate is converted to para-nitrophenol by TRAP activity, which can be quantitated by optical density measurement at 405 nm. A plot of optical density versus of anti-RANKL concentration of the top clones is shown in FIG. 5 as compared to the AMG162 benchmark antibody and the 1050 is summarized in Table 2 below. Clones 23, EBI-51-22, 327, 408, 91 and 383 were shown to strongly block the RANKL induced osteoclast differentiation as compared with AMG162.

For the present studies, AMG162 was used as a benchmark. This is a fully human IgG2 antibody specific for RANKL (does not bind to TNFa/b, TRAIL, CD40L). This antibody was generated by CHO-RANKL (full length) cell immunization in Hulg-TG mice (Lymph node fusion) and has high affinity for human RANKL (Kd=$3 \times 10^{-12}$M) It shows inhibition of IC50 RL binding: 9.4 ng/ml and inhibition of IC50 osteoclast like cell formation of 50 ng/ml. AMG162 is human (monkey) specific, but shows no binding to murine RANKL. It has a long PK and PD profile and has been used for the treatment of osteoporosis, bone metastases and rheumatoid arthritis (RA). Its side effects include potential infection, likely through interference with T, B, and DC cell function.

TABLE 2

IC50 for selected anti-RANKL antibodies in a RAW cell assay

| Clone No. | 23 | EBI-51-22 | 327 | 408 | 91 | 383 | AMG162 |
| --- | --- | --- | --- | --- | --- | --- | --- |
| IC50 ng/ml | 1.711 | 3.602 | 7.496 | 6.438 | 4.88 | 2.005 | 9.963 |

The affinity for the top selected anti-RANKL antibodies was tested using surface plasmon resonance and is summarized in Table 3 below. The results showed that clone #23 has a binding affinity that is similar to the benchmark antibody AMG162. Clone #23 showed strong inhibition of osteoclast differentiation, high binding affinity, and cross-reactivity with mouse RANKL and was therefore selected as the top lead candidate for in vivo studies and humanization.

TABLE 3

Summary of affinity measurement using surface plasmon resonance

|   | Clone No. | Ka (1/Ms) | Kd (1/s) | KD (nM) | chi2 |
| --- | --- | --- | --- | --- | --- |
| 1 | 23 | 9.50E+05 | 1.54E−04 | 0.162 | 0.182 |
| 2 | 91 | 4.64E+05 | 2.73E−04 | 0.589 | 0.0656 |
| 3 | 327 | 1.41E+05 | 3.00E−04 | 2.13 | 0.0595 |
| 4 | 408 | 6.07E+05 | 2.62E−04 | 0.432 | 0.0322 |
| 5 | EBI-51-22 | 8.80E+05 | 2.75E−04 | 0.312 | 0.164 |
| 6 | AMG-162 | 1.33E+06 | 1.57E−04 | 0.118 | 0.318 |

Clone #408 and #51-22 also showed strong inhibition of osteoclast differentiation, high binding affinity and no cross-reactivity with mouse RANKL. These clones were selected as backup candidates for humanization.

Humanization Design

Clones 23, 408 and EBI-51-22 were humanized by grafting CDRs to human germline frame. First, the heavy chain (VH) and light chain (VK) variable region sequences of the clones were blasted against the human germline VH and VK database. The closest human germline sequences were identified and used as the template for humanization. Secondly, the rabbit residues in the framework regions potentially involved in CDR contacts or inter-chain contacts were identified based on knowledge from human and mouse antibodies. Residues considered not critical to the structural activity of the antibodies were identified based on knowledge from previous humanized rabbit antibodies.

The amino acid sequences of the humanized VH and VL regions for clone 23 are set forth in SEQ ID NOs: 9, 12, 226 and 10-11 and 227, respectively. Note that 3 different humanized VH and 3 different humanized VL regions were constructed. The humanized VH 23HZD-1 HC is provided in SEQ ID NO: 9 and was tested with both the humanized VLs provided in SEQ ID NOs:10 (#23 VL) and 11 (#23 VLb) (see FIGS. 6-9, 11 and 12 discussed further below). The humanized 23 clone with the highest affinity was the h23n VH and VL as provided in SEQ ID NOs: 226 and 227, respectively (see FIG. 12). The VHCDR1, VHCDR2 and VHCDR3 for the h23n clone are set forth in SEQ ID NOs: 3, 4 and 228, respectively. The VLCDR1, VLCDR2 and VLCDR3 for the h23n clone are set forth in SEQ ID NOs: 15, 7 and 8, respectively. FIG. 1C shows an alignment of the amino acid sequence of the clone 23 parent rabbit and humanized VH and VL.

The amino acid sequences of the humanized VH and VL regions for clone 408 are set forth in SEQ ID NOs: 229 and 230, respectively. An alignment of the amino acid sequence of the clone 408 parent rabbit and humanized VH and VL is shown in FIG. 1D.

The amino acid sequences of the humanized VH and VL regions for clone EBI51-22 are set forth in SEQ ID NOs: 231 and 232, respectively. An alignment of the amino acid sequence of the clone EBI51-22 parent rabbit and humanized VH and VL is shown in FIG. 1E.

Expression of Humanized Clone(s)

The Mutational Lineage Guided (MLG) method was used to humanize clone 23 into a human IgG2 subclass with kappa light chain and humanize 408 and EBI-51-22 into a human IgG1 subclass and kappa light chain. The MLG method is both conceptually and technically different from the CDR-grafting method used in humanizing murine derived antibodies. Humanization guided by both biological and sequence information of a panel of functional antibodies allows for retention of full antibody activity in the humanized antibody. MLG not only humanizes the residues in framework, but also those in CDR regions of the antibody. DNA encoding humanized VK (VK-HZD or VK-HZD-b for clone 23) and VH-HZD were synthesized by MCLab (South San Francisco, Calif., USA). To express the humanized antibodies, the humanized VK fragment was cloned into human CK built-in pTT5 vector at Hind III and Nhe I and, the humanized VH into human IgG2 CH built-in pTT5 vector at Hind III and BsiW I site. DNA and amino acid sequences of human CK and IgG2 CH were chosen for the constant region. Humanized versions of the antibodies were expressed in 293-6E cells, purified through a protein A column and quantified by UV280 after dialyzing against PBS buffer.

Functional Screening of Humanized Candidate Anti-RANKL Antibody Clone 23

Numerous assays were used to characterize the potency of the clone 23, 408 and EBI-51-22 humanized candidate anti-RANKL antibodies identified above. In particular, the rabbit anti-RANKL antibodies and their humanized counterparts were tested for binding to cells expressing RANKL using transfected 293 cells (see FIG. 6). The binding affinity of humanized 23 and 408 is close to their parental rabbit antibodies.

The humanized candidates were further tested for the ability to block receptor-ligand binding in an ELISA (see FIG. 7). In brief, RANK (8 ug/ml) was coated onto 96-well plates 16 hours before the experiment. The plates were subsequently treated with 0.5 ug/ml RANKL preincubated with various concentrations of humanized anti-RANKL antibodies for 30 min at 37° C. A mouse anti-human RANKL antibody was used to detect RANKL and a secondary goat anti-mouse HRP was used to detect the signal. AMG162 was used as positive control. The results demonstrated that all humanized antibodies have comparable blocking activity as compared to their parental rabbit clone and all are more potent than the benchmark AMG162.

In a further experiment, the humanized antibodies were tested for the ability to inhibit RAW cell osteoclast differentiation induced by RANKL (see FIGS. 8 and 9 (mouse)). In brief, RAW264.7 cells were incubated for 4 days in the presence of a constant amount of human RANKL (40 ng/ml) and various amounts of rabbit and humanized anti-RANKL antibodies in cell culture medium. At the end of 4 days, the cells were stained for tartrate-resistant acid phosphatase (TRAP) activity by permeabilization and acidification, followed by treatment with para-nitrophenylphosphate for 5 minutes. The reaction was terminated by adding 50 ul of 0.5M NaOH solution. The para-nitrophenylphosphate was converted to para-nitrophenol by TRAP activity, which was quantitated by optical density measurement at 405 nm. The osteoclast inhibition of two versions of humanized 23 is shown in FIG. 8A and the humanized anti-RANKL 408 and humanized EBI-51-22 is shown in FIG. 8B. The results showed that all of the humanized antibodies have comparable inhibitory effect on osteoclast differentiation in response to human RANKL and all showed more potent or non-inferior activity as compared to AMG162. As shown in FIG. 9A and FIG. 9B, humanized 23 vkb exhibited strong inhibitory effect on the mouse RANKL-induced osteoclast cell differentiation while humanized 408 and EBI-51-22 showed much less effect. AMG162 did not inhibit mouse RANKL induced osteoclast differentiation as this antibody does not bind to mouse RANKL.

In Vivo Efficacy of Humanized Candidate Anti-RANKL Antibody Clone 23

In vivo efficacy was evaluated in a murine osteoporosis model. Four-month old female C57/BL6 mice were ovariectomized (OVX) and 8 additional mice had a sham surgery. The mice were then divided into 6 groups of 8 mice for testing of humanized clone 23, as summarized in Table 4 below.

TABLE 4 in vivo efficacy - osteoporosis model design

| Group No. | Group Title | Animal No. | Time points | Surgery | Dose |
|---|---|---|---|---|---|
| 1 | OVX + Vehicle | 8 | 4 weeks | OVX | — |
| 2 | OVX + RabMAb 23 | 8 | 4 weeks | OVX | 10 mg/kg, SC M & F/week |
| 3 | OVX + humanized 23 VKB | 8 | 4 weeks | OVX | 10 mg/kg, SC M & F/week |
| 4 | OVX + Alendronate | 8 | 4 weeks | OVX | 28 ug/kg, SC M & F/week |

Animals in groups 2-6 were injected subcutaneously with vehicle control, a bisphosphonate positive control (alendronate), or test articles twice per week for 4 weeks, for a total of 8 doses. A quantitative computed tomography (pQCT) bone densitometry machine was used for bone densitometirc analysis. BMD of the right proximal tibia was monitored at weeks 4. The right femur collected at necropsy was scanned for bone density at week 12 with corresponding histology. PD marker was tested at weeks 1, 2, 3 and 4. During the treatment, blood was collected through retro-orbital bleeding 24 hours prior to treatment and every week. TRAP-5b serum concentration, which is a biomarker of in vivo osteoclast activity, was measured by ELISA.

As shown in FIG. 10, in particular, after a single dose of the parent 23 rabbit antibody (1 week), a significantly greater reduction in TRAP5b (tartrate-resistant acid phosphatase 5b; the biomarker of osteoclast activity) activity was observed in the 23 treated group as compared to the control group, indicating stronger inhibition of osteoclast activity in the test group (90% inhibition).

The pQCT results showed that treatment with both rabbit and humanized anti-RANKL 23 resulted in significantly higher bone mass at week 4, as compared to that of the OVX vehicle treated mice for trabecular BMD. While the positive control, alendronate, only exerted marginal effects on the preservation of bone mass (see FIG. 11).

In an additional experiment, binding to RANKL of the h23n IgG2 humanized version of clone 23 was compared with h23 IgG1 and h23 IgG2. For this experiment, both HC and LC were contransfected into 293 cells and secreted antibody was purified. An ELISA assay was used to compare the binding affinity to RANKL protein of h23n IgG2 with h23 IgG1 and h23 IgG2. The results as shown in FIG. 12 showed that the h23n humanized antibody has improved binding affinity as compared to the other humanized versions of clone 23.

In summary, these experiments describe the development of a humanized IgG2 monoclonal antibody against RANKL with high binding affinity to RANKL, (Kd=0.16 nM). The humanized clone 23 is crossreactive with human, monkey and mouse RANKL. This allows for direct evaluation of the antibody in vivo and eases biomarker development. This antibody exhibits potent RANKL neutralizing activities, blocks RANKL binding to RANK receptor, inhibits RANKL-induced osteoclast differentiation and inhibits OVX-induced bone loss in vivo in mice. The humanized 23 anti-RANKL antibody also binds to a different epitope from denosumab (AMG162), which may translate to improvements in safety and efficacy profile.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that binds to receptor activator of nuclear factor kappa-B ligand (RANKL), comprising: (i) a heavy chain variable region (VH) comprising a VH complementarity determining region 1 (VHCDR1) set forth in SEQ ID NO: 3, a VH complementarity determining region 2 (VHCDR2) set forth in SEQ ID NO: 4, and a VH complementarity determining region 3 (VHCDR3) set forth SEQ ID NO: 5; and (ii) a light chain variable region (VL) comprising a VL complementarity determining region 1 (VLCDR1) set forth in SEQ ID NO: 6 or 15, a VL complementarity determining region 2 (VLCDR2) set forth in SEQ ID NO: 7, and a VL complementarity determining region 3 (VLCDR3) set forth in SEQ ID NO: 8.

2. The isolated antibody, or antigen-binding fragment thereof, of claim 1 wherein the heavy chain variable region comprises the amino acid sequence set forth in SEQ ID NO:1.

3. The isolated antibody, or antigen-binding fragment thereof, of claim 1 wherein the light chain variable region comprises the amino acid sequence set forth in SEQ ID NO:2.

4. The isolated antibody of claim 1, wherein the antibody is humanized.

5. The isolated antibody of claim 4, wherein (a) the VH region comprises the amino acid sequence set forth in SEQ ID NO:9 and the VL region comprises the amino acid sequence set forth in SEQ ID NO:10 or 11; or (b) the VH region comprises the amino acid sequence set forth in SEQ ID NO:226 and the VL region comprises the amino acid sequence set forth in SEQ ID NO:227.

6. The isolated antibody, or antigen-binding fragment thereof, of claim 1, comprising the VHCDR1 region set forth in SEQ ID NO:3, the VHCDR2 region set forth in SEQ ID NO:4, and the VHCDR3 region set forth SEQ ID NO:5; and the VLCDR1 region set forth in SEQ ID NO:6, the VLCDR2 region set forth in SEQ ID NO:7, and the VLCDR3 region set forth in SEQ ID NO: 8.

7. The isolated antibody, or antigen-binding fragment thereof, of claim 1, comprising the VHCDR1 region set forth in SEQ ID NO:3, the VHCDR2 region set forth in SEQ ID NO:4, and the VHCDR3 region set forth SEQ ID NO:5; and the VLCDR1 region set forth in SEQ ID NO:15, the VLCDR2 region set forth in SEQ ID NO:7, and the VLCDR3 region set forth in SEQ ID NO: 8.

8. The isolated antibody, or antigen-binding fragment thereof, of claim 6 that binds RANKL with a KD of about 0.16nM or lower.

9. The isolated antibody, or antigen-binding fragment thereof, of claim 6 wherein the isolated antibody, or antigen-binding fragment thereof:
   a. blocks binding of RANKL to receptor activator of nuclear factor kappa-B (RANK);

b. inhibits RANKL-induced osteoclast differentiation;
c. inhibits osteoclast cell activity;
d. inhibits bone loss and increase bone density;
e. Binds and inhibits human, rodent and monkey RANKL; or
f. a combination of any one or more of a. -e.

10. The isolated antibody of claim 1 comprising a human IgG constant domain.

11. The isolated antibody of claim 10 wherein the IgG constant domain comprises an IgG2 CH1 domain or an IgG2 Fc region.

12. The isolated antibody of claim 1 wherein the antibody is a single chain antibody, a ScFv, a univalent antibody lacking a hinge region, a minibody, a Fab, a Fab' fragment, a F(ab')2 fragment, or a whole antibody.

13. The isolated antibody of claim 1, wherein the antibody is a Fab, a Fab', or a F(ab')$_2$ fragment.

14. The isolated antibody of claim 1, wherein the antibody is a whole antibody.

15. A composition comprising a physiologically acceptable carrier and a therapeutically effective amount of the isolated antibody or antigen-binding fragment thereof according to claim 1.

16. An isolated antibody, or an antigen-binding fragment thereof, that binds to receptor activator of nuclear factor kappa-B ligand (RANKL), comprising a heavy chain variable region comprising the amino acid sequence set forth in SEQ ID NO:1.

17. The isolated antibody, or antigen-binding fragment thereof, of claim 16 comprising a light chain variable region which comprises an amino acid sequence having at least 90% identity to the amino acid sequence set forth in SEQ ID NO:2.

18. The isolated antibody, or an antigen-binding fragment thereof, of claim 16 comprising a light chain variable region which comprises the amino acid sequence set forth in SEQ ID NO:2.

19. An isolated antibody, or an antigen-binding fragment thereof, that binds to human receptor activator of nuclear factor kappa-B ligand (RANKL), comprising a light chain variable region comprising the amino acid sequence set forth in SEQ ID NO:2.

20. The isolated antibody, or antigen binding fragment thereof, of claim 19 comprising a heavy chain variable region which comprises an amino acid sequence having at least 90% identity to the amino acid sequence set forth in SEQ ID NO:1.

21. An isolated antibody, or an antigen-binding fragment thereof, that binds to receptor activator of nuclear factor kappa-B ligand (RANKL), comprising (a) a heavy chain variable region comprising the VHCDR1, VHCDR2, and VHCDR3 regions set forth in SEQ ID Nos: 3, 4, and 5, respectively, and a light chain variable region comprising the VLCDR1, VLCDR2, and VLCDR3 regions set forth in SEQ ID Nos: 6, 7, and 8, respectively;

(b) a heavy chain variable region comprising the VHCDR1, VHCDR2, and VHCDR3regions set forth in SEQ ID Nos: 101, 127, and 162, respectively, and a light chain variable region comprising the VLCDR1, VLCDR2, and VLCDR3 regions set forth in SEQ ID Nos 171, 188, and 193, respectively;

(c) a heavy chain variable region comprising the VHCDR1, VHCDR2, and VHCDR3 regions set forth in SEQ ID Nos: 96, 127, and 163, respectively, and a light chain variable region comprising the VLCDR1, VLCDR2, and VLCDR3 regions set forth in SEQ ID Nos: 171, 187, and 208, respectively;

(d) a heavy chain variable region comprising the VHCDR1, VHCDR2, and VHCDR3 regions set forth in SEQ ID Nos: 116, 140, and 150, respectively, and a light chain variable region comprising the VLCDR1, VLCDR2, and VLCDR3 regions set forth SEQ ID Nos: 171, 180, and 212, respectively; or (e) a heavy chain variable region comprising the VHCDR1, VHCDR2, and VHCDR3 regions set forth in SEQ ID Nos: 115, 145, and 148, respectively, and a light chain variable region comprising the VLCDR1, VLCDR2, and VLCDR3 regions set forth in SEQ ID Nos: 171, 183, and 224, respectively.

* * * * *

UNITED STATES PATENT AND TRADEMARK OFFICE
CERTIFICATE OF CORRECTION

PATENT NO. : 10,259,878 B2
APPLICATION NO. : 14/776248
DATED : April 16, 2019
INVENTOR(S) : Yongke Zhang et al.

Page 1 of 1

It is certified that error appears in the above-identified patent and that said Letters Patent is hereby corrected as shown below:

In the Claims

Column 166, Line 47, In Claim 6, "VHCDR1region set forth" should read -- VHCDR1 region set forth Column 166, Line 55, In Claim 7, "VHCDR2region set forth" should read -- VHCDR2 region set forth Column 167, Line 6, In Claim 9, "a combination of any one or more of a. -e." should read -- a combination of any one or more of a. - e.

Column 168, Line 18, In Claim 21, "VHCDR3regions set forth" should read -- VHCDR3 regions set forth Signed and Sealed this
Sixth Day of August, 2019

Andrei Iancu
*Director of the United States Patent and Trademark Office*